US007750211B2

(12) United States Patent
Dixon et al.

(10) Patent No.: US 7,750,211 B2
(45) Date of Patent: Jul. 6, 2010

(54) METHODS AND COMPOSITIONS FOR PRODUCTION OF FLAVONOID AND ISOFLAVONOID NUTRACEUTICALS

(75) Inventors: Richard A. Dixon, Ardmore, OK (US); Chang-Jun Liu, La Jolla, CA (US); Bettina Deavours, Ardmore, OK (US)

(73) Assignee: The Samuel Roberts Noble Foundation, Ardmore, OK (US)

(*) Notice: Subject to any disclaimer, the term of this patent is extended or adjusted under 35 U.S.C. 154(b) by 953 days.

(21) Appl. No.: 10/659,755

(22) Filed: Sep. 10, 2003

(65) Prior Publication Data

US 2004/0128711 A1 Jul. 1, 2004

Related U.S. Application Data

(60) Provisional application No. 60/409,447, filed on Sep. 10, 2002.

(51) Int. Cl.

| | |
|---|---|
| ***C12N 15/29*** | (2006.01) |
| ***C12N 15/52*** | (2006.01) |
| ***C12N 15/82*** | (2006.01) |
| ***A01H 5/00*** | (2006.01) |
| ***A01H 5/10*** | (2006.01) |

(52) U.S. Cl. ....................... 800/312; 800/286; 800/306; 800/314; 800/317.2; 800/317.3; 800/317.4; 800/320; 800/320.1; 800/320.2; 800/320.3

(58) Field of Classification Search ................. 800/282, 800/285, 286, 298

See application file for complete search history.

(56) References Cited

U.S. PATENT DOCUMENTS

| | | | | |
|---|---|---|---|---|
| 6,121,512 A | 9/2000 | Siminszky et al. | .......... | 800/298 |
| 7,098,011 B1 * | 8/2006 | Fader et al. | ................. | 435/189 |
| 7,189,895 B2 * | 3/2007 | McGonigle et al. | ......... | 800/312 |
| 7,244,599 B2 | 7/2007 | Tanner et al. | ............... | 435/189 |
| 2004/0093632 A1 | 5/2004 | Dixon et al. | ................ | 800/278 |
| 2006/0123508 A1 | 6/2006 | Dixon et al. | ................ | 800/278 |

FOREIGN PATENT DOCUMENTS

| | | |
|---|---|---|
| WO | WO 00/53771 | 3/2000 |
| WO | WO 00/44909 | 8/2000 |
| WO | WO 03/031622 | 4/2003 |
| WO | WO 03/040306 | 5/2003 |
| WO | WO 03/093464 | 11/2003 |
| WO | WO 03/106633 | 12/2003 |
| WO | WO 2004/090136 | 10/2004 |

OTHER PUBLICATIONS

Wisman et al. PNAS, Oct. 1998, vol. 95, pp. 12432-12437.*

Yu O. et al. Plant Physiology, 2000; vol. 124, pp. 781-793.*

Dixon et al., "Metabolic Engineering of Flavonoid/Isoflavonoid Biosynthesis," *Abstracts of Papers American Chemical Society*, 219, Abstract 152, 2000.

Liu et al., "Direction Metabolic Flux Toward Engineered Isoflavone Nutraceuticals in Transgenic *Arabidopsis*," In: Plant Biotechnology 2002 and Beyond: Proceedings of the 10$^{th}$ IAPTC&B Congress, Vasil (ed.), Kulwer Academic Publishers, Dordrecht, 2003.

Liu et al., "Metabolic engineering of isoflavonoid biosynthesis in *Arabidopsis thaliana," Plant Biology*, Abstract 209, 2000.

White and Greenwood, "Transformation of the forage legume *Trifolium repens* L. using binary Agrobactrium vectors," *Plant Molecular Biology*, 8:461-469, 1987.

Yu et al., "Metabolic engineering to increase isoflavone biosynthesis in soybean seed," *Phytochemistry*, 63:753-763, 2003.

GenBank GI:166397, Jan. 29, 1997.

GenBank GI:393000, Jan. 30, 1997.

GenBank GI:456399, Jan. 28, 1997.

Kim et al., "*Brassica rapa* has three genes that encode proteins associated with different neutral lipids in plastids of specific tissues," *Plant Physiology*, 126:330-341, 2001.

Liu et al., "Bottlenecks for metabolic engineering of isoflavone glycoconjugates in *Arabidopsis," PNAS*, 99:14578-14583, 2002.

Yu et al., "Production of the isoflavones genistein and daidzein in non-legume dicot and monocot tissues," *Plant Physiology*, 1224:781-793, 2000.

Wisman et al., "Knock-out mutants from an En-1 mutagenized *Arabidopsis thaliana* population generate phenylpropanoid biosynthesis phenotypes," *Proc. Natl. Acad. Sci. USA*, 95:12432-12437, 1998.

Akashi et al., "Cloning and functional expression of a cytochrome P450 cDNA encoding 2-hydroxyisoflavanone synthase involved in biosythesis of the isoflavanoid skeleton in licorice," *Plan Physiol.*, 121:821-828, 1999.

Dixon et al., "Comparative bichemistry of chalcone isomerases," *Phytochemistry*, 27(9):2801-2808, 1988.

Dixon, In: *Comprehensive Natural Products Chemistry*, vol. 1, Sankawa (ed.), Elsevier, 773-823, 1999.

Dixon and Ferriera, "Molecules of interest: Genistein," *Phytochemistry*, 60:205-211, 2002.

Dong et al., "Functional conservation of plant secondary metabolic enzymes revealed by complementation of *Arabidopsis* flavanoid mutants with maize genes," *Plant Physiology*, 127:46-57, 2001.

GenBank Accession No. AC092697.

GenBank Accession No. AF022462.

GenBank Accession No. AJ278457.

GenBank Accession No. AJ295587.1.

GenBank Accession No. M91079.

(Continued)

*Primary Examiner*—Russell Kallis

(74) *Attorney, Agent, or Firm*—Steven P. Rhines, Esq.; Sonnenschein Nath & Rosenthal LLP

(57) ABSTRACT

The invention provides method and compositions for the modulation of flavanone and/or isoflavone production in plants. The methods of the invention allow creation of plants having novel phenotypes. Increased expression of isoflavones in particular in plants may be used to increase the nutritional value of food plants for both human and animal consumption. The invention overcomes limitations of the prior art which prevented accumulation of high levels of isoflavones in plants.

42 Claims, 7 Drawing Sheets

OTHER PUBLICATIONS

Hakamatsuka et al., "Purification of 2-hydroxyisoflavanone dehydratase from the cell cultures of pueraria lobata," *Phytochemistry*, 49(2):497-505, 1998.

Jung et al., "Identification and expression of isoflavone synthase, the key enzyme for biosynthesis of isoflavones in legumes," *Nature BioTech.*, 18:208-212, 2000.

Junghans et al., "Stress responses in alfalfa (*Medicago sativa* L.). 15. Characterization and expression patterns of members of a subset of the chalcone synthase multigene family," *Plant Mol. Biol.*, 22:239-253, 1993.

McKhann and Hirsch, "Isolation of chalcone synthase and chalcone isomerase cDNAs from alfalfa (*Medicago sativa* L.): highest transcript levels occur in young roods and root tips," *Plant Mol. Biol.*, 24(5):767-777, 1994.

Muir et al., "Overexpression of petunia chalone isomerase in tomato results in fruit containing increased levels of flavonols," *Nature Biotech.*, 19:470-474, 2001.

Schröder, "A family of plant-specific polyketide synthases: facts and predictions," *Trends in Plant Sci.*, 2(10):373-378, 1997.

Steele et al., "Molecular characterization of the enzyme catalyzing the aryl migration reaction of isoflavaniod biosynthesis in soybean," *Arch. Biochem. Biophys.*, 367(1):146-150, 1999.

Stochmal et al., "Alfalfa (*Medicago sativa* L.) flavanoids. 2. Tricin and chrysoeriol clycosides from aerial parts," *J. Agric. Food Chem.*, 49:5310-5314, 2001.

Stochmal et al., "Alfalfa (*Medicago sativa* L.) flavaniods. 1. Apigenin and luteolin glycosides from aerial parts," *J. Agric. Food Chem.*, 49:753-758, 2001.

Winkel-Shirley, "Evidence for enzyme complexes in the phenylpropanoid and flavanoid pathways," *Physiologia Plantarium*, 107:142-149, 1999.

Ye et al., "Engineering the provitamin A (β-carotene) biosynthetic pathway into (carotenoid-free) rice endosperm," *Science*, 287:303-305, 2000.

Yu et al., "Production of the isoflavones genistein and daidzein in non-legume dicot and monocot tissues," *Plant Physiology*, 124:781-794, 2000.

* cited by examiner

METHODS AND COMPOSITIONS FOR PRODUCTION OF FLAVONOID AND ISOFLAVONOID NUTRACEUTICALS

This application claims the priority of U.S. Provisional Patent Application Ser. No. 60/409,447, filed Sep. 10, 2002, the entire disclosure of which is specifically incorporated herein by reference.

BACKGROUND OF THE INVENTION

1. Field of the Invention

The present invention generally relates to plant genetics. More specifically, the invention relates to methods and compositions for the modulation of flavonoid and isoflavonoid biosynthesis in plants.

2. Description of the Related Art

Isoflavonoid natural products are limited primarily to leguminous plants, where they function as pre-formed or inducible antimicrobial or anti-insect compounds, as inducers of the nodulation genes of symbiotic Rhizobium bacteria, and as allelopathic agents (Dixon, 1999). However, much attention is now being focused on the simple isoflavones daidzein and genistein in view of many reports linking their dietary consumption to a range of potential health benefits (Barnes, 1998; Barnes, 1996; Adlercreutz. and Mazur, 1997; Adlercreutz, 1998; Dixon, 1999; Dixon, 2002). The major dietary sources of these compounds for humans are soybean seed products, which are rich in daidzein and genistein, and chickpea seeds, which also contain biochanin A (4'-O-methylgenistein). The structures of these isoflavones are shown in FIG. 1.

Epidemiological studies have demonstrated a link between consumption of soy isoflavones and reduced risks of breast and prostate cancers in humans (Messina et al., 1994; Adlercreutz, 1998). Genistein and biochanin A exhibit chemopreventative activity against chemically-induced cancers in a number of mammalian cell model systems (Fotsis et al., 1995; Lamartiniere et al., 1995; Rauth et al, 1997; Uckun et al., 1995; Yanagihara et al., 1993). Furthermore, isoflavones have been shown to possess other health promoting activities, including potential chemoprevention of osteoporosis and cardiovascular disease (Anderson and Garner, 1998; Draper et al., 1997; Tikkanen et al., 1998; Wagner et al., 1997). In addition to isoflavonoids, many other flavonoid-derived compounds have been ascribed health-promoting activity. These include flavonols, such as quercetin, that occur at significant levels in leaves and fruit of many plant species and that have high antioxidant activity (Rice-Evans and Miller, 1996).

Isoflavonoids are formed by a branch of the flavonoid biosynthetic pathway, and originate from a central flavanone intermediate that is ubiquitously present in plants. For entry into the isoflavonoid pathway, the flavanone naringenin undergoes migration of the B-ring from the 2- to the 3-position followed by hydroxylation at the 2-position catalyzed by a microsomal cytochrome P450 enzyme, CYP93C1 (2-hydroxyisoflavanone synthase or 2-HIS, also commonly termed isoflavone synthase (IFS) (FIG. 1). The resulting 2-hydroxyisoflavanone then undergoes dehydration to yield the corresponding isoflavone genistein (Hakamatsuka et al., 1990; Kochs and Grisebach, 1986), as shown in FIG. 1. The dehydration reaction can take place non-enzymatically in vitro under acid conditions (Kochs and Grisebach, 1986), although an enzyme has been purified from cell cultures of *Pueraria lobata* that can catalyze this reaction (Hakamatsuka et al., 1998). This dehydratase appears to be closely associated with the microsomal aryl migration enzyme (Hakamatsuka et al., 1998).

cDNA clones that encode IFS have been characterized from soybean and other legumes (Akashi et al., 1999; Jung et al., 2000; Steele et al., 1999). The soybean enzyme is classified as CYP93C1v2. When expressed in insect cells, it converts the flavanones liquiritigenin and naringenin directly to their corresponding isoflavones daidzein and genistein in the presence of NADPH (Steele et al., 1999), as shown in FIG. 1. It is not clear whether dehydration of the putative 2-hydroxyisoflavanone intermediate occurs on the enzyme, or results from an endogenous dehydratase activity present in the insect cell microsomes. The aryl migration enzyme from licorice (*Glycyrrhiza echinata*) has been shown to produce a 2-hydroxyisoflavanone from a flavanone when expressed in yeast (Akashi et al., 1999).

There have been few reports to date on the introduction of new natural product pathways into plants through genetic manipulation. An important recent example is the introduction of the provitamin A pathway into rice, a process that involved the introduction of three genes (Ye et al., 2000). The soybean IFS has been introduced into the model crucifer *Arabidopsis thaliana* by *Agrobacterium*-mediated transformation (Jung et al., 2000; International Application No. PCT/US00/05915, filed Mar. 8, 2000) and into tobacco and corn by *Agrobacterium* or biolistic bombardment methods, respectively (Yu et al., 2000). These studies have shown the production of low levels of genistein (up to a maximum of around 40 nmol/g fresh weight, but generally less) after hydrolysis of potential genistein glyco-conjugates that may have been formed in the transgenic plants. The nature of the potential glyco-conjugates has not been determined. While these studies confirm production of isoflavones in transgenic plants, it would be advantageous to increase the amount of flavonoid natural products produced by the transgenic plants to provide improved bioactivity for dietary health-promotion.

The key biosynthetic reactions leading to the formation of flavanone are catalyzed by chalcone synthase (CHS) and chalcone isomerase (CHI). CHS is a homodimeric polyketide synthase that forms 2',4,'4',6'-tetrahydroxychalcone (naringenin chalcone) from three molecules of malonyl coenzyme A and one molecule of 4-coumaroyl CoA according to the reaction shown in FIG. 1. It is often encoded by a multigene family in legumes (Junghans et al., 1993), and many CHS genes have been cloned from a wide number of plant species, including alfalfa (Schröder, 1997).

CHI is a monomeric enzyme that very efficiently catalyzes the isomerization of naringenin chalcone to its corresponding flavanone, naringenin (4',5,7-trihydroxy-flavanone), as depicted in FIG. 1. This reaction can also occur spontaneously at alkaline pH, although without a stereochemical direction (CHI specifically catalyzes formation of (−) flavanone). For this reason, few plants accumulate naringenin chalcone. CHI from certain legumes can also act on 2',4,4'-trihydroxychalcone (isoliquiritigenin), to form the corresponding flavanone liquiritigenin (4', 7, dihydroxy-flavanone) (Dixon et al., 1988), whereas the enzyme from most non-legumes does not appear to have this activity. CHI genes have now been cloned from several species, including alfalfa (McKhann and Hirsch, 1994). In view of its high activity level in many plant tissues relative to the activity level of CHS, CHI has not heretofore been thought of as a rate-determining enzyme for flavanone formation. However, it has recently been shown that CHI is rate limiting for flavonoid biosynthesis in tomato fruit peel (Muir et al., 2001).

However, in that particular study, expression of the 35S promoter driven petunia CHI transgene did not increase flavonol levels in the flesh of the fruit, or in the leaves. The peel of wild-type tomato fruit unusually contains high levels of naringenin chalcone but very low levels of flavonols, suggesting limitation of CHI activity and explaining the approximately 80-fold increase in flavonols following expression of the CHI transgene (Muir et al., 2001). Such an increase was not observed when maize CHI was over-expressed in wild-type *Arabidopsis* and, in fact, such plants appeared to have reduced levels of anthocyanins (Dong et al., 2001).

The foregoing studies have provided a further understanding of the metabolism of plant secondary metabolism. However, the prior art has failed to provide techniques for the application of this understanding to the creation of plants having valuable new characteristics. What are thus needed are practical techniques for the production of novel plants with improved phenotypes and methods for the use thereof. Such techniques may allow the creation and use of plants with improved nutritional quality, thereby benefiting both human and animal health and representing a substantial benefit in the art.

SUMMARY OF THE INVENTION

In one aspect, the invention provides a method of increasing isoflavonoid biosynthesis in a plant comprising: a) down-regulating flavanone 3-hydroxylase in said plant; and b) up-regulating isoflavone synthase and/or the production of a substrate thereof in said plant. The plant may comprise a mutant flavanone 3-hydroxylase gene exhibiting a loss of function with respect to a flavanone 3-hydroxylase gene lacking said mutation. In one embodiment of the invention, isoflavone synthase is upregulated in the plant. Such upregulating may comprise, in certain embodiments, introducing a transgene into the plant encoding isoflavone synthase into said plant. The transgene may be introduced by any method, including genetically transforming said plant or a parent plant of any previous generation of said plant with said transgene. In certain embodiment of the invention, the isoflavone synthase comprises the polypeptide sequence of SEQ ID NO:2.

In further embodiments of the invention, a method of increasing isoflavonoid biosynthesis may comprise up-regulating chalcone isomerase in said plant, including the polypeptide sequence encoded by SEQ ID NO:3. Such up-regulating may comprise introducing a transgene encoding said chalcone isomerase into said plant by any method, including genetically transforming said plant or a parent plant of any previous generation of said plant with said transgene. The method may also comprise introducing a transgene encoding the PAP1 gene into said plant. In still further embodiments of the invention, the method may comprise up-regulating chalcone synthase in said plant, for example, where chalcone synthase comprises the polypeptide sequence encoded by SEQ ID NO:5 or SEQ ID NO:6.

In one embodiment of the invention, the method of increasing isoflavonoid biosynthesis, down-regulating flavanone 3-hydroxylase comprises introducing a selected DNA into said plant comprising an antisense nucleotide comprising from about 20 or more nucleotides complementary to a gene encoding flavanone 3-hydroxylase. In certain embodiments of the invention, the antisense oligonucleotide comprises from about 20 to about 1242 nucleotides complementary to the nucleic acid sequence of (SEQ ID NO:10), from about 20 to about 815 nucleotides complementary to the nucleic acid sequence of (SEQ ID NO:13) or from about 20 to about 5586 nucleotides complementary to nucleotides 82850-88437 of (SEQ ID NO:15). In still further embodiments, the antisense oligonucleotide is further defined as comprising from about 20 to about 780 nucleotides complementary to nucleotides 82850-83062, 83159-83406, 86908-87232, and/or 87801-88437 of (SEQ ID NO:15), or is further defined as comprising from about 20 to about 1021 nucleotides complementary to nucleotides 82850-83062, 83159-83406, 86908-87232, and/or 87801-88043 of (SEQ ID NO:15). The antisense oligonucleotide may be introduced by any method, including genetically transforming said plant or a parent plant of any previous generation of said plant with said selected DNA.

The method of increasing isoflavonoid biosynthesis in a plant may be carried out on any plant. In one embodiment of the invention, the plant is a monocotyledonous plant. Examples of monocotyledonous plants include wheat, maize, rye, rice, oat, barley, turfgrass, sorghum, millet and sugarcane. The plant may also be a dicotyledonous plant. Examples of dicotyledonous plants include tobacco, tomato, potato, soybean, cotton, canola, alfalfa, sunflower, and cotton.

In another aspect, the invention provides a transgenic plant stably transformed with: a) a first selected DNA comprising a nucleic acid encoding an antisense oligonucleotide operably linked to a promoter functional in said plant, wherein said antisense oligonucleotide comprises from about 20 to about 1242 nucleotides complementary to the nucleic acid sequence of (SEQ ID NO:10), from about 20 to about 815 nucleotides complementary to the nucleic acid sequence of (SEQ ID NO:13) or from about 20 to about 5586 nucleotides complementary to nucleotides 82850-88437 of (SEQ ID NO:15); and b) a second selected DNA comprising an isoflavone biosynthesis-coding sequence operably linked to a promoter functional in said plant, wherein the coding sequence encodes a polypeptide selected from the group consisting of: the polypeptide of SEQ ID NO:2, the polypeptide encoded by SEQ ID NO:3, the polypeptide encoded by SEQ ID NO:5 and the polypeptide encoded by SEQ ID NO:6.

The first selected DNA and/or said second selected DNA may comprise an enhancer, plasmid DNA, and/or a sequence encoding a signal peptide. In one embodiment of the invention, the transgenic plant is further defined as a fertile $R_0$ transgenic plant. In another embodiment, the plant is further defined as a progeny plant of any generation of a fertile $R_0$ transgenic plant, wherein said transgenic plant has inherited said first selected DNA from said $R_0$ transgenic plant. In yet another embodiment, the transgenic plant is further defined as a progeny plant of any generation of a fertile $R_0$ transgenic plant, wherein said transgenic plant has inherited said second selected DNA from said $R_0$ transgenic plant. The transgenic plant may also have inherited said first and said second selected DNA from said $R_0$ transgenic plant. The first selected DNA and said second selected DNA may also have been transformed into said plant or a progenitor thereof on a single transformation construct.

In certain embodiments of the invention, the transgenic plant of claim 21, wherein the antisense oligonucleotide is further defined as comprising from about 20 to about 780 nucleotides complementary to nucleotides 82850-83062, 83159-83406, 86908-87232, and/or 8780 1-88437 of (SEQ ID NO:15). The antisense oligonucleotide may also be further defined as comprising from about 20 to about 1021 nucleotides complementary to nucleotides 82850-83062, 83159-83406, 86908-87232, and/or 87801-88043 of (SEQ ID NO:15).

In yet another aspect, the invention provides a seed of a plant of the invention, wherein said seed comprises said first selected DNA and said second selected DNA.

In still yet another aspect, the invention provides a method of making food for human or animal consumption comprising: (a) obtaining the plant of claim 21; (b) growing said plant under plant growth conditions to produce plant tissue from the plant; and (c) preparing food for human or animal consumption from said plant tissue. In the method, preparing food may comprise harvesting said plant tissue. In certain embodiments, the food may be starch, protein, meal, flour or grain.

In still yet another aspect, the invention provides a method of producing a nutraceutical composition comprising (a) obtaining a plant in accordance with the invention; (b) growing said plant under plant growth conditions to produce plant tissue from the plant; and (c) preparing a nutraceutical composition for human or animal consumption from said plant tissue.

In still yet another aspect, the invention provides a method of inhibiting the initiation and promotion of a mammalian cell to a premalignant or malignant state in a mammal comprising: (a) obtaining the plant in accordance with the invention; (b) growing said plant under plant growth conditions to produce plant tissue from the plant; (c) preparing a nutraceutical composition for human or animal consumption from said plant tissue; and (d) administering a therapeutically effective amount of the nutraceutical composition to the mammal. In one embodiment of the invention, the mammal is a human. In further embodiments, administering is oral or topical.

In still yet another aspect, the invention provides a method of inhibiting the onset of cardiovascular disease in a mammal comprising: (a) obtaining a plant in accordance with the invention; (b) growing said plant under plant growth conditions to produce plant tissue from the plant; (c) preparing a nutraceutical composition for human or animal consumption from said plant tissue; and (d) administering a therapeutically effective amount of the nutraceutical composition to the mammal. In the method, the mammal may be a human. In one embodiment of the invention, administering is oral and/or topical.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein.

DETAILED DESCRIPTION OF THE INVENTION

Figure 1:
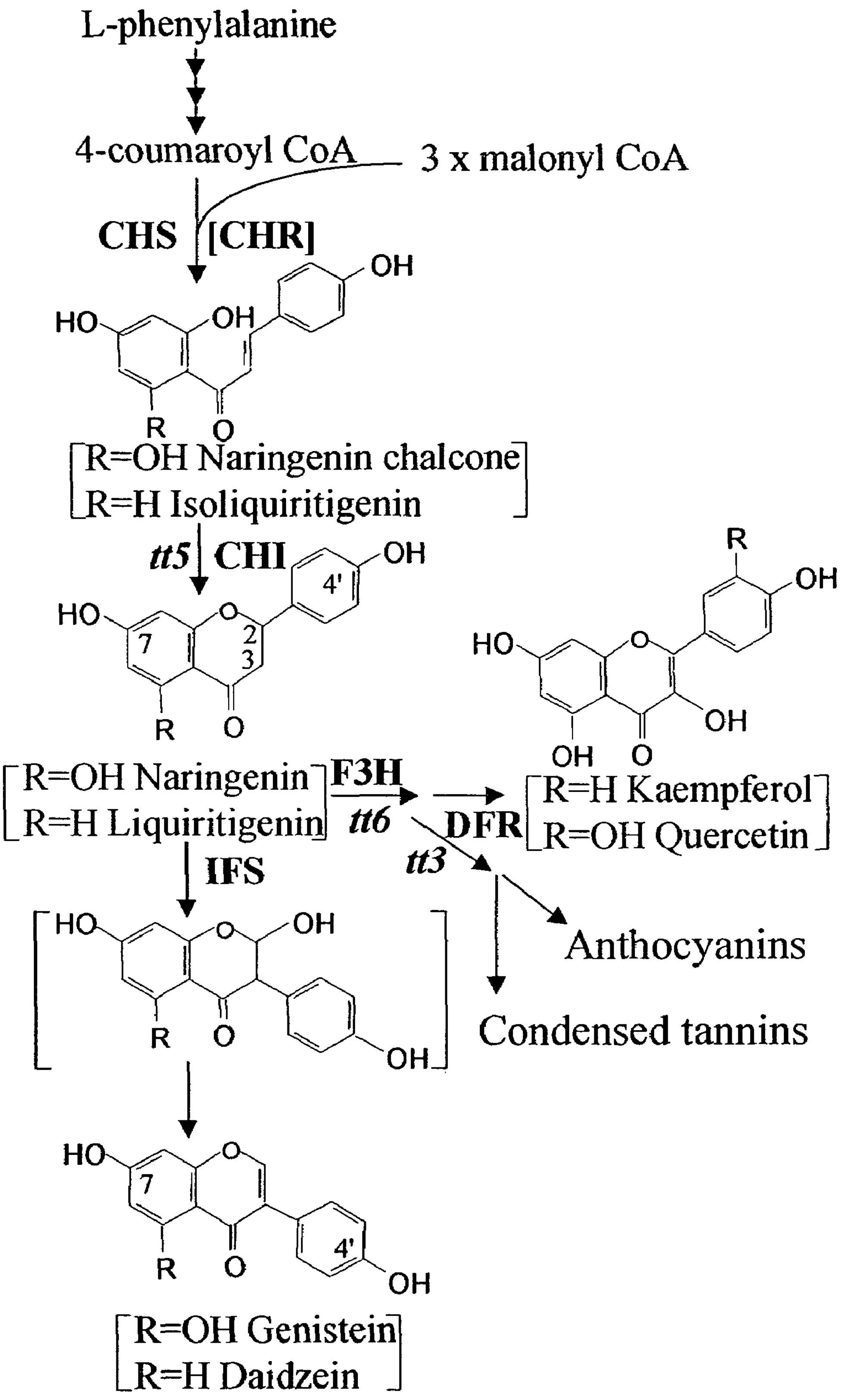
FIG. 1: Depicts the reactions catalyzed by chalcone synthase (CHS) and chalcone isomerase (CHI) and the formation of isoflavones from flavanones. Daidzein (R═H) is produced from liquiritigenin, and genistein (R═OH), from naringenin. Naringenin is the product of the action of chalcone isomerase (CHI) on 2',4,4',6'-tetrahydroxychalcone, formed from malonyl CoA and 4-coumaroyl CoA by chalcone synthase (CHS). Formation of liquiritigenin requires the activity of a chalcone reductase (CHR) that co-acts with chalcone synthase (CHS) to form 2',4,4'-trihydroxychalcone followed by the action of chalcone isomerase (CHI). CHI from alfalfa is active against both isoliquiritigenin (2',4,4'-trihydroxychalcone) and naringenin chalcone (2',4,4',6'-tetrahydroxychalcone), whereas CHI from *Arabidopsis* is only active against naringenin chalcone.

The invention overcomes the deficiencies of the prior art by providing methods and compositions for producing plants with enhanced isoflavonoid biosynthesis. Although production of flavonoid metabolites to increase flavonoid precursors can be achieved, for example, by expressing a chalcone isomerase, high concentrations of isoflavonoids have not been achieved. For example, transformation of *Arabidopsis* with soybean isoflavone synthase (IFS), which is also known as 2-hydroxyisoflavanone synthase (2-HIS), in the absence of an introduced 2-hydroxyisoflavanone dehydratase or soybean cytochrome P450 reductase results in production of low levels of genistein in the leaves. *Arabidopsis* appears to glycosylate this new natural product in an identical manner to its endogenous flavonols, namely by conjugation to the sugars rhamnose and/or glucose. *Arabidopsis* plants expressing both a soybean IFS gene and an alfalfa CHI gene do not, however, produce higher amounts of genistein than plants expressing the IFS alone. Thus, the production of antioxidant flavonoids in transgenic plants can be significantly increased by expression of the alfalfa CHI transgene, but other strategies are necessary to obtain significant improvement in isoflavone accumulation.

However, in accordance with the present invention, high levels of isoflavonoid production may be achieved in plants through down-regulation of flavanone 3-hydroxylase (F3H). That is, it has been found that the major problem in previous attempts at engineering isoflavone biosynthesis is the partition of flux between flavonol and isoflavone biosynthesis. This occurs at the level of the flavanone naringenin, which is substrate for both IFS and flavanone 3-hydroxylase (F3H). It has been proposed that a physical complex exists involving CHS, CHI and F3H (Winkel-Shirley, 1999), but the implication with respect to engineering isoflavone biosynthesis has not been known.

The inventors have shown that introduction of isoflavone synthase into plants in which the flavanone 3-hydroxylase is down-regulated results in significant improvement to the levels of accumulation of the isoflavone genistein. This can be coupled with increasing flux into the production of naringenin to result in even further enhancement of isoflavone production. The present invention thus provides for transformation of plants or plant cells with an isoflavone synthase (2-HIS) gene to produce isoflavonoids or glycosides of isoflavonoids. Such plants or plant cells may comprise a down-regulated flavanone 3-hydroxylase relative to other plants of the same variety. Such down-regulation may comprise, for example, use of a naturally-occurring or induced mutant flavanone 3-hydroxylase allele, as well as using antisense or other technology. The down-regulation may comprise complete elimination of expression of flavanone 3-hydroxylase or may comprise a partial decrease in expression.

The present invention also provides for transformation of plants or plant cells with a chalcone isomerase gene to produce increased levels of flavonoid natural products. The present invention provides for transformation of a plant lacking expression of flavanone 3-hydroxylase with IFS in order to produce high accumulation of isoflavones. The invention provides for co-transformation of plants or plant cells lacking flavanone 3-hydroxylase with an isoflavone synthase gene and/or a chalcone isomerase gene to produce isoflavonoids. The invention also provides for other approaches for the generation of transgenic plants expressing an isoflavone synthase gene with parallel over-expression of chalcone isomerase, or any other gene that will increase flux into production of naringenin, and down-regulation of flavanone 3-hydroxylase or any other gene that will block flux into flavonoid biosynthesis downstream of naringenin. Such plants include, for example, vegetables, grains, and fruit, both dicots and monocots, including but not limited to alfalfa, soybean, tomato, lettuce, tobacco, corn, maize, cotton, squash, beans and other legumes, melons, broccoli and other cole crops, stone fruits, citrus fruits, and strawberries. As used herein, unless otherwise stated, the term "plant" or "progeny" includes plant parts, plant tissue, plant cells, plant protoplasts, plant cell tissue cultures from which plants can be regenerated, plant calli, plant clumps, explants, plant cells that are intact in plants, or parts of plants, such as embryos, pollen, ovules, flowers, capsules, stems, leaves, seeds, roots, root tips, and the like.

The methods of producing isoflavonoids or flavonoid natural products from transgenic plants or cells from transgenic plants provided herein presents advantages over production methods which utilized nontransgenic plants in which isoflavonoids or flavonoid natural products occur naturally. The present invention expands the production of isoflavonoids or flavonoid natural products to a wide variety of edible plants, resulting in (1) increased sources for the procurement of isoflavonoids or flavonoid natural products; (2) a larger growing region for isoflavonoid-producing or flavonoid natural product-producing plants which potentially leads to increased production; (3) reduction in seasonal and/or climate limitations associated with nontransgenic isoflavonoid-producing or flavonoid natural product-producing plants; and (4) increased consumer satisfaction.

In the present invention, a plant can be transformed with an isoflavone synthase cDNA or genomic clone; a chalcone isomerase cDNA or genomic clone; or co-transformed with an isoflavone synthase cDNA or genomic clone and a chalcone isomerase cDNA or genomic clone, as well as any synthetic coding sequences of these nucleic acids. In the present invention, plants or plant cells with reduced flavanone 3-hydroxylase expression can be mutant, or generated by antisense, gene silencing (sense suppression), RNAi or other recombinant technologies known to those skilled in the art for down-regulating the expression and/or activity of a given enzyme.

Transgenically produced isoflavonoids or flavonoid natural products may be administered orally by directly ingesting the transgenic plant. Alternatively, the transgenically produced isoflavonoids or flavonoid natural products can be isolated from transgenic plants to be used as a crude extract or purified compound. Administration of transgenically produced isoflavonoids or flavonoid natural products to humans or animals provides enhanced pharmaceutical and nutraceutical effects, including but not limited to anticancer, anti-osteoporosis, anti-oxidant and cardiovascular benefits.

Transformation methods useful in the present invention include but are not limited to *Agrobacterium tumefaciens*-mediated transformation by vacuum infiltration or leaf disc transformation, biolistic particle bombardment, pollen transformation, protoplast electroporation, or permeabilization. Likewise, several methods known in the art can be used to distinguish the progeny exhibiting stable inheritance of the transgene. For transgenic plants wherein the transgenic cassette contains a gene coding for a visible phenotypic change, the selection can be based upon visual examination of the progeny. For plant transformations involving a selectable marker gene, the appropriate selectable agent can be applied to the plants to select the transformants. Optionally, Southern blot analysis or PCR analysis can be used to verify the presence of the transferred gene in the genome of the transformed plants. RNA gel blot analysis, RT-PCR, or similar techniques can be used to verify the transcription of the transferred gene in transformed tissues. Progeny which are stably transformed and successfully accumulating isoflavonoids or flavonoid natural products can be identified by chemically analyzing the plant tissues for their presence, using chemical methods including but not limited to organic extraction followed by high pressure liquid chromatography (HPLC), liquid chromatography-mass spectrometry (LC/MS), gas chromatography (GC), gas chromatography-mass spectrometry (GC-MS), or capillary electrophoresis (CE).

I. Plant Transformation Constructs

Certain embodiments of the current invention concern plant transformation constructs. For example, one aspect of the current invention is a plant transformation vector comprising one or more flavonoid and/or isoflavonoid biosynthesis gene. Exemplary coding sequences for use with the invention include chalcone isomerase (SEQ ID NO:3 and SEQ ID NO:4); chalcone synthase (SEQ ID NO:5 and SEQ ID NO:6) and isoflavone synthase (SEQ ID NO:1). In certain embodiments, antisense flavanone 3-hydroxylase sequences are employed with the invention. Exemplary flavanone 3-hydroxylase nucleic acids include at least 20, 40, 80, 120, 300 and up to the full length of the nucleic acid sequences of (SEQ ID NO:10) (*Arabidopsis thaliana*; Genbank Accession No. AJ295587.1), (SEQ ID NO:15) (rice; Genbank Accession No. AC092697; gene: 82850-88437; mRNA: 82850-83062, 83159-83406, 86908-87232, and 87801-88437; coding sequence: 82850-83062, 83159-83406, 86908-87232, and 87801-88043) and (SEQ ID NO:13) (*Juglans nigra*; Genbank Accession No. AJ278457) may be used. Examples of certain such sequences, each of which may be used, for example, as antisense oligonucleotides, include the nucleic acid sequences of nucleotides 82850-82870, 82850-82890, 82850-82950, 82850-83062, 83159-83179, 83159-83259, 86908-86928, 86908-87008, 86908-87202, 87801-87821, 87801-87901 and/or 87801-88001 of (SEQ ID NO:15). Other exemplary sequences include the sequences of nucleotides 1-20, 1-40, 1-100, 100-300, 1-300, 1-500, 1-800 and 1-1242 of (SEQ ID NO:10), as well as 1-20, 1-40, 1-100, 100-1300, 1-800 and 1-815 of (SEQ ID NO:13).

In certain embodiments of the invention, coding sequences are provided operably linked to a heterologous promoter, in either sense or antisense orientation. Expression constructs are also provided comprising these sequences, as are plants and plant cells transformed with the sequences. The construction of constructs which may be employed in conjunction with plant transformation techniques using these or other sequences according to the invention will be known to those of skill of the art in light of the present disclosure (see, for example, Sambrook et al., 1989; Gelvin et al., 1990). The techniques of the current invention are thus not limited to any particular nucleic acid sequences.

One important use of the sequences provided by the invention will be in the alteration of plant phenotypes by genetic transformation with sense or antisense flavonoid and/or isoflavonoid biosynthesis genes. The flavonoid and/or isoflavonoid biosynthesis gene may be provided with other sequences. Where an expressible coding region that is not necessarily a marker coding region is employed in combination with a marker coding region, one may employ the separate coding regions on either the same or different DNA segments for transformation. In the latter case, the different vectors are delivered concurrently to recipient cells to maximize cotransformation.

The choice of any additional elements used in conjunction with the flavonoid and/or isoflavonoid biosynthesis coding sequences will often depend on the purpose of the transformation. One of the major purposes of transformation of crop plants is to add commercially desirable, agronomically important traits to the plant. As isoflavonoids are known to confer many beneficial effects on health, one such trait is increased biosynthesis of isoflavonoids. Concomitant increases in flavonoid production may also be beneficial and could be achieved by increasing expression of precursors of flavonoid and isoflavonoid compounds. Alternatively, plants may be engineered to decrease synthesis of flavonoids and/or isoflavonoids.

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce genes corresponding to the entire flavonoid and/or isoflavonoid biosynthetic pathway into a plant. Introduction of such sequences may be facilitated by use of bacterial or yeast artificial chromosomes (BACs or YACs, respectively), or even plant artificial chromosomes. For example, the use of BACs for *Agrobacterium*-mediated transformation was disclosed by Hamilton et al. (1996).

Particularly useful for transformation are expression cassettes which have been isolated from such vectors. DNA segments used for transforming plant cells will, of course, generally comprise the cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. However, this may not always be the case, and the present invention also encompasses transgenic plants incorporating non-expressed transgenes. Preferred components likely to be included with vectors used in the current invention are as follows.

A. Regulatory Elements

Exemplary promoters for expression of a nucleic acid sequence include plant promoter such as the CaMV 35S promoter (Odell et al., 1985), or others such as CaMV 19S (Lawton et al., 1987), nos (Ebert et al., 1987), Adh (Walker et al., 1987), sucrose synthase (Yang & Russell, 1990), a-tubulin, actin (Wang et al., 1992), cab (Sullivan et al., 1989), PEPCase (Hudspeth and Grula, 1989) or those associated with the R gene complex (Chandler et al., 1989). Tissue specific promoters such as root cell promoters (Conkling et al., 1990) and tissue specific enhancers (Fromm et al., 1986) are also contemplated to be particularly useful, as are inducible promoters such as ABA- and turgor-inducible promoters. In one embodiment of the invention, the native promoter of a flavonoid and/or isoflavonoid biosynthesis gene is used.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

It is contemplated that vectors for use in accordance with the present invention may be constructed to include the ocs enhancer element. This element was first identified as a 16 bp palindromic enhancer from the octopine synthase (ocs) gene of *Agrobacterium* (Ellis et al., 1987), and is present in at least 10 other promoters (Bouchez et al., 1989). It is proposed that the use of an enhancer element, such as the ocs element and particularly multiple copies of the element, will act to increase the level of transcription from adjacent promoters when applied in the context of plant transformation.

It is specifically envisioned that flavonoid and/or isoflavonoid biosynthesis coding sequences may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue; a truncated (−90 to +8) 35S promoter which directs enhanced expression in roots, and an a-tubulin gene that also directs expression in roots.

B. Terminators

Transformation constructs prepared in accordance with the invention will typically include a 3' end DNA sequence that acts as a signal to terminate transcription and allow for the poly-adenylation of the mRNA produced by coding sequences operably linked to a flavonoid and/or isoflavonoid biosynthesis gene. In one embodiment of the invention, the native terminator of a flavonoid and/or isoflavonoid biosynthesis gene is used. Alternatively, a heterologous 3' end may enhance the expression of sense or antisense flavonoid and/or isoflavonoid biosynthesis genes. Terminators which are deemed to be particularly useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

D. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms selectable or screenable markers also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154,204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase (Murakami et al., 1986; Twell et al., 1989), causing rapid accumulation of ammonia and cell death.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; an aequorin gene (Prasher et al., 1985) which may be employed in calcium-sensitive bioluminescence detection; or a gene encoding for green fluorescent protein (Sheen et al., 1995; Haseloff et al., 1997; Reichel et al., 1996; Tian et al., 1997; WO 97/41228).

Another screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It also is envisioned that this system may be developed for populational screening for bioluminescence, such as on tissue culture plates, or even for whole plant screening. The gene which encodes green fluorescent protein (GFP) is also contemplated as a particularly useful reporter gene (Sheen et al., 1995; Haseloff et al., 1997; Reichel et al., 1996; Tian et al., 1997; WO 97/41228). Expression of green fluorescent protein may be visualized in a cell or plant as fluorescence following illumination by particular wavelengths of light.

II. Antisense Constructs

Antisense treatments represent one way of altering flavonoid and/or isoflavonoid biosynthesis in accordance with the invention. In one embodiment of the invention, constructs comprising an antisense flavanone 3-hydroxylase sequence may be used to increase isoflavone production and accumulation in plants by decreasing or effectively eliminating flavanone 3-hydroxylase activity in a plant. Accordingly, this may be used to increase anthocyanin accumulation in a plant or given plant tissue. As such, antisense technology may be used to "knock-out" the function of a flavanone 3-hydroxylase gene or another flavonoid and/or isoflavonoid biosynthesis gene or homologous sequences thereof.

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see above) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

III. Tissue Cultures

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Nutrient media is prepared as a liquid, but this may be solidified by adding the liquid to materials capable of providing a solid support. Agar is most commonly used for this purpose. Bactoagar, Hazelton agar, Gelrite, and Gelgro are specific types of solid support that are suitable for growth of plant cells in tissue culture.

Some cell types will grow and divide either in liquid suspension or on solid media. As disclosed herein, plant cells will grow in suspension or on solid medium, but regeneration of plants from suspension cultures typically requires transfer from liquid to solid media at some point in development. The type and extent of differentiation of cells in culture will be affected not only by the type of media used and by the environment, for example, pH, but also by whether media is solid or liquid.

Tissue that can be grown in a culture includes meristem cells, Type I, Type II, and Type III callus, immature embryos and gametic cells such as microspores, pollen, sperm and egg cells. Type I, Type II, and Type III callus may be initiated from tissue sources including, but not limited to, immature embryos, seedling apical meristems, root, leaf, microspores and the like. Those cells which are capable of proliferating as callus also are recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population. For example, Type II callus development, followed by manual selection and culture of friable, embryogenic tissue, generally results in an enrichment of cells. Manual selection techniques which can be employed to select target cells may include, e.g., assessing cell morphology and differentiation, or may use various physical or biological means. Cryopreservation also is a possible method of selecting for recipient cells.

Manual selection of recipient cells, e.g., by selecting embryogenic cells from the surface of a Type II callus, is one means that may be used in an attempt to enrich for particular cells prior to culturing (whether cultured on solid media or in suspension).

Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components, but may differ in the composition and proportions of their ingredients depending on the particular application envisioned. For example, various cell types usually grow in more than one type of media, but will exhibit different growth rates and different morphologies, depending on the growth media. In some media, cells survive but do not divide. Various types of media suitable for culture of plant cells previously have been described. Examples of these media include, but are not limited to, the N6 medium described by Chu et al.,(1975) and MS media (Murashige and Skoog, 1962).

IV. Methods for Genetic Transformation

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by *Agrobacterium*-mediated transformation (U.S. Pat. No. 5,591,616 and 5,563,055; both specifically incorporated herein by reference) and by acceleration of DNA coated particles (U.S. Pat. No. 5,550,318; 5,538,877; and 5,538,880; each specifically incorporated herein by reference in its entirety), etc. Through the application of techniques such as these, the cells of virtually any plant species may be stably transformed, and these cells developed into transgenic plants.

A. *Agrobacterium*-Mediated Transformation

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

*Agrobacterium*-mediated transformation is most efficient in dicotyledonous plants and is the preferable method for transformation of dicots, including *Arabidopsis*, tobacco, tomato, alfalfa and potato. Indeed, while *Agrobacterium*-mediated transformation has been routinely used with dicotyledonous plants for a number of years, it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al., 1998), alfalfa (Thomas et al., 1990) and maize (Ishidia et al., 1996).

Modem *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

B. Electroporation

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

C. Microprojectile Bombardment

Another method for delivering transforming DNA segments to plant cells in accordance with the invention is microprojectile bombardment (U.S. Pat. No. 5,550,318; 5,538,880; 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al., 1994), peanut (Singsit et al., 1997), cotton (McCabe and Martinell, 1993), tomato (VanEck et al., 1995), and legumes in general (U.S. Pat. No. 5,563,055, specifically incorporated herein by reference in its entirety).

D. Other Transformation Methods

Transformation of protoplasts can be achieved using methods based on calcium phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts have been described (Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cells are punctured. This technique has been used successfully with, for example, the monocot cereals maize (PCT Application WO 95/06128, specifically incorporated herein by reference in its entirety; (Thompson, 1995) and rice (Nagatani, 1997).

V. Production and Characterization of Stably Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

A. Selection

It is believed that DNA is introduced into only a small percentage of target cells in any one experiment. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphostransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus Streptomyces also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*. In the bacterial source organism, this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato, potato (De Block et al., 1987) *Brassica* (De Block et al., 1989) and maize (U.S. Pat. No. 5,550,318). In previous reports, some transgenic plants which expressed the resistance gene were completely resistant to commercial formulations of PPT and bialaphos in greenhouses.

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103. The best characterized mutant EPSPS gene conferring glyphosate resistance comprises amino acid changes at residues 102 and 106, although it is anticipated that other mutations will also be useful (PCT/WO97/4103).

To use the bar-bialaphos or the EPSPS-glyphosate selective system, transformed tissue is cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate will typically be preferred, it is proposed that ranges of 0.1-50 mg/l bialaphos or 0.1-50 mM glyphosate will find utility.

It further is contemplated that the herbicide DALAPON, 2,2-dichloropropionic acid, may be useful for identification of transformed cells. The enzyme 2,2-dichloropropionic acid dehalogenase (deh) inactivates the herbicidal activity of 2,2-dichloropropionic acid and therefore confers herbicidal resistance on cells or plants expressing a gene encoding the dehalogenase enzyme (Buchanan-Wollaston et al., 1992; U.S. Pat. No. 5,508,468; and 5,508,468; each of the disclosures of which is specifically incorporated herein by reference in its entirety).

Alternatively, a gene encoding anthranilate synthase, which confers resistance to certain amino acid analogs, e.g., 5-methyltryptophan or 6-methyl anthranilate, may be useful as a selectable marker gene. The use of an anthranilate synthase gene as a selectable marker was described in U.S. Pat. No. 5,508,468.

An example of a screenable marker trait is the enzyme luciferase. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. These assays are nondestructive and transformed cells may be cultured further following identification. The photon counting camera is especially valuable as it allows one to identify specific cells or groups of cells which are expressing luciferase and manipulate those in real time. Another screenable marker which may be used in a similar fashion is the gene coding for green fluorescent protein.

It further is contemplated that combinations of screenable and selectable markers will be useful for identification of transformed cells. In some cell or tissue types a selection agent, such as bialaphos or glyphosate, may either not provide enough killing activity to clearly recognize transformed cells or may cause substantial nonselective inhibition of transformants and nontransformants alike, thus causing the selection technique to not be effective. It is proposed that selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. It is proposed that combinations of selection and screening may enable one to identify transformants in a wider variety of cell and tissue types. This may be efficiently achieved using a gene fusion between a selectable marker gene and a screenable marker gene, for example, between an NPTII gene and a GFP gene.

B. Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soiless plant growth mix, and hardened, e.g., in an environmentally controlled chamber, for example, at about 85% relative humidity, 600 ppm $CO_2$, and 25-250 microeinsteins $m^{-2}$ $s^{-1}$ of light. Plants are preferably matured either in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants are preferably grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with $10^{-5}$M abscisic acid and then transferred to growth regulator-free medium for germination.

C. Characterization

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

D. DNA Integration, RNA Expression and Inheritance

Genomic DNA may be isolated from cell lines or any plant parts to determine the presence of the exogenous gene through the use of techniques well known to those skilled in the art. Note, that intact sequences will not always be present, presumably due to rearrangement or deletion of sequences in the cell. The presence of DNA elements introduced through the methods of this invention may be determined, for example, by polymerase chain reaction (PCR™). Using this technique, discreet fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR™ analysis. In addition, it is not typically possible using PCR™ techniques to determine whether transformants have exogenous genes introduced into different sites in the genome, i.e., whether transformants are of independent origin. It is contemplated that using PCR™ techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR™, e.g., the presence of a gene.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot Northern hybridizations. These techniques are modifications of Northern blotting and will only demonstrate the presence or absence of an RNA species.

E. Gene Expression

While Southern blotting and PCR™ may be used to detect the gene(s) in question, they do not provide information as to whether the corresponding protein is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}$C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

VI. Breeding Plants of the Invention

In addition to direct transformation of a particular plant genotype with a construct prepared according to the current invention, transgenic plants may be made by crossing a plant having a selected DNA of the invention to a second plant lacking the construct. Plant breeding techniques may also be used to introduce a transgenic or non-transgenic mutated or defective flavanone 3-hydroxylase into a plant. In this manner, flavanone 3-hydroxylase can be effectively down regulated. By creating plants homozygous for a mutant allele, flavanone 3-hydroxylase activity can be eliminated in the plant.

As set forth above, a selected flavonoid and/or isoflavonoid biosynthesis gene can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes or alleles relative to a starting plant line, as disclosed herein, is defined as the techniques that result in a particular sequence being introduced into a plant line by crossing a starting line with a donor plant line that comprises a transgene or allele of the invention. To achieve this one could, for example, perform the following steps:

(a) plant seeds of the first (starting line) and second (donor plant line that comprises a desired transgene or allele) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking said desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

VII. Nutraceuticals

Nutraceutical compositions are preparations of natural ingredients that are multi-component systems consisting of preferably synergistic natural products and supplements to promote good health. The plants provided by the invention contain increased isoflavonoid content, which has certain health benefits, and thus these plants may be used for the preparation of nutraceutical compositions. Nutraceutical compositions can be derived from plant tissue. Information about numerous plants and herbs that have been used to prepare nutraceutical compositions has been compiled and is available in publications including the *German Commission E Monographs, Botanical Safety Handbook*, and *HerbalGram*, a quarterly publication of the American Botanical Council which references numerous clinical trials that have been performed using nutraceuticals.

Information on description and constituents, modern uses, dosage (in a variety of forms), actions, contraindications, side effects, interactions with conventional drugs, mode of administration, duration of application, regulatory status, AHPA botanical safety rating, and comments are available for a number of plants and include among others bilberry, cascara, cat's claw, cayenne, cranberry, devil's claw, dong quai, echinacea, evening primrose oil, feverfew, garlic, ginger, ginkgo, Asian ginseng, Siberian ginseng, goldenseal, gotu kola, grape seed, green tea, hawthorn, kava, licorice, milk thistle, saw palmetto, St. John's wort, and valerian.

The actions of these nutraceutical compounds may be fast or/and short-term or may help achieve long-term health objectives. Nutraceutical compositions may comprise dried and ground plant tissue or extracts from these tissues in a pharmacologically acceptable medium as a natural approach for treatment of various ailments. The nutraceutical compositions may be contained in a medium such as a buffer, a solvent, a diluent, an inert carrier, an oil, a creme, or an edible material. The nutraceutical may be orally administered and may be in the form of a tablet or a capsule. Alternatively the nutraceutical may be in the form of an ointment which has extracts of plant tissue in an oil or cream which can be topically applied to the skin.

VIII. Definitions

Isoflavone biosynthesis gene: A gene encoding a polypeptide that catalyzes one or more steps in the plant biosynthesis of isoflavones.

Flavanone biosynthesis gene: A gene encoding a polypeptide that catalyzes one or more steps in the plant biosynthesis of flavanones.

Expression: The combination of intracellular processes, including transcription and translation undergone by a coding DNA molecule such as a structural gene to produce a polypeptide.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found In this respect, the sequence may be native to the host genome, but be rearranged with respect to other genetic sequences within the host sequence. For example, a regulatory sequence may be heterologous in that it is linked to a different coding sequence relative to the native regulatory sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an $R_0$ transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

$R_0$ transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce or has introduced into a plant genome by genetic transformation.

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell the DNA complement of which has been altered by the introduction of an exogenous DNA molecule into that cell.

Transgene: A segment of DNA which has been incorporated into a host genome or is capable of autonomous replication in a host cell and is capable of causing the expression of one or more mRNA(s), which may or may not be coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule capable of replication in a host cell and/or to which another DNA segment can be operatively linked so as to bring about replication of the attached segment. A plasmid is an exemplary vector.

IX. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Expression of Soybean CYP93C1v2 in *Arabidopsis thaliana*

The open reading frame of the soybean CYP93C1v2 IFS cDNA (Genbank Accession #AFO22462; SEQ ID NO:1; Steele et al., 1999) was cloned into the binary vector pCHF3, under control of the constitutive cauliflower mosaic virus 35S promoter, as described in PCT/US00/05915. Seedlings of *Arabidopsis thaliana* ecotype Columbia were transformed using a floral vacuum infiltration method (Clough and Bent, 1998) and selected on Petri plates with the antibiotic kanamycin. Resistant seedlings were self pollinated, and resultant $T_2$ progeny subjected to molecular (DNA and RNA gel blot) and phytochemical analysis by standard methodology to verify transformation.

Leaves of *Arabidopsis* plant 15B expressing CYP93C1v2 were extracted in acetone/methanol and analyzed for flavonoid content by HPLC, with effluent monitored by diode array detection. Untransformed *Arabidopsis* leaves contained a series of glycosides of the flavonols kaempferol and quercetin (Graham, 1998), and the identity of these compounds was confirmed by their UV absorption characteristics and shifts in peak positions following pre-treatment of extracts with almond 13-glucosidase. The compounds were shown to correspond to the flavonol rhamnosides and glucorhamnosides previously reported (Graham, 1998). In contrast, corresponding extracts from leaves of *Arabidopsis* expressing CYP93C1v2 contained three extra peaks. All three peaks exhibited UV absorption spectra similar to that of authentic genistein. Following treatment with β-glucosidase, one compound disappeared, and a new peak appeared that co-chromatographed with a sample of authentic genistein, indicating that this compound is a β-glucoside of genistein. The other two new compounds were conjugates in which a sugar other than glucose is directly linked to the isoflavone.

LC/MS was used for further identification of the genistein conjugates found in the transgenic *Arabidopsis*. The results identified the compounds as glucose-genistein, glucose-rhamnose-genistein, and rhamnose-genistein. Although MS analysis clearly identified the molecular weights of the sugars conjugated to the genistein, it did not reveal the position of attachment, which could be at position 7 (the most likely, based on the common structures of other flavonoid and isoflavonoid glycosides), 5, or 4'. Isoflavones with a free 7-hydroxyl group exhibit bathochromic shifts following ionization of this hydroxyl group in the presence of sodium acetate (Mabry, 1970). In the case of genistein, there is a 10 nm shift of the absorption maximum to a higher wavelength, whereas genistin (7-O-glucosyl genistein) does not exhibit such a shift. No shifts in absorption maxima were observed for the genistein conjugates following treatment with sodium acetate, confirming the expected linkage of the Feeding isoflavones to plant cell cultures can result in their incorporation into the insoluble cell wall fraction (Park, 1995). To determine whether *Arabidopsis* could similarly metabolize the introduced foreign isoflavone genistein, cell walls were prepared, the phenolic fraction was liberated by alkaline hydrolysis, and the components were analyzed by HPLC. The analyses revealed several wall-bound hydroxycinnamic acids, including ferulic acid, to be present in equal amounts in empty vector and CYP93C1v2 transformants. However, there was no evidence for the presence of genistein in the cell wall fraction from the CYP93C1v2 transformants.

Free isoflavones rarely accumulate constitutively in plants; they are usually present as glucosides and malonyl glucosides in legumes (Graham, 1990; Park et al., 1992; Sumner et al., 1996). Likewise, *Arabidopsis* glycosylates the introduced genistein, presumably using the same glycosyl transferases that are involved in conjugation of the plant's natural flavonoid end products, the flavonols kaempferol and quercetin. Studies on uptake of dietary genistein have suggested that the free aglycone is highly bioavailable (Sfakianos et al., 1997), and isoflavone glycosides are hydrolyzed to the aglycones by lactobacilli, *Bacteroides* and *Bifidobacteria* in the intestinal flora. Glycosylation is, therefore, a favorable trait for engineered nutraceutical products, as it results in their storage in the vacuole, away from further potential metabolism, in a form that does not compromise bioavailability.

Example 2

Expression of alfalfa CHI in *Arabidopsis thaliana*

The open reading frame of the alfalfa chalcone isomerase MSCHI1 cDNA (Genbank Accession # M91079; SEQ ID NO:3; McKhann and Hirsch, 1994) was cloned into the binary vector pCHF3, under control of the constitutive cauliflower mosaic virus 35S promoter. Seedlings of *Arabidopsis thaliana* ecotype Columbia were transformed using a floral vacuum infiltration method (Clough and Bent, 1998), and selected on Petri plates with the antibiotic kanamycin. Resistant seedlings were self pollinated, and resultant $T_2$ progeny subjected to molecular and phytochemical analysis by methods known in the art to verify transformation.

Figures 2A, 2B:
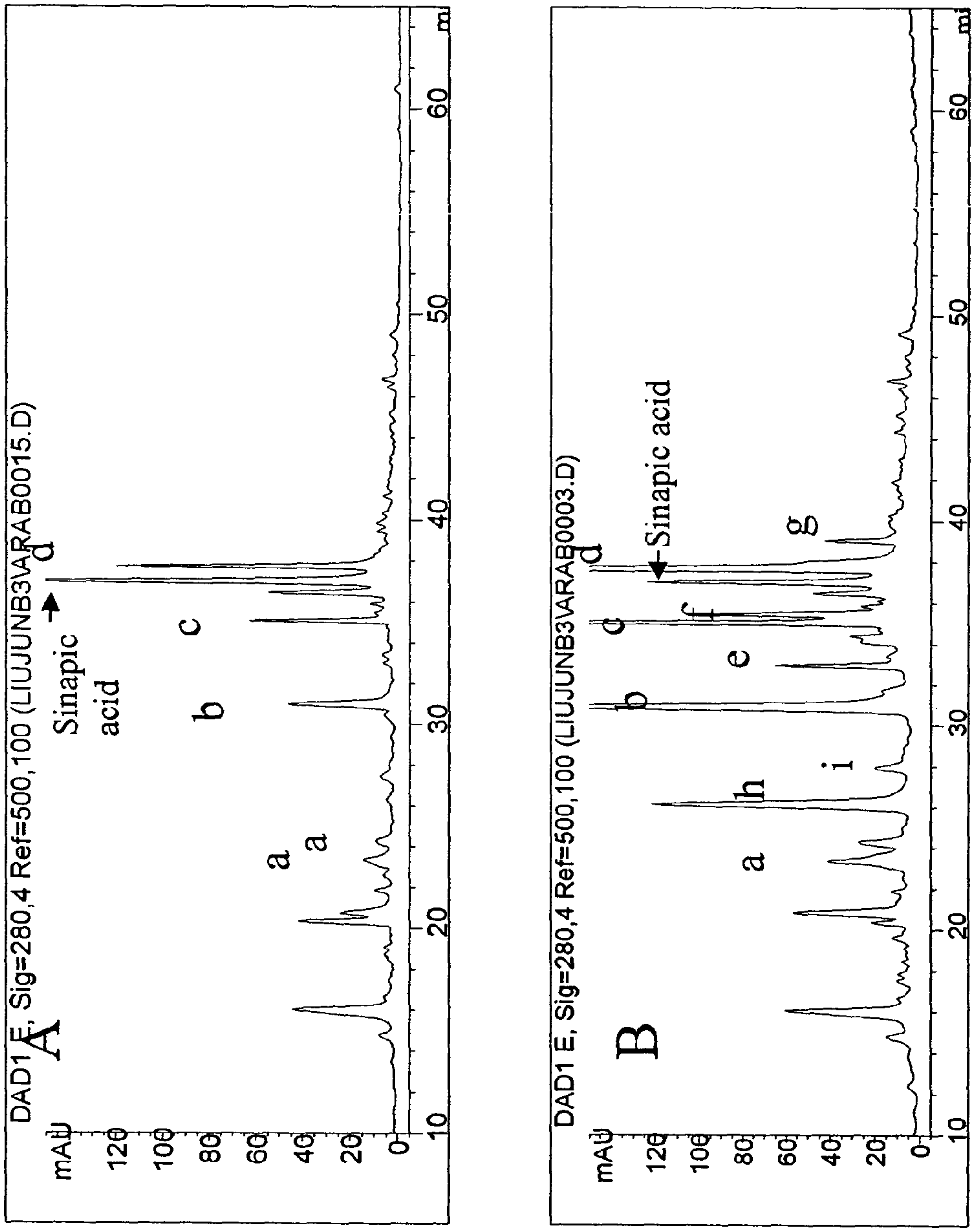
FIGS. 2A-2D: Depicts HPLC profiles of flavonoids from leaf extracts of wild-type (A) and alfalfa CHI-expressing (B) *Arabidopsis*. Profiles of flavonoids from wild-type (C) and alfalfa CHI-expressing (D) *Arabidopsis* leaves are shown following digestion of the extracts with β-glucosidase. The compounds are: a, Rha-Gluc-Rha-quercetin; b, Rha-Gluc-Rha-kaempferol; c, Rha-Rha-quercetin; d, Rha-Rha-kaempferol; e, Gluc-Rha-quercetin; f, Rutin; g, h and i, unknown quercetin conjugates; l, kaempferol conjugate; n, kaempferol; j, k and m, quercetin conjugates.
Figures 2C, 2D:
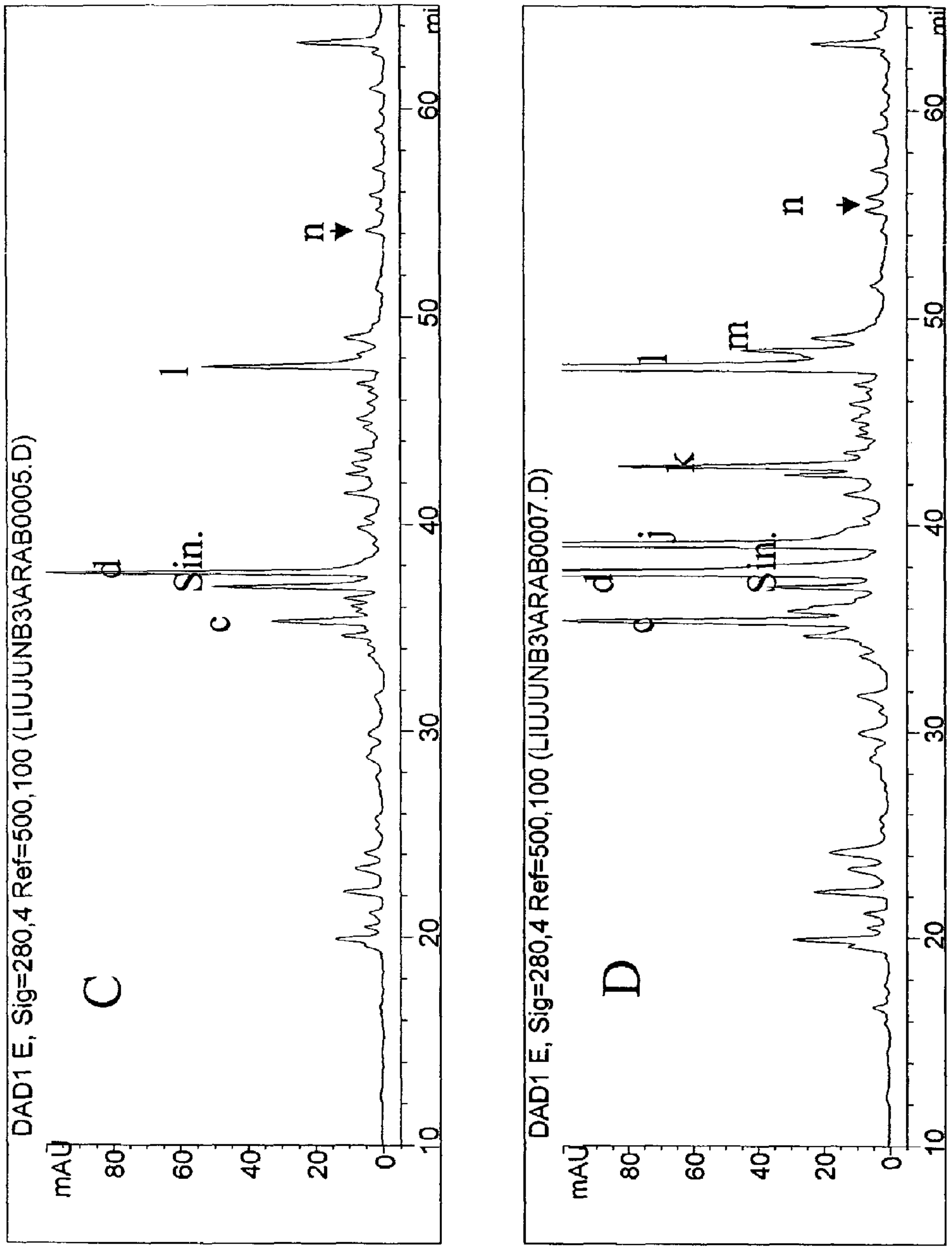

CHI transformants were analyzed for alfalfa CHI transcript levels by RNA gel blot analysis. Six independent lines had very high expression, and four further lines exhibited low to moderate expression. The highest expressing line, named 4-11, and two other strongly expressing lines, 4-9 and 4-25, were used for further analysis. Leaves of the three *Arabidopsis* lines expressing alfalfa CHI were sequentially extracted in acetone and acetone/methanol (1:1) and analyzed for flavonoid content by HPLC, with effluent monitored by diode array detection. FIG. 2A shows HPLC traces of non-hydrolyzed leaf extracts from a control line, showing the presence of a number of rhamnose and/or glucose conjugates of kaempferol and quercetin. FIG. 2B shows a corresponding trace from CHI over-expressing line 4-11. Levels of several of the kaempferol and quercetin conjugates identified in FIG. 2A were strongly elevated, and a number of new peaks were observed. The new compounds were identified as conjugates of quercetin; glucose-rhamnose-quercetin, and three other conjugates in which the sugars were not identified. FIGS. 2C and 2D show traces from the same tissue samples following 13-glucosidase digestion of the leaf extracts. Peaks a, b, e, f and g in FIGS. 2A and 2B have disappeared, and new peaks (j-n) have appeared, confirming the presence of β-glucose linkages in peaks a, b, e, f and g.

Table 1 summarizes the levels of the various kaempferol and quercetin conjugates in control *Arabidopsis* and the three alfalfa CHI over-expressing lines: 4-9, 4-11 and 4-25. For the analysis, 4 g fresh weight of leaves was extracted twice with iced acetone and acetone: methanol (1:1) sequentially, concentrated extracts were dissolved in 3 ml methanol, 20 μl of extract was injected for HPLC analysis. Over-expression of CHI resulted in an approximately 4-fold to 7-fold increase in total kaempferol and quercetin conjugates. Thus, genetic manipulation leading to over-expression of CHI results in large increases in the levels of antioxidant flavonoid derivatives in transgenic plants.

TABLE 1

Levels of flavonols in transgenic Arabidopsis lines expressing alfalfa CHI*

| Lines | RGRQ | RRQ. | GRQ | Rutin | Q conjug. | RGRK | RRK | K cpnjug. | Total (μg/g F>W>) |
|---|---|---|---|---|---|---|---|---|---|
| Ctrl. | 4.4 | 8.7 | — | — | — | 15.3 | 29.1 | — | 57.4 |
| 4-9 | 20.4 | 27.3 | 8.9 | 17.4 | 18.5 | 51.6 | 94.4 | 8.2 | 246.7 |
| 4-11 | 13.8 | 53.0 | 15.6 | 27.9 | 73.8 | 71.1 | 129.5 | 12.2 | 396.8 |
| 4-25 | 13.7 | 40.9 | 15.9 | 34.0 | 25.6 | 64.6 | 118.3 | 17.6 | 330.6 |

*R = rhamnose, G = glucose, Q = quercetin, K = kaempferol.

Example 3

Figures 3A, 3B, 3C, 3D:
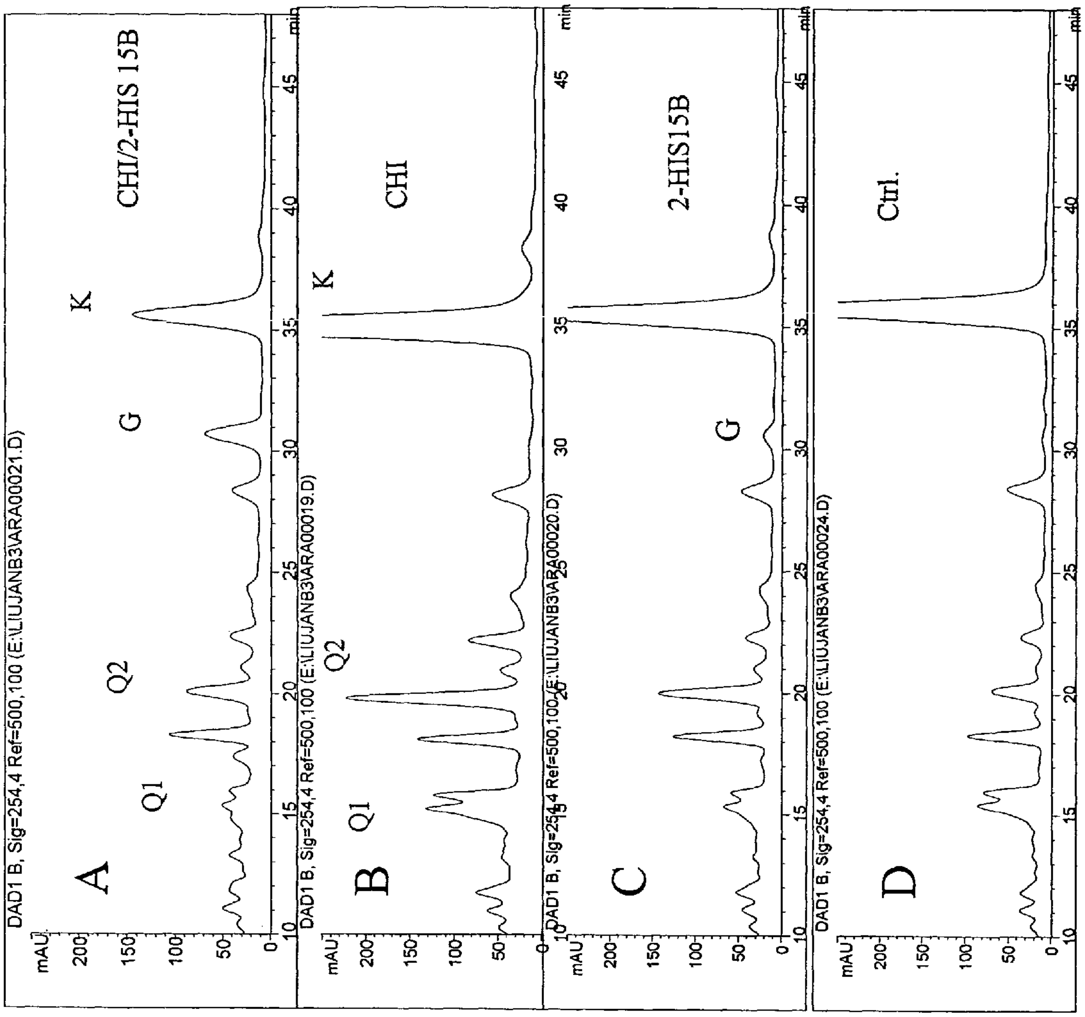
FIGS. 3A-3D: Depicts HPLC profiles of flavonoids/isoflavonoids in *Arabidopsis* leaves of a wild-type (Ctr1) plant, or plants expressing soybean IFS (2-HIS 15b), alfalfa CHI (CHI) or progeny of a cross expressing both IFS and CHI (CHI/2-HIS 15b). Leaf extracts were hydrolyzed with HCl prior to chromatography. Compounds were quercetin and a quercetin derivative (Q1, Q2), kaempferol (K), and genistein (G).

Flavonoid/isoflavonoid Production in Transgenic *Arabidopsis* Expressing Both Soybean CYP93C1v2 and Alfalfa CHI To test whether increasing flux into flavonoid biosynthesis by expression of alfalfa CHI would result in a corresponding increase in genistein production, IFS transgenic line 15b was crossed with line 4-11 harboring the alfalfa CHI transgene, and $F_2$ progeny plants screened for retention of IFS and CHI transgenes by PCR. Positive progeny were then analyzed by HPLC for content of genistein (after hydrolysis of leaf extracts) and flavonols. Homozygous 15b and 4-11 plants ($T_4$ generation) were included for comparison. FIG. 3A-3D show HPLC traces of leaf extracts from control (Ctrl; FIG. 3D), CHI 4-11 transgenic (CHI; FIG. 3B), IFS 15B transgenic (2-HIS15B; FIG. 3C), and CHI/IFS transgenic (CHI/2-HIS15b; FIG. 3A) progeny *Arabidopsis* plants. The extracts had been subjected to acid hydrolysis in order to hydrolyze all sugar conjugates and thereby simplify the HPLC traces. The results confirmed the elevated levels of kaempferol and quercetin in line 4-11 as compared to control plants, and the production of low levels of genistein in the IFS 15b line. One of the $F_2$ progeny lines expressing both transgenes appeared to contained higher levels of genistein than did 15b $T_4$ plants (Table 2). However, two F2 progeny of the cross contained lower flavonol levels than did line 4-11.

Figures 4A, 4B, 4C, 4D, 4E, 4F:
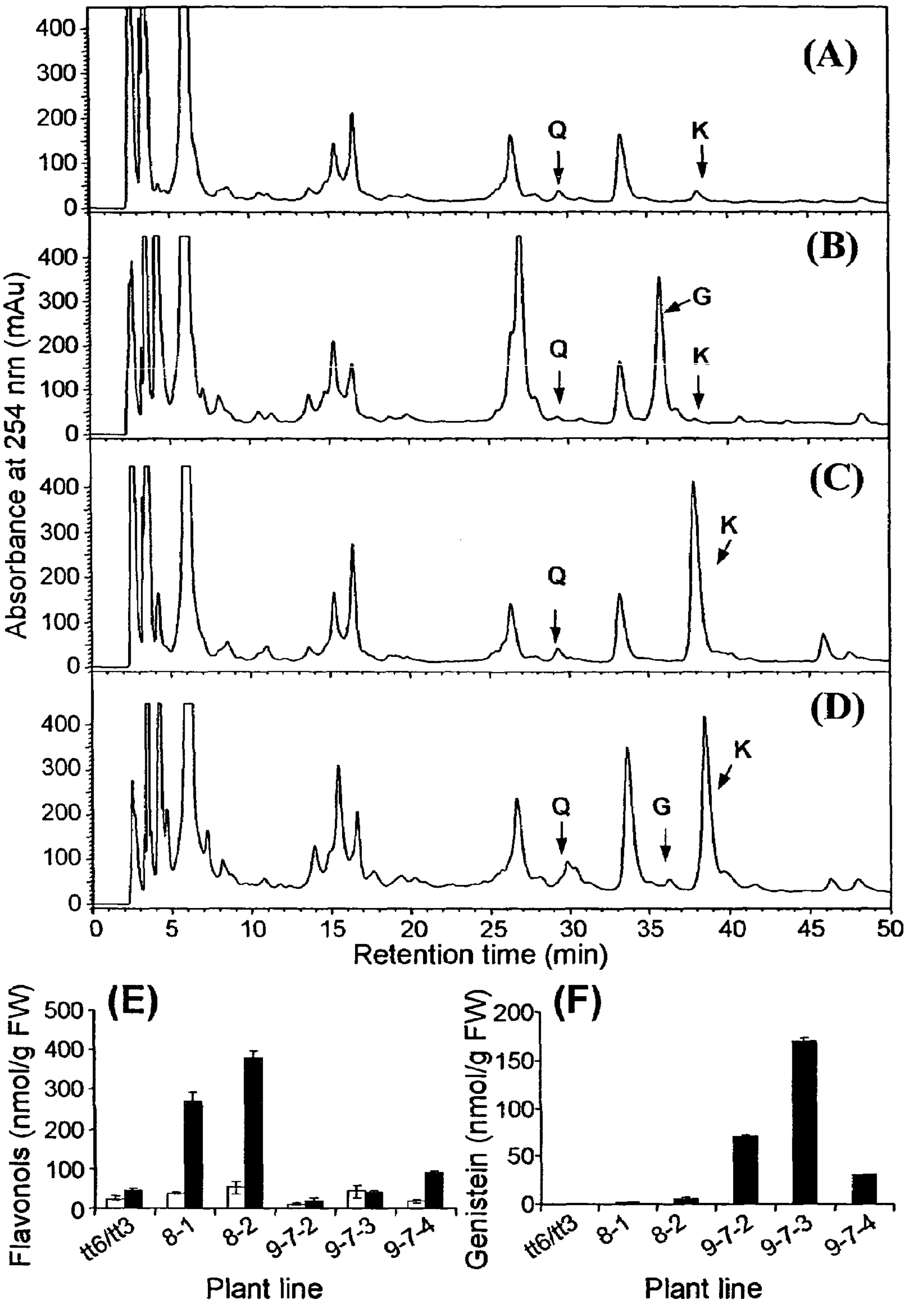
FIGS. 4A-4D: Depicts HPLC profiles of hydrolyzed extracts from leaves of the *Arabidopsis* tt6/tt3 mutant and wild-type Landsberg Erecta (Ler) with and without expression of soybean IFS ($T_3$ generation). (A) tt6/tt3. (B) tt6/tt3 expressing IFS. (C) Ler wild-type. (D) Ler expressing IFS. The compounds are: G, genistein; K, kaempferol; Q, quercetin.
FIG. 4E-4F depicts levels of flavonols (E) and genistein (F) in individual $T_3$ plants of Ler (8-designations) and tt6/tt3 (9-designations) expressing IFS. Open bars, quercetin; filled bars, kaempferol.

A larger number of $F_3$ progeny plants were next examined for isoflavone and flavonol levels, and CHI transgene product activity. The results confirmed the reduction in flavonol levels in plants producing genistein (Table 2). For most $F_3$ lines, levels of flavonol conjugates were between 13 and 70% of the average value for the 4-11 line. However, the data failed to confirm a relation between high genistein levels and elevated CHI activity. Two lines with highest genistein levels (3-3-1 and 3-4-1) had lost the CHI transgene through segregation, as determined by both PCR and the total lack of enzyme activity of crude extracts when supplied with isoliquiritigenin as substrate (Table 2). Furthermore, for the $F_3$ progeny that had retained both transgenes, genistein levels were, overall, no higher than in line 15b. Therefore, although over-expression of CHI results in increased flavonol production in *Arabidopsis*, the increase in flux through naringenin does not result in increased isoflavone production, and isoflavone accumulation appears to cause a disproportionate decrease in flavonol levels in CHI over-expressing plants. This suggests competition and interference between the flavonol and isoflavone pathways.

genistein, similar to those in the Col-0 background (FIGS. 4D, 4F). However, tt6/tt3 expressing IFS produced much greater amounts of genistein, with levels from 31-169 nmol/g fresh wt in three $T_3$ progeny plants (FIGS. 4B, F).

*Arabidopsis thaliana* is a member of the cruciferae, and therefore related to a number of vegetable and oil crops such as cabbage, sprouts, cauliflower, mustard and oil seed rape. Crucifers themselves contain health-promoting compounds such as certain glucosinolates (Faulkner et al., 1998), and such species can be made even more "healthy" by incorporation of genes leading to accumulation of isoflavones. The results described herein provide proof of principle for a metabolic engineering strategy that should find wide usage in vegetable, grain and fruit species.

Example 5

Expression of *Medicago truncatula* IFS in alfalfa

The open-reading frame of *Medicago truncatula* IFS (MtIFS, TC45136) was cloned into the binary vector pCAMBIA 2300 under control of the double cauliflower mosaic virus 35S promoter. This vector was transformed into alfalfa

TABLE 2

Genistein and flavonol levels in individual progeny of transgenic Arabidopsis expressing soybean IFS and/or alfalfa CHI*

| Line | Generation | Alfalfa CHI activity (nmol/min/mg) | Quercetin (nmol/g FW) | Kaempferol (nmol/g FW) | Total flavonols (nmol/g FW) | Genistein (nmol/g FW) |
|---|---|---|---|---|---|---|
| Wild-type | $T_4$ | 0 | 32.4 ± 5.9 | 285.8 ± 35.7 | 318.2 ± 36.7 | 0 |
| CHI 4-11 | $T_4$ | 49.6 ± 3.0 | 79.6 ± 16.4 | 475.3 ± 77.8 | 555.0 ± 84.5 | 0 |
| IFS 15b | $T_4$ | 0 | 29.4 ± 7.3 | 162.7 ± 37.4 | 192.1 ± 43.9 | 11.9 ± 1.9 |
| IFS/CHI-1 | $F_2$ | ND[b] | 77.1 ± 11.2 | 247.9 ± 60.5 | 325.0 ± 70.7 | 43.9 ± 1.3 |
| IFS/CHI-2 | $F_2$ | ND | 23.0 ± 9.1 | 216.5 ± 50.8 | 239.5 ± 56.4 | 9.6 ± 3.1 |
| IFS/CHI-3 | $F_2$ | ND | 89.7 ± 8.4 | 503.6 ± 48.8 | 593.3 ± 57.2 | 9.0 ± 1.8 |
| IFS/CHI 3-2-1 | $F_3$ | 38.8 ± 2.3 | 65.4 ± 5.8 | 334.9 ± 21.9 | 400.3 ± 27.6 | 11.3 ± 2.7 |
| IFS/CHI 3-2-2 | $F_3$ | 42.6 ± 1.9 | 38.2 ± 6.2 | 297.0 ± 7.4 | 335.2 ± 13.2 | 10.7 ± 1.5 |
| IFS/CHI 3-2-3 | $F_3$ | 35.2 ± 1.7 | 12.8 ± 5.2 | 67.9 ± 6.8 | 80.7 ± 1.7 | 5.7 ± 1.2 |
| IFS/CHI 3-3-1 | $F_3$ | 0 | 35.9 ± 3.6 | 81.4 ± 9.6 | 117.2 ± 12.5 | 19.4 ± 2.4 |
| IFS/CHI 3-4-1 | $F_3$ | 0 | 21.4 ± 4.1 | 75.0 ± 11.9 | 96.4 ± 11.3 | 17.6 ± 0.4 |
| IFS/CHI 3-4-2 | $F_3$ | 46.5 ± 1.0 | 40.7 ± 4.3 | 205.3 ± 17.5 | 246.0 ± 21.7 | 16.4 ± 0.3 |
| IFS/CHI 3-4-3 | $F_3$ | 52.6 ± 1.6 | 49.9 ± 7.1 | 311.5 ± 9.1 | 361.4 ± 13.3 | 13.5 ± 2.5 |
| IFS/CHI 3-4-4 | $F_3$ | 43.8 ± 0.6 | 31.4 ± 2.6 | 251.0 ± 6.4 | 282.4 ± 7.8 | 8.2 ± 1.6 |
| IFS/CHI 3-5-1 | $F_3$ | 63.6 ± 1.3 | 77.3 ± 8.4 | 672.3 ± 8.6 | 749.6 ± 17 | 7.0 ± 0.8 |

*For the analysis, plants were grown under 12 hr light/12 hr dark, ~150 μE light intensity, for 35 days. Data for $T_4$ plants are means ± SE from at least five replicate plants with 2-3 independent analyses for each plant. Data for individual $F_2$ and $F_3$ progeny represent triplicate analyses. ND, not determined.

Example 4

Production of Genistein in the tt3/tt6 Mutant

The tt3/tt6 double mutant of *Arabidopsis* is impaired in expression of both flavanone 3-13-hydroxylase (F3H), the entry point enzyme for flavonol/anthocyanin synthesis, and the downstream enzyme dihydroflavonol reductase (DFR) (Winkel-Shirley, 2001). tt6/tt3 is in ecotype Landsberg Erecta. Soybean IFS was transformed into both wild-type Landsberg and tt6/tt3 to determine the effects of a blockage in flavonol synthesis on genistein production. One confirmed transgenic tt6/tt3 line was taken to the $T_3$ generation, and levels of flavonols and genistein determined by HPLC (FIG. 4B). Surprisingly, both kaempferol and quercetin were detected in all tt6/tt3 lines, although, in the case of kaempferol, at levels at least one order of magnitude less than in wild-type Landsberg (FIGS. 4A, 4B, 4E). Expression of IFS in wild-type Landsberg resulted in low levels of Regen SY-4D (Bingham, 1991) by *Agrobacterium*-mediated transformation of leaf discs according to standard procedures. Transgenic plants were obtained following somatic embryogenesis. Plants were subjected to PCR, DNA gel blot analysis, and RNA gel blot analysis to verify transformation.

Figures 5A, 5B, 5C:
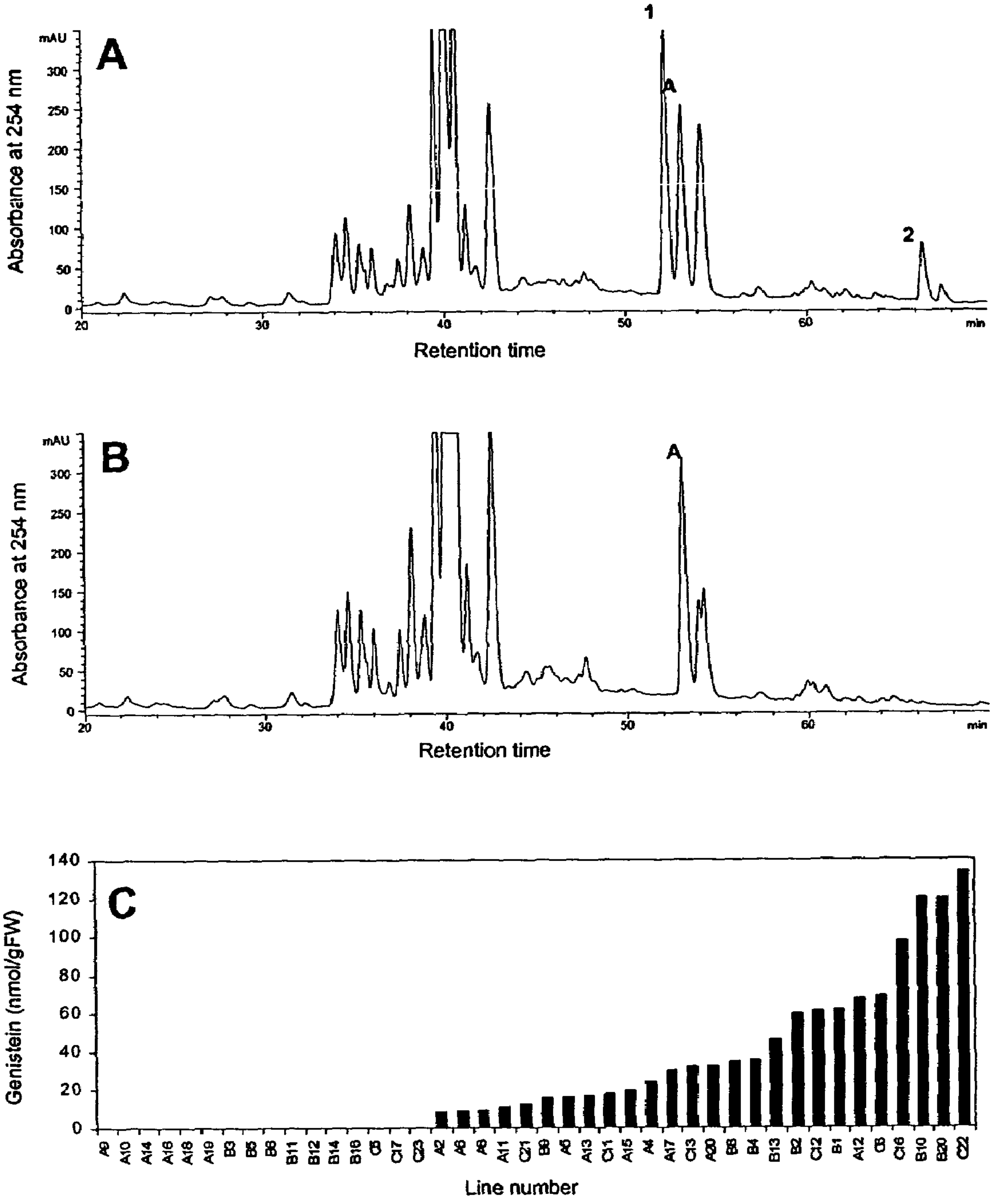
FIGS. 5A-C: Depicts HPLC traces of acid-hydrolyzed leaf extracts from MtIFS-overexpressing line C22 (A) and vector control line C11 (B). Peaks 1 and 2 were not observed in control lines and were identified as genistein and biochanin A, respectively by comparing UV spectra and retention times to authentic standards and by LC-MS analysis. The peak labeled A was identified as apigenin. (C) Depicts the amount of genistein present in leaf extracts of 42 independent MtIFS-overexpressing lines.

Leaves of transgenic alfalfa plants were extracted in 80% methanol and analyzed for flavonoid content by HPLC (FIG. 5). To simplify the analysis, extracts were acid-treated to hydrolyze flavonoids to their aglycones. Control plants transformed with the "empty" binary vector were found to accumulate the flavone apigenin but no isoflavonoids were detected (FIG. 5A). Extracts of plants expressing MtIFS contained two additional peaks, which were identified as genistein and biochanin A by comparing UV spectra and retention times to authentic standards and by LC-MS analysis (FIG. 5B). Genistein levels were found to vary from 0-133 nmol/g FW in the leaves of 42 independent MtIFS-overexpressing lines (FIG. 5C).

Figures 6A, 6B, 6C, 6D, 6E, 6F:
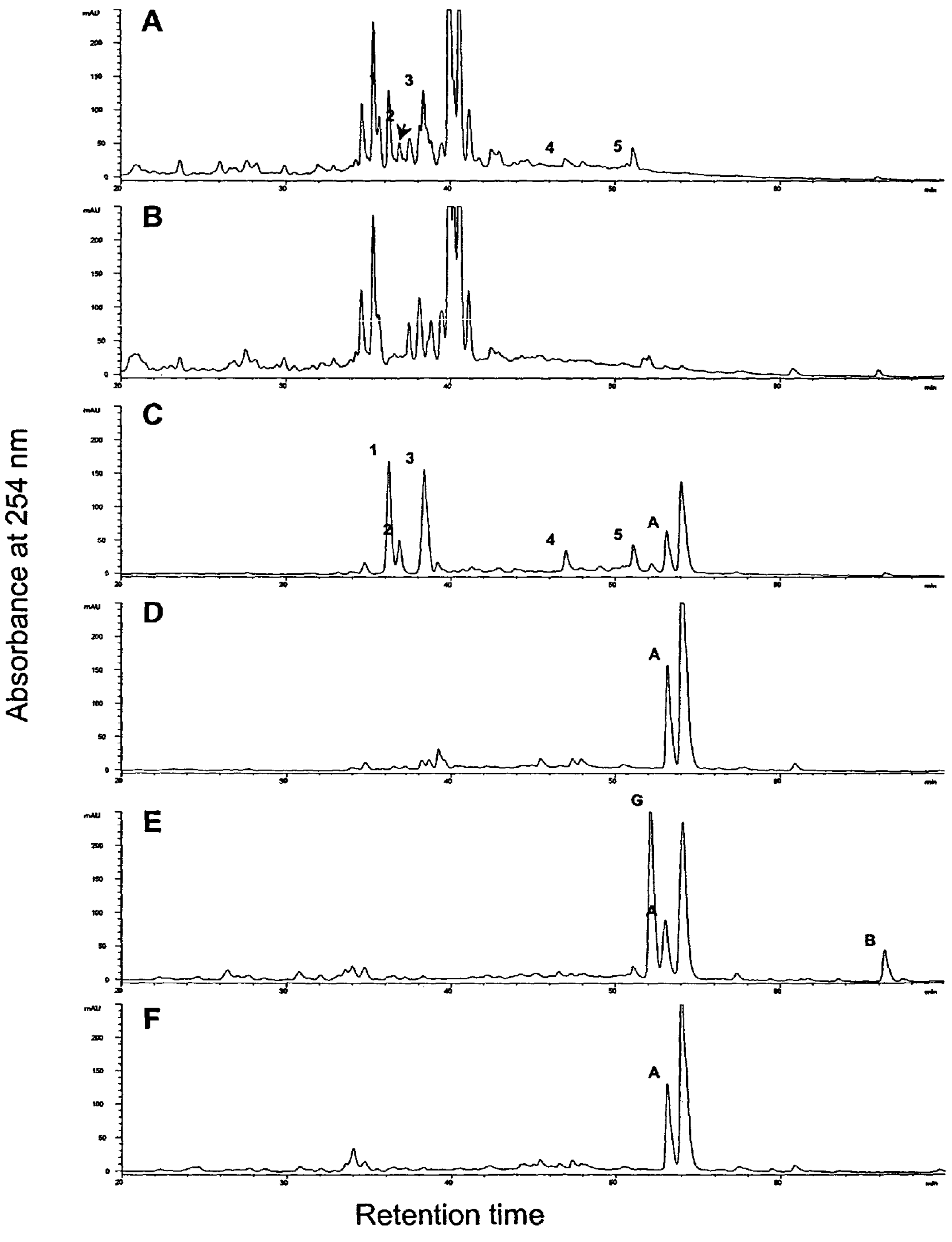
FIGS. 6A-F: Depicts HPLC traces of unhydrolyzed leaf extracts of MtIFS-overexpressing line C22 (A) and vector control line C11 (B). Peaks with UV spectra similar to genistein and not present in the control extracts are numbered 1-5. (C-D) Depicts HPLC traces of leaf extracts of line C22 (C) and control line C11 (D) after digestion with β-glucuronidase. Peaks 1 and 4 were identified as glucose-genistein and glucose-biochanin A, respectively by LC-MS analysis. The peak labeled A was identified as apigenin. (E-F) Depicts HPLC traces of leaf extracts of line C22 (E) and control line C11 (F) after digestion with β-glucosidase. This enzyme preparation also contained significant β-glucuronidase activity. Peaks labeled G and B were identified as genistein and biochanin A, respectively.

In unhydrolyzed leaf extracts no free genistein or biochanin A was detected, but at least 5 peaks with UV spectra similar to these isoflavones were present in MtIFS-overexpressing line C22 compared to a control line (FIGS. 6A, B). Alfalfa leaves have been shown to accumulate glucuronic acid conjugated flavones (Stochmal et al., 2001a; Stochmal et al., 2001b) and digestion of control leaf extracts with β-glucuronidase led to the appearance of free flavones including apigenin (FIG. 6D). However, β-glucuronidase digestion did not shift the five isoflavone peaks present in MtIFS-overexpressing leaves (FIG. 6C). These peaks were shifted by digestion with β-glucosidase to free genistein and biochanin A (FIG. 6E), indicating that these isoflavones were present as glucose rather than glucuronic acid conjugates. Peaks 1 and 4 were further identified as glucose-genistein and glucose-biochanin A, respectively by LC-MS analysis.

REFERENCES

The references listed below are incorporated herein by reference to the extent that they supplement, explain, provide a background for, or teach methodology, techniques, and/or compositions employed herein.

U.S. Pat. No. 4,535,060
U.S. Pat. No. 5,302,523
U.S. Pat. No. 5,322,783
U.S. Pat. No. 5,384,253
U.S. Pat. No. 5,464,765
U.S. Pat. No. 5,508,184
U.S. Pat. No. 5,508,468
U.S. Pat. No. 5,538,877
U.S. Pat. No. 5,538,880
U.S. Pat. No. 5,545,818
U.S. Pat. No. 5,550,318
U.S. Pat. No. 5,563,055
U.S. Pat. No. 5,591,616
U.S. Pat. No. 5,610,042
EPA App. 154,204
PCT App. WO 97/41228
PCT App. WO 94/09699
PCT App. WO 95/06128
PCT App. WO 97/04103
PCT App. WO 92/17598
PCT App. US00/05915
Abdullah et al., *Biotechnology,* 4:1087, 1986.
Adlercreutz and Mazur, *Annals of Medicine,* 29:95-120, 1997.
Adlercreutz, *Baillieres Clinical Endocrinology and Metabolism,* 12: 605-623, 1998.
Adlercreutz, *Baillieres Clinical Endocrinology and Metabolism,* 12: 605-623, 1998.
Akashi et al., *Plant Physiol.,* 121:821-828, 1999.
Anderson and Garner, *Baillieres Clinical Endocrinology and Metabolism* 12:543-557, 1998.
Barnes, *Baillieres Clinical Endocrinology and Metabolism,* 12:559-578, 1998.
Barnes, In: *Flavonoids in the Living System*, ACS, Orlando, Fla., 1996.
Bates, *Mol. Biotechnol.,* 2(2):135-145, 1994.
Battraw and Hall, *Theor. App. Genet.,* 82(2):161-168, 1991.
Bevan et al., *Nucleic Acids Research,* 11(2):369-385, 1983.
Bhattacharjee et al., *J. Plant Bioch. and Biotech.,* 6(2):69-73, 1997.
Bingham, *Crop Sci.,* 31:1098, 1991.
Bouchez et al., *EMBO J.,* 8(13):4197-4204, 1989.
Bower et al., *Plant J.,* 2:409-416, 1992.
Buchanan-Wollaston et al., *Plant Cell Reports,* 11:627-631, 1992.
Buising and Benbow, *Mol. Gen. Genet.,* 243(1):71-81, 1994.
Callis et al., *Genes Dev.,* 1:1183-1200, 1987.
Casa et al., *Proc. Natl. Acad. Sci. USA,* 90(23):11212-11216, 1993.
Chandler et al., *Plant Cell,* 1:1175-1183, 1989.
Christou; et al., *Proc. Natl. Acad. Sci. USA,* 84(12):3962-3966, 1987.
Chu et al., *Scientia Sinica,* 18:659-668, 1975.
Clough and Bent, *Plant J.,* 16:735-743, 1998.
Conkling et al., *Plant Physiol.,* 93:1203-1211, 1990.
De Block et al., *EMBO J.,* 6(9):2513-2518, 1987.
De Block et al., *Plant Physiol.,* 91:694-701, 1989.
Dellaporta et al., In: *Chromosome Structure and Function: Impact of New Concepts,* 18*th Stadler Genetics Symposium,* 11:263-282, 1988.
D'Halluin et al., *Plant Cell,* 4(12):1495-1505, 1992.
Dixon and Ferriera, *Phytochemistry,* 760:205-211, 2002.
Dixon et al., *Phytochemistry,* 27:2801-2808, 1988.
Dixon, In: *Comprehensive Natural Products Chemistry*, Vol. 1, Sankawa (ed). Elsevier, 773-823, 1999.
Dong et al., *Plant Physiology,* 127:46-57, 2001.
Draper et al., *J. Nutrition,* 127:1795-1799, 1997.
Ebert et al., *Proc. Natl. Acad. Sci. USA,* 84:5745-5749, 1987.
Ellis et al., *EMBO J.,* 6(11):3203-3208, 1987.
Faulkner et al., *Carcinogenesis,* 19:605-609, 1998.
Fotsis et al., *J. Nutr.,* 125:790S-797S, 1995.
Fraley et al., *BioTech.,* 3:629-635, 1985.
Fromm et al., *Nature,* 319:791-793, 1986.
Gallie et al., *Plant Cell,* 1:301-311, 1989.
Gelvin et al., In: *Plant Molecular Biology Manual,* 1990.
Ghosh-Biswas et al., *J. Biotechnol.,* 32(1):1-10, 1994.
Graham et al., *Mol. Plant-Microbe Interact.,* 3:157-166, 1990.
Graham, *Plant Physiol. Biochem.,* 36:135-144, 1998.
Hagio et al., *Plant Cell Rep.,* 10(5):260-264, 1991.
Hakamatsuka et al., *Chem. Pharm. Bull.,* 7:1942-1945, 1990.
Hakamatsuka et al., *Phytochemistry,* 49:497-505, 1998.
Hamilton et al., *Proc. Natl. Acad. Sci. USA,* 93(18):9975-9979, 1996.
Haseloff et al., *Proc. Natl. Acad. Sci. USA,* 94(6):2122-2127, 1997.
He et al., *Plant Cell Reports,* 14(2-3):192-196, 1994.
Hensgens et al., *Plant Mol. Biol.,* 22(6):1101-1127, 1993.
Hiei et al., *Plant. Mol. Biol.,* 35(1-2):205-218, 1997.
Hinchee et al., *BioTech.,* 6:915-922, 1988.
Hou and Lin, *Plant Physiology,* 111:166, 1996.
Hudspeth and Grula, *Plant Mol. Biol.,* 12:579-589, 1989.
Ikuta et al., *BioTech.,* 8:241-242, 1990.
Ishidia et al., *Nat. Biotechnol.,* 14(6):745-750, 1996.
Jung et al., 2000, *Nature BioTech.,* 18:208-212, 2000.
Junghans et al., *Plant Mol. Biol.* 22:239-253, 1993.
Kaeppler et al., *Plant Cell Reports,* 9:415-418, 1990.
Kaeppler et al., *Theor. Appl. Genet.,* 84(5-6):560-566, 1992.
Katz et al., *J. Gen. Microbiol.,* 129:2703-2714, 1983.
Klee et al., *BioTech.,* 3(7):637-642, 1985.
Knittel et al., *Plant Cell Reports,* 14(2-3):81-86, 1994.
Kochs and Grisebach, *Eur. J. Biochem.,* 155:311-318, 1986.
Lamartiniere et al., *Proc. Soc. Experim. Biol. Med.,* 208:120-123, 1995.
Lawton et al., *Plant Mol. Biol.,* 9:315-324, 1987.
Lazzeri, *Methods Mol. Biol.,* 49:95-106, 1995.
Lee et al., *Korean J. Genet.,* 11(2):65-72, 1989.
Lorz et al., *Mol. Gen. Genet.,* 199:178-182, 1985.
Mabry et al., In: *The systematic identification of the flavonoids*, New York, N.Y., Springer-Verlag, 1970.

Marcotte et al., *Nature,* 335:454, 1988.
McCabe and Martinell, *BioTech.,* 11(5):596-598, 1993.
McCormac et al., *Euphytica,* 99(1):17-25, 1998.
McKhann and Hirsch, *Plant Mol. Biol.,* 24(5):767-77, 1994.
Messina et al., *Nutrition and Cancer,* 21:113-131, 1994.
Muir et al., *Nature Biotech.,* 19:470-474, 2001.
Murakami et al., *Mol. Gen. Genet.,* 205:42-50, 1986.
Murashige and Skoog, *Physiol. Plant.,* 15:473-497, 1962.
Nagatani et al., *Biotech. Tech.,* 11(7):471-473, 1997.
Odell et al., *Nature,* 313:810-812, 1985.
Ogawa et al., *Sci. Rep.,* 13:42-48, 1973.
Omirulleh et al., *Plant Mol. Biol.,* 21(3):415-428, 1993.
Ow et al., *Science,* 234:856-859, 1986.
Park et al., *Chem. Pharmacol. Bull.,* 40:1978-1980, 1992.
Park et al., *Phytochemistry,* 38:373-380, 1995.
Potrykus et al., *Mol. Gen. Genet.,* 199:183-188, 1985.
Prasher et al., *Biochem. Biophys. Res. Commun.,* 126(3): 1259-1268, 1985.
Rauth et al., *British J. Cancer,* 75:1559-1566, 1997.
Reichel et al., *Proc. Natl. Acad. Sci. USA,* 93(12):5888-5893. 1996.
Rhodes et al., *Methods Mol. Biol.,* 55:121-131, 1995.
Rice-Evans and Miller, *Biochemical Soc. Transact.,* 24:790-794, 1996.
Ritala et al., *Plant Mol. Biol.,* 24(2):317-325, 1994.
Rogers et al., *Methods Enzymol.,* 153:253-277, 1987.
Sambrook et al., In: *Molecular Cloning-A Laboratory Manual* (second edition), Cold Spring Harbour Laboratory Press, 1989.
Schröder, *Trends in Plant Sci.,* 2:373-378, 1997.
Sfakianos et al., *J. Nutrition,* 127:1260-1268, 1997.
Sheen et al., *Plant J.,* 8(5):777-784, 1995.
Singsit et al., *Transgenic Res.,* 6(2):169-176, 1997.
Spencer et al., *Plant Molec. Biol.,* 18:201-210, 1992.
Stalker et al., *Science,* 242:419-422, 1988.
Steele et al., *Arch. Biochem. Biophys.,* 367:147-150, 1999.
Stochmal et al., *J. Agric. Food Chem.,* 49:5310-5314, 2001b.
Stochmal et al., *J. Agric. Food Chem.,* 49:753-758, 2001 a.
Sullivan et al., *Mol. Gen. Genet.,* 215(3):431-440, 1989.
Sumner et al., *J. Mass Spectrometry,* 31:472-485, 1996.
Sutcliffe, *Proc. Natl. Acad. Sci. USA,* 75:3737-3741, 1978.
Thillet et al., *J. Biol. Chem.,* 263:12500-12508, 1988.
Thomas et al., *Plant Sci.,* 69:189-198, 1990.
Thompson et al., *EMBO J.,* 6(9):2519-2523, 1987.
Thompson et al., *Euphytica,* 85(1-3):75-80, 1995.
Tian et al., *Plant Cell Rep.,* 16:267-271, 1997.
Tikkanen et al., *Proc. Natl. Acad. Sci. USA,* 95:3106-3110, 1998.
Tingay et al., *Plant J.,* 11(6):1369-1376, 1997.
Tomes et al., *Plant. Mol. Biol.,* 14(2):261-268, 1990.
Torbet et al., *Crop Science,* 38(1):226-231, 1998.
Torbet et al., *Plant Cell Reports,* 14(10):635-640, 1995.
Toriyama et al., *Theor. Appl. Genet.,* 73:16, 1986.
Tsukada et al., *Plant Cell Physiol.,* 30(4)599-604, 1989.
Twell et al., *Plant Physiol,* 91:1270-1274, 1989.
Uchimiya et al., *Mol. Gen. Genet.,* 204:204, 1986.
Uckun et al., *Science,* 267:886-891, 1995.
Van Eck et al., *Plant Cell Reports,* 14(5):299-304, 1995.
Vasil et al., *Plant Physiol.,* 91:1575-1579, 1989.
Wagner et al., *Metabolism—Clinical and Experimental,* 46:698-705, 1997.
Walker et al., *Proc. Natl. Acad. Sci. USA,* 84:6624-6628, 1987.
Wang et al., *Molec. Cellular Biol.,* 12(8):3399-3406, 1992.
Winkel-Shirley, *Physiologia Plantarum,* 107:142-149, 1999.
Winkel-Shirley, *Plant Physiology,* 126:485-493, 2001.
Yamada et al., *Plant Cell Rep.,* 4:85, 1986.
Yanagihara et al., *Cancer Research,* 53:5815-5821, 1993.
Yang and Russell, *Proc. Natl. Acad. Sci. USA,* 87:4144-4148, 1990.
Ye et al., *Science,* 287:303-305, 2000.
Yu et al., *Plant Physiology,* 124:781-794, 2000.
Zheng and Edwards, *J. Gen. Virol.,* 71:1865-1868, 1990.
Zhou et al., *Plant Cell Reports,* 12(11).612-616, 1993.
Zukowsky et al., *Proc. Natl. Acad. Sci. USA,* 80:1101-1105, 1983.

What is claimed is:

1. A method of increasing isoflavonoid biosynthesis in a plant comprising:

a) down-regulating flavanone 3-hydroxylase in said plant; and b) up-regulating isoflavone synthase by introducing a transgene encoding said isoflavone synthase into said plant.

2. The method of claim 1, wherein said plant comprises a mutant flavanone 3-hydroxylase gene exhibiting a loss of function with respect to a flavanone 3-hydroxylase gene lacking said mutation.

3. The method of claim 1, wherein introducing said transgene comprises genetically transforming said plant or a parent plant of any previous generation of said plant with said transgene.

4. The method of claim 1, wherein said isoflavone synthase comprises the polypeptide sequence of SEQ ID NO:2.

5. The method of claim 1, further defined as comprising up-regulating chalcone isomerase in said plant.

6. The method of claim 5, wherein said chalcone isomerase comprises the polypeptide sequence encoded by SEQ ID NO:3.

7. The method of claim 5, wherein up-regulating chalcone isomerase comprises introducing a transgene encoding said chalcone isomerase into said plant.

8. The method of claim 7, wherein introducing said transgene comprises genetically transforming said plant or a parent plant of any previous generation of said plant with said transgene.

9. The method of claim 5, wherein up-regulating chalcone isomerase comprises introducing a transgene encoding the PAP1 gene into said plant.

10. The method of claim 1, further defined as comprising up-regulating chalcone synthase in said plant.

11. The method of claim 10, wherein said chalcone synthase comprises the polypeptide sequence encoded by SEQ ID NO:5 or SEQ ID NO:6.

12. The method of claim 1, wherein down-regulating flavanone 3-hydroxylase comprises expression of an antisense oligonucleotide complementary to the gene encoding said flavanone 3-hydroxylase.

13. The method of claim 12, wherein said antisense oligonucleotide comprises from about 20 to about 1242 nucleotides complementary to the nucleic acid sequence of SEQ ID NO: 10, from about 20 to about 815 nucleotides complementary to the nucleic acid sequence of SEQ ID NO: 13 or from about 20 to about 5586 nucleotides complementary to nucleotides 82850-88437 of SEQ ID NO: 15.

14. The method of claim 13, wherein the antisense oligonucleotide is further defined as comprising from about 20 to about 780 nucleotides complementary to nucleotides 82850-83062, 83159-83406, 86908-87232, and/or 87801-88437 of SEQ ID NO: 15.

15. The method of claim 13, wherein the antisense oligonucleotide is further defined as comprising from about 20 to about 1021 nucleotides complementary to nucleotides 82850-83062, 83159-83406, 86908-87232, and/or 87801-88043 of SEQ ID NO: 15.

16. The method of claim 12, wherein introducing said selected DNA comprises genetically transforming said plant or a parent plant of any previous generation of said plant with said selected DNA.

17. The method of claim 1, wherein the plant is a monocotyledonous plant.

18. The method of 11, wherein said monocotyledonous plant is selected from the group consisting of wheat, maize, rye, rice, oat, barley, turfgrass, sorghum, millet and sugarcane.

19. The method of claim 18, wherein the monocotyledonous plant is maize.

20. The method of claim 1, wherein the plant is a dicotyledonous plant.

21. The method of claim 20, wherein said dicotyledonous plant is selected from the group consisting of tobacco, tomato, potato, soybean, cotton, canola, alfalfa, sunflower, and cotton.

22. A transgenic plant stably transformed with:

a) a first selected DNA comprising a nucleic acid encoding an antisense oligonucleotide operably linked to a promoter functional in said plant, wherein said antisense oligonucleotide comprises from about 20 to about 1242 nucleotides complementary to the nucleic acid sequence of SEQ ID NO: 10, from about 20 to about 815 nucleotides complementary to the nucleic acid sequence of SEQ ID NO: 13 or from about 20 to about 5586 nucleotides complementary to nucleotides 82850-88437 of SEQ ID NO: 15; and b) a second selected DNA comprising an isoflavone synthase biosynthesis coding sequence operably linked to a promoter functional in said plant, wherein the coding sequence encodes a polypeptide selected from the group consisting of: the polypeptide of SEQ ID NO:2, the polypeptide encoded by SEQ ID NO:3, the polypeptide encoded by SEQ ID NO:5 and the polypeptide encoded by SEQ ID NO:6.

23. The transgenic plant of claim 22, wherein said first selected DNA and/or said second selected DNA comprises an enhancer.

24. The transgenic plant of claim 22, wherein said first selected DNA and/or said second selected DNA comprises plasmid DNA.

25. The transgenic plant of claim 22, wherein said first selected DNA and/or said second selected DNA comprises a sequence encoding a signal peptide.

26. The transgenic plant of claim 22, further defined as a fertile $R_0$ transgenic plant.

27. The transgenic plant of claim 22, further defined as a progeny plant of any generation of a fertile $R_0$ transgenic plant, wherein said transgenic plant has inherited said first selected DNA from said $R_0$ transgenic plant.

28. The transgenic plant of claim 22, further defined as a progeny plant of any generation of a fertile $R_0$ transgenic plant, wherein said transgenic plant has inherited said second selected DNA from said $R_0$ transgenic plant.

29. The transgenic plant of claim 22, further defined as a progeny plant of any generation of a fertile $R_0$ transgenic plant, wherein said transgenic plant has inherited said first and said second selected DNA from said $R_0$ transgenic plant.

30. The transgenic plant of claim 22, wherein said first selected DNA and said second selected DNA were transformed into said plant or a progenitor thereof on a single transformation construct.

31. The transgenic plant of claim 22, wherein the antisense oligonucleotide is further defined as comprising from about 20 to about 780 nucleotides complementary to nucleotides 82850-83062, 83159-83406, 86908-87232, and/or 87801-88437 of SEQ ID NO: 15.

32. The transgenic plant of claim 22, wherein the antisense oligonucleotide is further defined as comprising from about 20 to about 1021 nucleotides complementary to nucleotides 82850-83062, 83159-83406, 86908-87232, and/or 87801-88043 of SEQ ID NO: 15.

33. A seed of the transgenic plant of claim 22, wherein said seed comprises said first selected DNA and said second selected DNA.

34. A method of making food for human or animal consumption comprising:

(a) obtaining the plant of claim 22;

(b) growing said plant under plant growth conditions to produce plant tissue from the plant; and (c) preparing food for human or animal consumption from said plant tissue.

35. The method of claim 34, wherein preparing food comprises harvesting said plant tissue.

36. The method of claim 34, wherein said food is starch, protein, meal, flour or grain.

37. A method of producing a nutraceutical composition comprising (a) obtaining the plant of claim 22;

(b) growing said plant under plant growth conditions to produce plant tissue from the plant; and (c) preparing a nutraceutical composition for human or animal consumption from said plant tissue.

38. A method of increasing isoflavonoid biosynthesis in an alfalfa plant, comprising introducing into said plant a nucleic acid sequence encoding isoflavone synthase, wherein the nucleic acid sequence is operably linked to a promoter operable in said plant and wherein expression of the nucleic acid sequence results in an increase in isoflavonoid biosynthesis in the plant relative to a plant of the same genotype lacking said nucleic acid sequence.

39. The method of claim 38, wherein introducing the nucleic acid sequence into said plant comprises genetic transformation.

40. The method of claim 38, wherein introducing the nucleic acid sequence into said plant comprises plant breeding.

41. The method of claim 38, wherein the biosynthesis of genistein is increased in said plant relative to a plant of the same genotype lacking said nucleic acid sequence.

42. The method of claim 38, wherein the isoflavone synthase comprises the polypeptide sequence of SEQ ID NO:2.

* * * * *

SEQUENCE LISTING

```
<160> NUMBER OF SEQ ID NOS: 15

<210> SEQ ID NO 1
<211> LENGTH: 1824
<212> TYPE: DNA
<213> ORGANISM: Soybean

<400> SEQUENCE: 1

ggaaaattag cctcacaaaa gcaaagatca aacaaaccaa ggacgagaac acgatgttgc     60

ttgaacttgc acttggttta ttggttttgg ctctgtttct gcacttgcgt cccacaccca    120

ctgcaaaatc aaaagcactt cgccatctcc caaacccacc aagcccaaag cctcgtcttc    180

ccttcatagg acaccttcat ctcttaaaag acaaacttct ccactacgca ctcatcgacc    240

tctccaaaaa acatggtccc ttattctctc tctactttgg ctccatgcca accgttgttg    300

cctccacacc agaattgttc aagctcttcc tccaaacgca cgaggcaact tccttcaaca    360

caaggttcca aacctcagcc ataagacgcc tcacctatga tagctcagtg gccatggttc    420

ccttcggacc ttactggaag ttcgtgagga agctcatcat gaacgacctt cccaacgcca    480

ccactgtaaa caagttgagg cctttgagga cccaacagac ccgcaagttc cttagggtta    540
```

-continued

```
tggcccaagg cgcagaggca cagaagcccc ttgacttgac cgaggagctt ctgaaatgga    600

ccaacagcac catctccatg atgatgctcg gcgaggctga ggagatcaga gacatcgctc    660

gcgaggttct taagatcttt ggcgaataca gcctcactga cttcatctgg ccattgaagc    720

atctcaaggt tggaaagtat gagaagagga tcgacgacat cttgaacaag ttcgaccctg    780

tcgttgaaag ggtcatcaag aagcgccgtg agatcgtgag gaggagaaag aacggagagg    840

ttgttgaggg tgaggtcagc ggggttttcc ttgacacttt gcttgaattc gctgaggatg    900

agaccatgga gatcaaaatc accaaggacc acatcgaggg tcttgttgtc gactttttct    960

cggcaggaac agactccaca gcggtggcaa cagagtgggc attggcagaa ctcatcaaca   1020

atcctaaggt gttggaaaag gctcgtgagg aggtctacag tgttgtggga aaggacagac   1080

ttgtggacga agttgacact caaaaccttc cttacattag agcaatcgtg aaggagacat   1140

tccgcatgca cccgccactc ccagtggtca aaagaaagtg cacagaagag tgtgagatta   1200

atggatatgt gatcccagag ggagcattga ttctcttcaa tgtatggcaa gtaggaagag   1260

accccaaata ctgggacaga ccatcggagt tccgtcctga gaggttccta gagacagggg   1320

ctgaagggga agcagggcct cttgatctta ggggacaaca ttttcaactt ctcccatttg   1380

ggtctgggag gagaatgtgc cctggagtca atctggctac ttcgggaatg gcaacacttc   1440

ttgcatctct tattcagtgc ttcgacttgc aagtgctggg tccacaagga cagatattga   1500

agggtggtga cgccaaagtt agcatggaag agagagccgg cctcactgtt ccaagggcac   1560

atagtcttgt ctgtgttcca cttgcaagga tcggcgttgc atctaaactc ctttcttaat   1620

taagatcatc atcatatata atatttactt tttgtgtgtt gataatcatc atttcaataa   1680

ggtctcgttc atctactttt tatgaagtat ataagccctt ccatgcacat tgtatcatct   1740

cccatttgtc ttcgtttgct acctaaggca atcttttttt ttttagaatc acatcatcct   1800

actataaact atcaatcctt atat                                           1824


<210> SEQ ID NO 2
<211> LENGTH: 521
<212> TYPE: PRT
<213> ORGANISM: Soybean

<400> SEQUENCE: 2

Met Leu Leu Glu Leu Ala Leu Gly Leu Leu Val Leu Ala Leu Phe Leu
1               5                   10                  15

His Leu Arg Pro Thr Pro Thr Ala Lys Ser Lys Ala Leu Arg His Leu
            20                  25                  30

Pro Asn Pro Pro Ser Pro Lys Pro Arg Leu Pro Phe Ile Gly His Leu
        35                  40                  45

His Leu Leu Lys Asp Lys Leu Leu His Tyr Ala Leu Ile Asp Leu Ser
    50                  55                  60

Lys Lys His Gly Pro Leu Phe Ser Leu Tyr Phe Gly Ser Met Pro Thr
65                  70                  75                  80

Val Val Ala Ser Thr Pro Glu Leu Phe Lys Leu Phe Leu Gln Thr His
                85                  90                  95

Glu Ala Thr Ser Phe Asn Thr Arg Phe Gln Thr Ser Ala Ile Arg Arg
            100                 105                 110

Leu Thr Tyr Asp Ser Ser Val Ala Met Val Pro Phe Gly Pro Tyr Trp
        115                 120                 125

Lys Phe Val Arg Lys Leu Ile Met Asn Asp Leu Pro Asn Ala Thr Thr
    130                 135                 140
```

-continued

```
Val Asn Lys Leu Arg Pro Leu Arg Thr Gln Gln Thr Arg Lys Phe Leu
145                 150                 155                 160

Arg Val Met Ala Gln Gly Ala Glu Ala Gln Lys Pro Leu Asp Leu Thr
                165                 170                 175

Glu Glu Leu Leu Lys Trp Thr Asn Ser Thr Ile Ser Met Met Met Leu
            180                 185                 190

Gly Glu Ala Glu Glu Ile Arg Asp Ile Ala Arg Glu Val Leu Lys Ile
        195                 200                 205

Phe Gly Glu Tyr Ser Leu Thr Asp Phe Ile Trp Pro Leu Lys His Leu
    210                 215                 220

Lys Val Gly Lys Tyr Glu Lys Arg Ile Asp Asp Ile Leu Asn Lys Phe
225                 230                 235                 240

Asp Pro Val Val Glu Arg Val Ile Lys Lys Arg Arg Glu Ile Val Arg
                245                 250                 255

Arg Arg Lys Asn Gly Glu Val Val Glu Gly Glu Val Ser Gly Val Phe
            260                 265                 270

Leu Asp Thr Leu Leu Glu Phe Ala Glu Asp Glu Thr Met Glu Ile Lys
        275                 280                 285

Ile Thr Lys Asp His Ile Glu Gly Leu Val Val Asp Phe Phe Ser Ala
    290                 295                 300

Gly Thr Asp Ser Thr Ala Val Ala Thr Glu Trp Ala Leu Ala Glu Leu
305                 310                 315                 320

Ile Asn Asn Pro Lys Val Leu Glu Lys Ala Arg Glu Glu Val Tyr Ser
                325                 330                 335

Val Val Gly Lys Asp Arg Leu Val Asp Glu Val Asp Thr Gln Asn Leu
            340                 345                 350

Pro Tyr Ile Arg Ala Ile Val Lys Glu Thr Phe Arg Met His Pro Pro
        355                 360                 365

Leu Pro Val Val Lys Arg Lys Cys Thr Glu Glu Cys Glu Ile Asn Gly
    370                 375                 380

Tyr Val Ile Pro Glu Gly Ala Leu Ile Leu Phe Asn Val Trp Gln Val
385                 390                 395                 400

Gly Arg Asp Pro Lys Tyr Trp Asp Arg Pro Ser Glu Phe Arg Pro Glu
                405                 410                 415

Arg Phe Leu Glu Thr Gly Ala Glu Gly Glu Ala Gly Pro Leu Asp Leu
            420                 425                 430

Arg Gly Gln His Phe Gln Leu Leu Pro Phe Gly Ser Gly Arg Arg Met
        435                 440                 445

Cys Pro Gly Val Asn Leu Ala Thr Ser Gly Met Ala Thr Leu Leu Ala
    450                 455                 460

Ser Leu Ile Gln Cys Phe Asp Leu Gln Val Leu Gly Pro Gln Gly Gln
465                 470                 475                 480

Ile Leu Lys Gly Gly Asp Ala Lys Val Ser Met Glu Glu Arg Ala Gly
                485                 490                 495

Leu Thr Val Pro Arg Ala His Ser Leu Val Cys Val Pro Leu Ala Arg
            500                 505                 510

Ile Gly Val Ala Ser Lys Leu Leu Ser
        515                 520
```

```
<210> SEQ ID NO 3
<211> LENGTH: 950
<212> TYPE: DNA
<213> ORGANISM: Medicago sativa
<220> FEATURE:
<221> NAME/KEY: CDS
```

-continued

```
<222> LOCATION: (41)..(709)

<400> SEQUENCE: 3

gaattcccat agctaaacaa aaaaaattaa gaacaagaat atg gct gca tca atc       55
                                            Met Ala Ala Ser Ile
                                             1               5

acc gca atc act gtg gag aac ctt gaa tac cca gcg gtg gtt acc tct      103
Thr Ala Ile Thr Val Glu Asn Leu Glu Tyr Pro Ala Val Val Thr Ser
                 10                  15                  20

ccg gtc acc ggc aaa tca tat ttc ctc ggt ggc gct ggg gag aga gga      151
Pro Val Thr Gly Lys Ser Tyr Phe Leu Gly Gly Ala Gly Glu Arg Gly
             25                  30                  35

ttg acc att gaa gga aac ttc atc aag ttc act gcc ata ggt gtt tat      199
Leu Thr Ile Glu Gly Asn Phe Ile Lys Phe Thr Ala Ile Gly Val Tyr
         40                  45                  50

ttg gaa gat ata gca gtg gct tca cta gct gcc aaa tgg aag ggt aaa      247
Leu Glu Asp Ile Ala Val Ala Ser Leu Ala Ala Lys Trp Lys Gly Lys
     55                  60                  65

tca tct gaa gag tta ctt gag acc ctt gac ttt tac aga gac atc atc      295
Ser Ser Glu Glu Leu Leu Glu Thr Leu Asp Phe Tyr Arg Asp Ile Ile
 70                  75                  80                  85

tca ggt ccc ttt gaa aag tta att aga ggg tca aag att agg gaa ttg      343
Ser Gly Pro Phe Glu Lys Leu Ile Arg Gly Ser Lys Ile Arg Glu Leu
                 90                  95                 100

agt ggt cct gag tac tca agg aag gtt atg gag aac tgt gtg gca cac      391
Ser Gly Pro Glu Tyr Ser Arg Lys Val Met Glu Asn Cys Val Ala His
            105                 110                 115

ttg aaa tca gtt gga act tat gga gat gca gaa gct gaa gct atg caa      439
Leu Lys Ser Val Gly Thr Tyr Gly Asp Ala Glu Ala Glu Ala Met Gln
        120                 125                 130

aaa ttt gct gaa gct ttc aag cct gtt aat ttt cca cct ggt gcc tct      487
Lys Phe Ala Glu Ala Phe Lys Pro Val Asn Phe Pro Pro Gly Ala Ser
    135                 140                 145

gtt ttc tac agg caa tca cct gat gga ata tta ggg ctt agt ttc tct      535
Val Phe Tyr Arg Gln Ser Pro Asp Gly Ile Leu Gly Leu Ser Phe Ser
150                 155                 160                 165

ccg gat aca agt ata cca gaa aag gag gct gca ctc ata gag aac aag      583
Pro Asp Thr Ser Ile Pro Glu Lys Glu Ala Ala Leu Ile Glu Asn Lys
                170                 175                 180

gca gtt tca tca gca gtg ttg gag act atg atc ggc gag cac gct gtt      631
Ala Val Ser Ser Ala Val Leu Glu Thr Met Ile Gly Glu His Ala Val
            185                 190                 195

tcc cct gat ctt aag cgc tgt tta gct gca aga tta cct gcg ttg ttg      679
Ser Pro Asp Leu Lys Arg Cys Leu Ala Ala Arg Leu Pro Ala Leu Leu
        200                 205                 210

aac gag ggt gct ttc aag att gga aac tga tgatgattat actcctatat        729
Asn Glu Gly Ala Phe Lys Ile Gly Asn
    215                 220

cactgcattt ccaaaagcgt tgcagcacaa gaatgagacc atgaactttt ttaagtctac    789

acgtttaatt ttttgtatat ctatttacct tcttattagt atcaataata tgaaatgaaa    849

gatcttgctt tctactcttg tactatttct gtgatagata atgttaatga gtatcttcat    909

caataaaagt gatttgtttt gtttgttcaa aaaaaaaaaa a                        950


<210> SEQ ID NO 4
<211> LENGTH: 222
<212> TYPE: PRT
<213> ORGANISM: Medicago sativa

<400> SEQUENCE: 4
```

-continued

```
Met Ala Ala Ser Ile Thr Ala Ile Thr Val Glu Asn Leu Glu Tyr Pro
  1               5                  10                  15

Ala Val Val Thr Ser Pro Val Thr Gly Lys Ser Tyr Phe Leu Gly Gly
             20                  25                  30

Ala Gly Glu Arg Gly Leu Thr Ile Glu Gly Asn Phe Ile Lys Phe Thr
         35                  40                  45

Ala Ile Gly Val Tyr Leu Glu Asp Ile Ala Val Ala Ser Leu Ala Ala
     50                  55                  60

Lys Trp Lys Gly Lys Ser Ser Glu Glu Leu Leu Glu Thr Leu Asp Phe
 65                  70                  75                  80

Tyr Arg Asp Ile Ile Ser Gly Pro Phe Glu Lys Leu Ile Arg Gly Ser
                 85                  90                  95

Lys Ile Arg Glu Leu Ser Gly Pro Glu Tyr Ser Arg Lys Val Met Glu
            100                 105                 110

Asn Cys Val Ala His Leu Lys Ser Val Gly Thr Tyr Gly Asp Ala Glu
        115                 120                 125

Ala Glu Ala Met Gln Lys Phe Ala Glu Ala Phe Lys Pro Val Asn Phe
    130                 135                 140

Pro Pro Gly Ala Ser Val Phe Tyr Arg Gln Ser Pro Asp Gly Ile Leu
145                 150                 155                 160

Gly Leu Ser Phe Ser Pro Asp Thr Ser Ile Pro Glu Lys Glu Ala Ala
                165                 170                 175

Leu Ile Glu Asn Lys Ala Val Ser Ser Ala Val Leu Glu Thr Met Ile
            180                 185                 190

Gly Glu His Ala Val Ser Pro Asp Leu Lys Arg Cys Leu Ala Ala Arg
        195                 200                 205

Leu Pro Ala Leu Leu Asn Glu Gly Ala Phe Lys Ile Gly Asn
    210                 215                 220
```

<210> SEQ ID NO 5
<211> LENGTH: 836
<212> TYPE: DNA
<213> ORGANISM: Medicago sativa

<400> SEQUENCE: 5

```
caaatcatat ttcctcggtg gcgctgggga gagaggattg accattgaag gaaacttcat     60

caagttcact gccataggtg tttatttgga agatatagca gtggcttcac tagctgccaa    120

atggaagggt aaatcatctg aagagttact tgagaccctt gacttttaca gagacatcat    180

ctcaggtccc tttgaaaagt taattagagg gtcaaagatt agggaattga gtggtcctga    240

gtactcaagg aaggttatgg agaactgtgt ggcacacttg aaatcagttg gaacttatgg    300

agatgcagaa gctgaagcta tgcaaaaatt tgctgaagct ttcaagcctg ttaattttcc    360

acctggtgcc tctgtttttct acaggcaatc acctgatgga atattagggc ttagtttctc    420

tccggataca agtataccag aaaaggaggc tgcactcata gagaacaagg cagtttcatc    480

agcagtgttg gagactatga tcggcgaaca cgctgtttcc cctgatctta agcgctgttt    540

ggctgcaaga ttacctgcgt tgttgaacga gggtgctttc aagattggaa actgatgatg    600

attatactct tatataaaaa catttccaaa agcgttgcag cacaagaatg agaccatgga    660

cttttttaag tctacacgtt taattttttg tatatctatt taccttctta ttagtatcaa    720

tagtatgaaa tgaaagatct tgctttctac tcttgtacta tttctgtgat agataatgtt    780

aatgagtatc ttcatcaata aaagtgattt gttttgtttg ttcaaaaaaa aaaaaa        836
```

-continued

```
<210> SEQ ID NO 6
<211> LENGTH: 1380
<212> TYPE: DNA
<213> ORGANISM: Medicago sativa
<220> FEATURE:
<221> NAME/KEY: CDS
<222> LOCATION: (67)..(1236)

<400> SEQUENCE: 6

gaattcccaa caaacaagta ctgcaaacca attgagtatt acatagaaac tactagagat      60

accaag atg gtg agt gta tct gaa att cgc aag gct cag agg gca gaa        108
       Met Val Ser Val Ser Glu Ile Arg Lys Ala Gln Arg Ala Glu
         1               5                  10

ggt cct gca acc att ttg gcc att ggc act gca aat cca gca aat tgt       156
Gly Pro Ala Thr Ile Leu Ala Ile Gly Thr Ala Asn Pro Ala Asn Cys
 15                  20                  25                  30

gtt gaa caa agt aca tat cct gat ttt tac ttt aaa atc aca aat agc       204
Val Glu Gln Ser Thr Tyr Pro Asp Phe Tyr Phe Lys Ile Thr Asn Ser
                 35                  40                  45

gag cac aag act gaa ctc aaa gag aaa ttc caa cgc atg tgt gat aaa       252
Glu His Lys Thr Glu Leu Lys Glu Lys Phe Gln Arg Met Cys Asp Lys
             50                  55                  60

tct atg atc aag agg aga tac atg tac cta aca gag gag att ttg aaa       300
Ser Met Ile Lys Arg Arg Tyr Met Tyr Leu Thr Glu Glu Ile Leu Lys
         65                  70                  75

gag aat cct agt gtt tgt gaa tat atg gca cct tca ttg gat gcc agg       348
Glu Asn Pro Ser Val Cys Glu Tyr Met Ala Pro Ser Leu Asp Ala Arg
     80                  85                  90

caa gac atg gtg gtg gta gag gta cct aga cta ggg aag gag gct gca       396
Gln Asp Met Val Val Val Glu Val Pro Arg Leu Gly Lys Glu Ala Ala
 95                 100                 105                 110

gtg aag gct ata aaa gaa tgg ggt caa cca aag tca aag att act cac       444
Val Lys Ala Ile Lys Glu Trp Gly Gln Pro Lys Ser Lys Ile Thr His
                115                 120                 125

tta att gtt tgc act aca agt ggt gta gac atg cct gga gct gat tac       492
Leu Ile Val Cys Thr Thr Ser Gly Val Asp Met Pro Gly Ala Asp Tyr
            130                 135                 140

caa ctc aca aaa ctc ttg ggt ctt cgc cca tat gtg aaa agg tat atg       540
Gln Leu Thr Lys Leu Leu Gly Leu Arg Pro Tyr Val Lys Arg Tyr Met
        145                 150                 155

atg tac caa caa ggt tgc ttt gca gga ggc acg gtg ctt cgt ttg gct       588
Met Tyr Gln Gln Gly Cys Phe Ala Gly Gly Thr Val Leu Arg Leu Ala
    160                 165                 170

aaa gat ttg gct gag aac aac aaa ggt gcc cgt gta ttg gtt gtt tgt       636
Lys Asp Leu Ala Glu Asn Asn Lys Gly Ala Arg Val Leu Val Val Cys
175                 180                 185                 190

tct gaa gtc act gca gtc aca ttc cgc ggc cct agt gat act cac ttg       684
Ser Glu Val Thr Ala Val Thr Phe Arg Gly Pro Ser Asp Thr His Leu
                195                 200                 205

gac agc ctt gtt gga caa gca cta ttt gga gac gga gct gct gca cta       732
Asp Ser Leu Val Gly Gln Ala Leu Phe Gly Asp Gly Ala Ala Ala Leu
            210                 215                 220

att gtt ggt tct gat cca gta cca gaa att gag aaa cct ata ttt gag       780
Ile Val Gly Ser Asp Pro Val Pro Glu Ile Glu Lys Pro Ile Phe Glu
        225                 230                 235

atg gtt tgg act gca caa aca att gct cca gat agt gaa gga gcc att       828
Met Val Trp Thr Ala Gln Thr Ile Ala Pro Asp Ser Glu Gly Ala Ile
    240                 245                 250

gat ggt cac ctt cgt gaa gct gga cta aca ttc cac ctt ctt aaa gat       876
Asp Gly His Leu Arg Glu Ala Gly Leu Thr Phe His Leu Leu Lys Asp
```

-continued

```
255                 260                 265                 270

gtt cct ggg att gtt tca aag aac att gat aaa gca tta gtt gaa gct      924
Val Pro Gly Ile Val Ser Lys Asn Ile Asp Lys Ala Leu Val Glu Ala
                275                 280                 285

ttc caa cca ttg gga att tct gat tac aac tca atc ttt tgg att gca      972
Phe Gln Pro Leu Gly Ile Ser Asp Tyr Asn Ser Ile Phe Trp Ile Ala
            290                 295                 300

cac cct ggt ggc cct gca att tta gat caa gta gag caa aag tta gcc     1020
His Pro Gly Gly Pro Ala Ile Leu Asp Gln Val Glu Gln Lys Leu Ala
        305                 310                 315

ttg aag cct gaa aag atg aga gcc act aga gaa gtg ctt agt gaa tat     1068
Leu Lys Pro Glu Lys Met Arg Ala Thr Arg Glu Val Leu Ser Glu Tyr
    320                 325                 330

gga aat atg tca agt gca tgt gtt ttg ttt atc tta gat gaa atg aga     1116
Gly Asn Met Ser Ser Ala Cys Val Leu Phe Ile Leu Asp Glu Met Arg
335                 340                 345                 350

aag aaa tca act caa gat gga ctg aag aca aca gga gaa gga ctt gaa     1164
Lys Lys Ser Thr Gln Asp Gly Leu Lys Thr Thr Gly Glu Gly Leu Glu
                355                 360                 365

tgg ggt gtg tta ttt ggc ttt gga cca gga ctt acc ata gaa act gtt     1212
Trp Gly Val Leu Phe Gly Phe Gly Pro Gly Leu Thr Ile Glu Thr Val
            370                 375                 380

gtt ttg cgc agt gtc gct ata tga aatgcttaat tattttattt ttatttatca    1266
Val Leu Arg Ser Val Ala Ile
        385

ctttcaaatt tgcttgattt ttatgtaagg atgaaaaact cgtctacagt tcaacattta   1326

ctgtcatatt aaaaataata caattgtgat tccctttaaa aaaaaaagga attc         1380


<210> SEQ ID NO 7
<211> LENGTH: 389
<212> TYPE: PRT
<213> ORGANISM: Medicago sativa

<400> SEQUENCE: 7

Met Val Ser Val Ser Glu Ile Arg Lys Ala Gln Arg Ala Glu Gly Pro
  1               5                  10                  15

Ala Thr Ile Leu Ala Ile Gly Thr Ala Asn Pro Ala Asn Cys Val Glu
            20                  25                  30

Gln Ser Thr Tyr Pro Asp Phe Tyr Phe Lys Ile Thr Asn Ser Glu His
        35                  40                  45

Lys Thr Glu Leu Lys Glu Lys Phe Gln Arg Met Cys Asp Lys Ser Met
     50                  55                  60

Ile Lys Arg Arg Tyr Met Tyr Leu Thr Glu Glu Ile Leu Lys Glu Asn
 65                  70                  75                  80

Pro Ser Val Cys Glu Tyr Met Ala Pro Ser Leu Asp Ala Arg Gln Asp
                 85                  90                  95

Met Val Val Val Glu Val Pro Arg Leu Gly Lys Glu Ala Ala Val Lys
            100                 105                 110

Ala Ile Lys Glu Trp Gly Gln Pro Lys Ser Lys Ile Thr His Leu Ile
        115                 120                 125

Val Cys Thr Thr Ser Gly Val Asp Met Pro Gly Ala Asp Tyr Gln Leu
    130                 135                 140

Thr Lys Leu Leu Gly Leu Arg Pro Tyr Val Lys Arg Tyr Met Met Tyr
145                 150                 155                 160

Gln Gln Gly Cys Phe Ala Gly Gly Thr Val Leu Arg Leu Ala Lys Asp
                165                 170                 175
```

-continued

```
Leu Ala Glu Asn Asn Lys Gly Ala Arg Val Leu Val Val Cys Ser Glu
            180                 185                 190

Val Thr Ala Val Thr Phe Arg Gly Pro Ser Asp Thr His Leu Asp Ser
        195                 200                 205

Leu Val Gly Gln Ala Leu Phe Gly Asp Gly Ala Ala Ala Leu Ile Val
    210                 215                 220

Gly Ser Asp Pro Val Pro Glu Ile Glu Lys Pro Ile Phe Glu Met Val
225                 230                 235                 240

Trp Thr Ala Gln Thr Ile Ala Pro Asp Ser Glu Gly Ala Ile Asp Gly
                245                 250                 255

His Leu Arg Glu Ala Gly Leu Thr Phe His Leu Leu Lys Asp Val Pro
            260                 265                 270

Gly Ile Val Ser Lys Asn Ile Asp Lys Ala Leu Val Glu Ala Phe Gln
        275                 280                 285

Pro Leu Gly Ile Ser Asp Tyr Asn Ser Ile Phe Trp Ile Ala His Pro
    290                 295                 300

Gly Gly Pro Ala Ile Leu Asp Gln Val Glu Gln Lys Leu Ala Leu Lys
305                 310                 315                 320

Pro Glu Lys Met Arg Ala Thr Arg Glu Val Leu Ser Glu Tyr Gly Asn
                325                 330                 335

Met Ser Ser Ala Cys Val Leu Phe Ile Leu Asp Glu Met Arg Lys Lys
            340                 345                 350

Ser Thr Gln Asp Gly Leu Lys Thr Thr Gly Glu Gly Leu Glu Trp Gly
        355                 360                 365

Val Leu Phe Gly Phe Gly Pro Gly Leu Thr Ile Glu Thr Val Val Leu
    370                 375                 380

Arg Ser Val Ala Ile
385


<210> SEQ ID NO 8
<211> LENGTH: 1423
<212> TYPE: DNA
<213> ORGANISM: Medicago sativa
<220> FEATURE:
<221> NAME/KEY: CDS
<222> LOCATION: (106)..(1275)

<400> SEQUENCE: 8

cgaattccca actaagtact gtaaaccata gagttcaaat tacagtactt tactttcatt      60

tgataccaac ctaccatatc attgctacac agaaactata tcaag atg gtg agt gta     117
                                                  Met Val Ser Val
                                                    1

tct gaa att cgt cag gct caa agg gca gaa ggc cct gca acc atc atg       165
Ser Glu Ile Arg Gln Ala Gln Arg Ala Glu Gly Pro Ala Thr Ile Met
  5                  10                  15                  20

gcc att ggc act gca aat cca tcc aac tgt gtt gaa caa agc aca tat       213
Ala Ile Gly Thr Ala Asn Pro Ser Asn Cys Val Glu Gln Ser Thr Tyr
                 25                  30                  35

cct gat ttc tac ttc aaa atc aca aac agt gag cac aaa gtt gaa ctc       261
Pro Asp Phe Tyr Phe Lys Ile Thr Asn Ser Glu His Lys Val Glu Leu
             40                  45                  50

aaa gag aaa ttt caa cgc atg tgt gat aaa tcc atg atc aag agg aga       309
Lys Glu Lys Phe Gln Arg Met Cys Asp Lys Ser Met Ile Lys Arg Arg
         55                  60                  65

tac atg tat ctt acc gaa gag att ttg aaa gaa aat cca agt gta tgt       357
Tyr Met Tyr Leu Thr Glu Glu Ile Leu Lys Glu Asn Pro Ser Val Cys
     70                  75                  80
```

-continued

```
gaa tac atg gca cct tca ttg gat gct agg cag gac atg gtg gtg gta      405
Glu Tyr Met Ala Pro Ser Leu Asp Ala Arg Gln Asp Met Val Val Val
 85                  90                  95                 100

gag gta cct aga ctt gga aag gag gct gca gtg aag gct ata aaa gaa      453
Glu Val Pro Arg Leu Gly Lys Glu Ala Ala Val Lys Ala Ile Lys Glu
                105                 110                 115

tgg ggc caa cca aaa tca aag att aca cac tta ata ttt tgt acc aca      501
Trp Gly Gln Pro Lys Ser Lys Ile Thr His Leu Ile Phe Cys Thr Thr
            120                 125                 130

agt ggt gta gac atg cct ggt gcc gat tac caa ctc aca aaa ctc tta      549
Ser Gly Val Asp Met Pro Gly Ala Asp Tyr Gln Leu Thr Lys Leu Leu
        135                 140                 145

ggt ctt cgt cca tat gtg aaa agg tat atg atg tac caa caa ggg tgc      597
Gly Leu Arg Pro Tyr Val Lys Arg Tyr Met Met Tyr Gln Gln Gly Cys
    150                 155                 160

ttt gca ggt ggg acg gtc ctt cgt ttg gcc aag gac ttg gct gag aac      645
Phe Ala Gly Gly Thr Val Leu Arg Leu Ala Lys Asp Leu Ala Glu Asn
165                 170                 175                 180

aat aaa ggt gct cgt gtg ttg gtt gtt tgt tct gaa gtt act gcg gtg      693
Asn Lys Gly Ala Arg Val Leu Val Val Cys Ser Glu Val Thr Ala Val
                185                 190                 195

aca ttc cgt ggt cct agt gat act cat tta gac agt ctt gtt gga caa      741
Thr Phe Arg Gly Pro Ser Asp Thr His Leu Asp Ser Leu Val Gly Gln
            200                 205                 210

gca ctc ttt gga gat ggt gct gct gca ctc att gtt ggt tct gac cca      789
Ala Leu Phe Gly Asp Gly Ala Ala Ala Leu Ile Val Gly Ser Asp Pro
        215                 220                 225

ata cca gaa att gag aaa cct ata ttt gag atg gtt tgg act gca caa      837
Ile Pro Glu Ile Glu Lys Pro Ile Phe Glu Met Val Trp Thr Ala Gln
    230                 235                 240

aca att gct cca gac agt gaa gga gcc att gat ggt cac ctt gtc gaa      885
Thr Ile Ala Pro Asp Ser Glu Gly Ala Ile Asp Gly His Leu Val Glu
245                 250                 255                 260

gct ggt cta aca ttt cac ctt ctt aaa gat gtt cct ggg att gtt tca      933
Ala Gly Leu Thr Phe His Leu Leu Lys Asp Val Pro Gly Ile Val Ser
                265                 270                 275

aag aac att gat aaa gca ttg att gag gct ttc caa cca tta aac atc      981
Lys Asn Ile Asp Lys Ala Leu Ile Glu Ala Phe Gln Pro Leu Asn Ile
            280                 285                 290

tct gat tac aat tca atc ttc tgg att gct cac cca ggt gga ccc gca     1029
Ser Asp Tyr Asn Ser Ile Phe Trp Ile Ala His Pro Gly Gly Pro Ala
        295                 300                 305

att cta gac caa gtt gaa gaa aag tta ggc tta aaa cct gaa aag atg     1077
Ile Leu Asp Gln Val Glu Glu Lys Leu Gly Leu Lys Pro Glu Lys Met
    310                 315                 320

aag gcc act agg gaa gta ctt agt gaa tat ggt aac atg tca agt gca     1125
Lys Ala Thr Arg Glu Val Leu Ser Glu Tyr Gly Asn Met Ser Ser Ala
325                 330                 335                 340

tgt gta ttg ttc atc tta gat gag atg aga aag aaa tcg gca caa gcg     1173
Cys Val Leu Phe Ile Leu Asp Glu Met Arg Lys Lys Ser Ala Gln Ala
                345                 350                 355

gga ctt aaa acc aca gga gaa ggc ctt gac tgg ggt gtg ttg ttt ggc     1221
Gly Leu Lys Thr Thr Gly Glu Gly Leu Asp Trp Gly Val Leu Phe Gly
            360                 365                 370

ttc gga cct gga ctt acc att gaa acc gtt gtt ctc cat agc gtg gct     1269
Phe Gly Pro Gly Leu Thr Ile Glu Thr Val Val Leu His Ser Val Ala
        375                 380                 385

ata tga aatgattgat tgttttattt tattgtatta cttttaaact tgcttgaaat      1325
Ile
```

-continued

```
tccatgtaag aataaataca gagttcatgt accatggatg ttaaaacgaa tataccattt   1385

gtagcttctt ctttttctcg caaaaaaaaa aggaattc                           1423


<210> SEQ ID NO 9
<211> LENGTH: 389
<212> TYPE: PRT
<213> ORGANISM: Medicago sativa

<400> SEQUENCE: 9

Met Val Ser Val Ser Glu Ile Arg Gln Ala Gln Arg Ala Glu Gly Pro
  1               5                  10                  15

Ala Thr Ile Met Ala Ile Gly Thr Ala Asn Pro Ser Asn Cys Val Glu
             20                  25                  30

Gln Ser Thr Tyr Pro Asp Phe Tyr Phe Lys Ile Thr Asn Ser Glu His
         35                  40                  45

Lys Val Glu Leu Lys Glu Lys Phe Gln Arg Met Cys Asp Lys Ser Met
     50                  55                  60

Ile Lys Arg Arg Tyr Met Tyr Leu Thr Glu Glu Ile Leu Lys Glu Asn
 65                  70                  75                  80

Pro Ser Val Cys Glu Tyr Met Ala Pro Ser Leu Asp Ala Arg Gln Asp
                 85                  90                  95

Met Val Val Val Glu Val Pro Arg Leu Gly Lys Glu Ala Ala Val Lys
            100                 105                 110

Ala Ile Lys Glu Trp Gly Gln Pro Lys Ser Lys Ile Thr His Leu Ile
        115                 120                 125

Phe Cys Thr Thr Ser Gly Val Asp Met Pro Gly Ala Asp Tyr Gln Leu
    130                 135                 140

Thr Lys Leu Leu Gly Leu Arg Pro Tyr Val Lys Arg Tyr Met Met Tyr
145                 150                 155                 160

Gln Gln Gly Cys Phe Ala Gly Gly Thr Val Leu Arg Leu Ala Lys Asp
                165                 170                 175

Leu Ala Glu Asn Asn Lys Gly Ala Arg Val Leu Val Val Cys Ser Glu
            180                 185                 190

Val Thr Ala Val Thr Phe Arg Gly Pro Ser Asp Thr His Leu Asp Ser
        195                 200                 205

Leu Val Gly Gln Ala Leu Phe Gly Asp Gly Ala Ala Ala Leu Ile Val
    210                 215                 220

Gly Ser Asp Pro Ile Pro Glu Ile Glu Lys Pro Ile Phe Glu Met Val
225                 230                 235                 240

Trp Thr Ala Gln Thr Ile Ala Pro Asp Ser Glu Gly Ala Ile Asp Gly
                245                 250                 255

His Leu Val Glu Ala Gly Leu Thr Phe His Leu Leu Lys Asp Val Pro
            260                 265                 270

Gly Ile Val Ser Lys Asn Ile Asp Lys Ala Leu Ile Glu Ala Phe Gln
        275                 280                 285

Pro Leu Asn Ile Ser Asp Tyr Asn Ser Ile Phe Trp Ile Ala His Pro
    290                 295                 300

Gly Gly Pro Ala Ile Leu Asp Gln Val Glu Glu Lys Leu Gly Leu Lys
305                 310                 315                 320

Pro Glu Lys Met Lys Ala Thr Arg Glu Val Leu Ser Glu Tyr Gly Asn
                325                 330                 335

Met Ser Ser Ala Cys Val Leu Phe Ile Leu Asp Glu Met Arg Lys Lys
            340                 345                 350

Ser Ala Gln Ala Gly Leu Lys Thr Thr Gly Glu Gly Leu Asp Trp Gly
```

-continued

```
        355                 360                 365

Val Leu Phe Gly Phe Gly Pro Gly Leu Thr Ile Glu Thr Val Val Leu
    370                 375                 380

His Ser Val Ala Ile
385


<210> SEQ ID NO 10
<211> LENGTH: 1242
<212> TYPE: DNA
<213> ORGANISM: Arabidopsis thaliana

<400> SEQUENCE: 10

ctcaactcta aattcgtccg agacgaagac gaacgcccta aagtcgctta caatgtgttt      60

agcgacgaaa tcccggtgat ctctctcgcc ggtatcgatg acgtcgatgg aaaaagagga     120

gagatctgcc gtcagatcgt cgaggcttgt gagaattggg gtatcttcca agtggttgat     180

cacggcgtcg atactaactt ggtggcggat atgactcgcc tcgctcgtga cttctttgct     240

ttacctccgg aagacaagct ccgtttcgac atgtccggtg gtaaaaaagg tggattcatc     300

gtctctagtc acctccaggt aaaagccaca ccacaatctt ctaggttaaa tacgtaatta     360

tgttttaatc ttgccgttaa agacataata attatactat aaatacaggg agaggctgtg     420

caagattgga gagagattgt aacgtatttc tcgtacccgg tgagaaacag agactactca     480

cggtggccaa ataagcctga aggatgggtg aaagtgacgg aggagtatag tgagaggctt     540

atgagtttgg cttgtaagct tcttgaggtt ttgtctgaag ctatgggtct tgagaaagag     600

tctcttacca atgcatgcgt cgatatggac caaaagattg ttgttaatta ttacccaaaa     660

tgccctcagc ctgatctcac cctcggactc aagcgtcaca ctgaccctgg aaccattacc     720

ttgctgctac aagaccaagt cggtggatta caagccacac gtgacaatgg caagacctgg     780

attacggttc agcctgttga aggagcgttt gtcgtcaatc tcggcgacca cggtcatgtt     840

agtactctat ccatttattg gctttttttgt ttctctgttt ttggttttga cttggtcaac     900

cttgatttgt cttgatgaag tttttgagca atgggaggtt caagaatgct gatcatcagg     960

ccgtggtgaa ctctaactcg agcagattat ccatagccac gttccagaac cccgcgccgg    1020

atgccacagt gtatccactg aaagtaagag aaggagagaa ggcaatattg gaggagccaa    1080

tcacgtttgc cgagatgtat aagagaaaga tgggaagaga tttggagctt gctcgcctca    1140

agaagctggc taaagaggag cgtgaccaca aagaagttgc caagcctgtc gaccaaatct    1200

tcgcttagaa tctctgtgtt cttgcttact tgttgttgcg tt                       1242


<210> SEQ ID NO 11
<211> LENGTH: 342
<212> TYPE: PRT
<213> ORGANISM: Oryza sativa

<400> SEQUENCE: 11

Met Ala Ala Glu Ala Glu Gln Gln His Gln Leu Leu Ser Thr Ala Val
  1               5                  10                  15

His Asp Thr Met Pro Gly Lys Tyr Val Arg Pro Glu Ser Gln Arg Pro
             20                  25                  30

Arg Leu Asp Leu Val Val Ser Asp Ala Arg Ile Pro Val Val Asp Leu
         35                  40                  45

Ala Ser Pro Asp Arg Ala Ala Val Val Ser Ala Val Gly Asp Ala Cys
     50                  55                  60

Arg Thr His Gly Phe Phe Gln Val Val Asn His Gly Ile Asp Ala Ala
```

-continued

```
65                  70                  75                  80

Leu Ile Ala Ser Val Met Glu Val Gly Arg Glu Phe Phe Arg Leu Pro
                85                  90                  95

Ala Glu Glu Lys Ala Lys Leu Tyr Ser Asp Asp Pro Ala Lys Lys Ile
            100                 105                 110

Arg Leu Ser Thr Ser Phe Asn Val Arg Lys Glu Thr Val His Asn Trp
        115                 120                 125

Arg Asp Tyr Leu Arg Leu His Cys Tyr Pro Leu His Gln Phe Val Pro
    130                 135                 140

Asp Trp Pro Ser Asn Pro Pro Ser Phe Lys Glu Ile Ile Gly Thr Tyr
145                 150                 155                 160

Cys Thr Glu Val Arg Glu Leu Gly Phe Arg Leu Tyr Glu Ala Ile Ser
                165                 170                 175

Glu Ser Leu Gly Leu Glu Gly Gly Tyr Met Arg Glu Thr Leu Gly Glu
            180                 185                 190

Gln Glu Gln His Met Ala Val Asn Tyr Tyr Pro Gln Cys Pro Glu Pro
        195                 200                 205

Glu Leu Thr Tyr Gly Leu Pro Ala His Thr Asp Pro Asn Ala Leu Thr
    210                 215                 220

Ile Leu Leu Met Asp Asp Gln Val Ala Gly Leu Gln Val Leu Asn Asp
225                 230                 235                 240

Gly Lys Trp Ile Ala Val Asn Pro Gln Pro Gly Ala Leu Val Ile Asn
                245                 250                 255

Ile Gly Asp Gln Leu Gln Ala Leu Ser Asn Gly Lys Tyr Arg Ser Val
            260                 265                 270

Trp His Arg Ala Val Val Asn Ser Asp Arg Glu Arg Met Ser Val Ala
        275                 280                 285

Ser Phe Leu Cys Pro Cys Asn Ser Val Glu Leu Gly Pro Ala Lys Lys
    290                 295                 300

Leu Ile Thr Asp Asp Ser Pro Ala Val Tyr Arg Asn Tyr Thr Tyr Asp
305                 310                 315                 320

Glu Tyr Tyr Lys Lys Phe Trp Ser Arg Asn Leu Asp Gln Glu His Cys
                325                 330                 335

Leu Glu Leu Phe Arg Thr
            340


<210> SEQ ID NO 12
<211> LENGTH: 815
<212> TYPE: DNA
<213> ORGANISM: Juglans nigra

<400> SEQUENCE: 12

gaggatgaga gacccaaggt tgcttacaat caattcagca ctgaaatccc catcatctcg      60

cttgccggga tagacgaagt ccatggccgg aggaccgaga tttgccagaa aatcgtcgag     120

gcctgtgagg actggggtat tttccaggtg gtcgatcatg gcgtcgatgc cagtctaatc     180

tccgacatga cacgtcttgc ccgtgacttc ttcgccatgc ctcccgagga aaagcttcgt     240

ttcgacatgt ccggcggcaa gaagggcggt ttcattgtct ccagccatct gcaaggagaa     300

gcagtgcaag attggcgtga aattgtgaca tatttctcat acccaattag gaccagagac     360

tattcgaggt ggccggacaa gccagaaggg tggagaaagg tgacggagga gtacagtgac     420

aaattgatgg gactggcatg caaactgttg gaagtgctat cggaggcgat gggattagag     480

aaggaagcat tgaccaaggc ttgcgtggat atggaccaaa aggttgtggt taattactat     540
```

-continued

```
ccaaaatgtc cacagccaga cctcacattg gggctaaagc gccacacaga tcctggcacc    600

atcactctgt tgttgcagga ccaggtgggt gggcttcagg ccaccaggga tggcggcaag    660

acctggatca ctgttcagcc tgttgaagga gctttcgtcg tcaatcttgg agaccatggt    720

cattttctga gtaacgggag gttcaagaac gctgatcacc aagcagtggt gaactcaaac    780

tacagtcgat tgtccatcgc caccttccaa aaccc                               815


<210> SEQ ID NO 13
<211> LENGTH: 815
<212> TYPE: DNA
<213> ORGANISM: Juglans nigra
<220> FEATURE:
<221> NAME/KEY: CDS
<222> LOCATION: (1)..(813)

<400> SEQUENCE: 13

gag gat gag aga ccc aag gtt gct tac aat caa ttc agc act gaa atc       48
Glu Asp Glu Arg Pro Lys Val Ala Tyr Asn Gln Phe Ser Thr Glu Ile
  1               5                  10                  15

ccc atc atc tcg ctt gcc ggg ata gac gaa gtc cat ggc cgg agg acc       96
Pro Ile Ile Ser Leu Ala Gly Ile Asp Glu Val His Gly Arg Arg Thr
             20                  25                  30

gag att tgc cag aaa atc gtc gag gcc tgt gag gac tgg ggt att ttc      144
Glu Ile Cys Gln Lys Ile Val Glu Ala Cys Glu Asp Trp Gly Ile Phe
         35                  40                  45

cag gtg gtc gat cat ggc gtc gat gcc agt cta atc tcc gac atg aca      192
Gln Val Val Asp His Gly Val Asp Ala Ser Leu Ile Ser Asp Met Thr
     50                  55                  60

cgt ctt gcc cgt gac ttc ttc gcc atg cct ccc gag gaa aag ctt cgt      240
Arg Leu Ala Arg Asp Phe Phe Ala Met Pro Pro Glu Glu Lys Leu Arg
 65                  70                  75                  80

ttc gac atg tcc ggc ggc aag aag ggc ggt ttc att gtc tcc agc cat      288
Phe Asp Met Ser Gly Gly Lys Lys Gly Gly Phe Ile Val Ser Ser His
                 85                  90                  95

ctg caa gga gaa gca gtg caa gat tgg cgt gaa att gtg aca tat ttc      336
Leu Gln Gly Glu Ala Val Gln Asp Trp Arg Glu Ile Val Thr Tyr Phe
            100                 105                 110

tca tac cca att agg acc aga gac tat tcg agg tgg ccg gac aag cca      384
Ser Tyr Pro Ile Arg Thr Arg Asp Tyr Ser Arg Trp Pro Asp Lys Pro
        115                 120                 125

gaa ggg tgg aga aag gtg acg gag gag tac agt gac aaa ttg atg gga      432
Glu Gly Trp Arg Lys Val Thr Glu Glu Tyr Ser Asp Lys Leu Met Gly
    130                 135                 140

ctg gca tgc aaa ctg ttg gaa gtg cta tcg gag gcg atg gga tta gag      480
Leu Ala Cys Lys Leu Leu Glu Val Leu Ser Glu Ala Met Gly Leu Glu
145                 150                 155                 160

aag gaa gca ttg acc aag gct tgc gtg gat atg gac caa aag gtt gtg      528
Lys Glu Ala Leu Thr Lys Ala Cys Val Asp Met Asp Gln Lys Val Val
                165                 170                 175

gtt aat tac tat cca aaa tgt cca cag cca gac ctc aca ttg ggg cta      576
Val Asn Tyr Tyr Pro Lys Cys Pro Gln Pro Asp Leu Thr Leu Gly Leu
            180                 185                 190

aag cgc cac aca gat cct ggc acc atc act ctg ttg ttg cag gac cag      624
Lys Arg His Thr Asp Pro Gly Thr Ile Thr Leu Leu Leu Gln Asp Gln
        195                 200                 205

gtg ggt ggg ctt cag gcc acc agg gat ggc ggc aag acc tgg atc act      672
Val Gly Gly Leu Gln Ala Thr Arg Asp Gly Gly Lys Thr Trp Ile Thr
    210                 215                 220

gtt cag cct gtt gaa gga gct ttc gtc gtc aat ctt gga gac cat ggt      720
Val Gln Pro Val Glu Gly Ala Phe Val Val Asn Leu Gly Asp His Gly
```

-continued

```
225                 230                 235                 240

cat ttt ctg agt aac ggg agg ttc aag aac gct gat cac caa gca gtg      768
His Phe Leu Ser Asn Gly Arg Phe Lys Asn Ala Asp His Gln Ala Val
                245                 250                 255

gtg aac tca aac tac agt cga ttg tcc atc gcc acc ttc caa aac cc       815
Val Asn Ser Asn Tyr Ser Arg Leu Ser Ile Ala Thr Phe Gln Asn
            260                 265                 270


<210> SEQ ID NO 14
<211> LENGTH: 271
<212> TYPE: PRT
<213> ORGANISM: Juglans nigra

<400> SEQUENCE: 14

Glu Asp Glu Arg Pro Lys Val Ala Tyr Asn Gln Phe Ser Thr Glu Ile
  1               5                  10                  15

Pro Ile Ile Ser Leu Ala Gly Ile Asp Glu Val His Gly Arg Arg Thr
             20                  25                  30

Glu Ile Cys Gln Lys Ile Val Glu Ala Cys Glu Asp Trp Gly Ile Phe
         35                  40                  45

Gln Val Val Asp His Gly Val Asp Ala Ser Leu Ile Ser Asp Met Thr
     50                  55                  60

Arg Leu Ala Arg Asp Phe Phe Ala Met Pro Pro Glu Glu Lys Leu Arg
 65                  70                  75                  80

Phe Asp Met Ser Gly Gly Lys Lys Gly Gly Phe Ile Val Ser Ser His
                 85                  90                  95

Leu Gln Gly Glu Ala Val Gln Asp Trp Arg Glu Ile Val Thr Tyr Phe
            100                 105                 110

Ser Tyr Pro Ile Arg Thr Arg Asp Tyr Ser Arg Trp Pro Asp Lys Pro
        115                 120                 125

Glu Gly Trp Arg Lys Val Thr Glu Glu Tyr Ser Asp Lys Leu Met Gly
    130                 135                 140

Leu Ala Cys Lys Leu Leu Glu Val Leu Ser Glu Ala Met Gly Leu Glu
145                 150                 155                 160

Lys Glu Ala Leu Thr Lys Ala Cys Val Asp Met Asp Gln Lys Val Val
                165                 170                 175

Val Asn Tyr Tyr Pro Lys Cys Pro Gln Pro Asp Leu Thr Leu Gly Leu
            180                 185                 190

Lys Arg His Thr Asp Pro Gly Thr Ile Thr Leu Leu Leu Gln Asp Gln
        195                 200                 205

Val Gly Gly Leu Gln Ala Thr Arg Asp Gly Gly Lys Thr Trp Ile Thr
    210                 215                 220

Val Gln Pro Val Glu Gly Ala Phe Val Val Asn Leu Gly Asp His Gly
225                 230                 235                 240

His Phe Leu Ser Asn Gly Arg Phe Lys Asn Ala Asp His Gln Ala Val
                245                 250                 255

Val Asn Ser Asn Tyr Ser Arg Leu Ser Ile Ala Thr Phe Gln Asn
            260                 265                 270


<210> SEQ ID NO 15
<211> LENGTH: 105840
<212> TYPE: DNA
<213> ORGANISM: Oryza sativa

<400> SEQUENCE: 15

gaattccata tgccgtacgt cctctttgtt gtacgattat tatacgtgtt ttatttttga     60
```

-continued

```
acgaacatta tacgtgtttt tgaagtgtac gcgcgttaac aaaagaaaag cttcatggtg    120
atttcgtaac atgtcaatgg gaacaaaatt gctaatccaa attaaagcca tatattaagt    180
ttctacaaaa aaaaaacgaa ataagttgct aattgagcat ctgattatat gtctgatact    240
taccgaaaac gaacaatgct acagaataaa ttaaatgcaa ctcaagctac cttatatata    300
tagaagttaa gaatatgaga atcccaatta taccgcggtg agagcttgag catcgtcacg    360
aaaccggcaa acattcttct gcaagtagca gatgacgtac gtacgtgttt gattcttagc    420
cttagttcgt tagaatatgc tgcacttgca agctacacta gctactaccc ttttcctttt    480
tattcttctt tttcgaaaaa aagggaatca agtcgttaat cttcctcact ttcatctcat    540
cctttctaac aattcaaaca gatcatacta tcatgcttta atgtatagga gcgaatttta    600
gattaggtta tttgcaggac taagttccct atttcaatat atattcggtt cgatgcagag    660
accgggtaaa aaaaataccc ttctctaaaa aaaatcatgc tcgaatgcat gcatgttaat    720
caaaatatac tgagattggg atggatttat atatgtatga tgatggagtt ggaaggggtt    780
aatttgattt ttacgtacgg gtgaaggaag tgctcgaaga gccaggcacg gaggatggag    840
acggcgcgct cggggaggcc gcgctggggg cgccatgggt ggctctcgag catgccggcc    900
tggtaggcct tgtgctggcg gaggcactgg tcgagcaccc ggaggcgggg cgtctcgccc    960
ttggtcatcc cgggcaccgc cgtgtccttc tccccgagct gcttccgcac cgcctgcagc   1020
tgcgccacca ccccgtccct caggctccgg aagtgcctcg agatcgtcct cgacgccagc   1080
cgcgtgtacg acgccgccgc cctctccccg gccaccgcct cgaacgacgc cgcgagcgcc   1140
ctcatctgct cgcagtacct cctgtacctc ctatccacct gcataataat aattaagcaa   1200
gagtaatttc agcaactaat taatcgagat gattacaatg gaaatatttg atgacactgt   1260
gtagcttagt aggtgtagct ctacttgctt gtactactgc ccggaattct gcaacgacca   1320
agctgcacct acctgtgaac tccactgtac tgatgagcag tgtaatcaca agaatggcaa   1380
gcaataagca gtgagtaaat gtctgaggaa ttaattgaga gatcctggtg gaggcaggag   1440
caggggatgg gcatgcatgc caagtccaaa gggattgaga gctaggaggc ctagcagtag   1500
gctgcataga tctacagtag gctgcataga tcgagagcta gctagctaag ctgcaaccct   1560
actactacac ctacagtgcc atggccatgc ttggagagaa aaggagagga gagagagaga   1620
attccctata gagataccta gctacaggtg tagctaaggc aaaggaatgg aggtttccaa   1680
aagcgaatgg tgaggaccaa gaagggaatc ccctccctgt gcttgtccca ggaaccctcc   1740
ttgggcaagc cataattgaa ctgccacttg cctgcagctt tttagatttc caaggagaga   1800
cactctctca tgctagcttt gcttaaatta ggcctccttg ccatggtggt gtgtgtggtt   1860
aattagctaa gcttgagaag ctctcacctc ttcgagcatg gtgtagagct tgcccttgag   1920
ccgctgcagc tcggccgcgt ccatggactg gatctgcgtc ggcgcggtcc acgacgacga   1980
gcctccgccg ctggcggcct cttcttgcgg cggtttggtt gccttgcttg ccgatgatgg   2040
gctggtggtg ctcttcacgg ggaggctgca gaactcctgc aggagctgct gcgtcgggag   2100
gaggaacctt gagccgcgga gatgccacgc accctgctgc agctgccacg tcgacgccgc   2160
gcccgccggc ggcgacggct ggtggtggag gtgctgctgc tgctgctgca tcagcagcga   2220
cgtcgcggcc gcctccggcc tgtggagcga gagggacagc ggcgcctggc tctgccggtg   2280
ttggtggtgg tgcagctcgc cgagcccgcc gaagtggacc gtcggcagcg tcgtcgcgcc   2340
tccatcatcg acgccgccgc cgccgacgac gagcgcgccc acacccttgc tctgctcgtg   2400
cgcgtgcgct gccggcatga gccccctcac cccgaacatc tccgccaccc caaccccctg   2460
```

-continued

```
ctgatgctgc tgcaacccat acaactccgt ggcgccggtg ccatccacct ccgccgcgaa   2520
gtaatccgcg taccctaggc tcggatcgtg cgccatggat atcgatcaaa tcacgcacga   2580
ccacctcgag ccgtggcacg cgagagctca ctctccctcg atctgtggcg gtgcggggat   2640
tggtgaaaag gcgaaaagct gagagcaaca aaagtggagg aaagcaagag aaggtcgagg   2700
tggaggagag gagagatgag ctatagctaa gcctaggaag ggaagcgcac cgagaggaaa   2760
gggagagaaa ataaagggga gaagcaaagc ttaggtagat agatggatgg atagcccggg   2820
gaagggagac gcacgcaacg gcagtgcaac tttgcgcaaa ggagaggggg agctaggtgt   2880
agcaggacca tatctttttt gggaggagag agagttggga gatatgggaa tatgtgaccg   2940
agctactctg atcctgtttc aaaatataca aacctaatat tatcaagaat ctgaattggt   3000
ttgggatgca tcatattcta ctctatgata gaggaagtag cttgtatgta ccgctcatat   3060
attctgctgg ttgctggtgt gtgagacgag atcacgttta gttagttctc gtttacacac   3120
ggggagacac ataacacggg taggatcatg atcctcaact tttaaagtca catgattttg   3180
tcattgatat ataggcccga tgagccctag actcatatat aagtgataag ggtataaaga   3240
tttcgaagat ggaggatctc aatctgacat aggtagggtt ttgatttaca ttttgcaatg   3300
aagagaaatg aagggaccaa aatccaaaat ttaggatgtt ctgagccaaa cttaatttaa   3360
cacaaaacca atttcaaaat ttgcacattt tttccatgaa tagatcaatt gatggctaaa   3420
cgcaaaattt cctccgggaa catttcgggg cctcacccgc atacatgatg tgtgctagat   3480
atatgagaaa aaaatacata cggtattaca gtaagtgtat ttttttttat cattcgacag   3540
gatgccaaaa caagtggtta ttatatctcc agggattaaa agagtttctc cgtacacgct   3600
caggcacata caaaacgaag cacatatcga gagagagaga agaacaacaa aattaatgag   3660
caactcgcaa ccagtcgatc gatcgatcgg ttgggggcgg tggttgcggc gtaagcttcc   3720
gatcgatcgc gcgctatagc tgcaggatag cggcttcacc cggcctgccg ctactcttgc   3780
accgttgcac tgtagctata cgttgcattg catgcactgt cctgtgctgt tgtgcacacc   3840
acacatgtac gtacagtgta cctgtggatt tatttttatt tatttattta ttgctgatgt   3900
cttctttttc ttcttatggg ataatcacga gagccagatg tagcttcaat ctctcgctcg   3960
agaaagtgga tgcatgcatg gatgtgtcat gtgtattttg caggctcgcc ttttcgctta   4020
tgtttatgtt tatcagaaaa aaatataaat tttcaatctt aaatttgagg ttgattttga   4080
agtttttuca tcaaaattta tttttttgtc tttgcttttt aaaccgttaa gaacacatat   4140
ataaaatttt tattcacaaa ttattttta tttacaaata tatcgtttgg tttatttcct   4200
agataagcga aacgataggg accttggtct aaaggagctg agctctcacg agctcataca   4260
cagtgtgaag tgtgagacaa taattttcta cacctaaata atggtatgcg tcattaattt   4320
acaagctact taaatagtta tgaacttttt tagaaaaaca ataatattaa ttgcgatgat   4380
ataagtttat aaaatatgac aatatttgat ctataattaa aaaaaagaat ttatggcagt   4440
gaatagtacg gccgtgtgcc tgtgtgcagt gtacatgaca tgcttgttgt gtgcttgaac   4500
gcaaaaaaaa gcagaggaga gagtgagcga ggtagtggtc caaggctacc aaccaatgac   4560
aatttgtaga gcggcctatt ggaaaacagg gtgaacggtg gggaccacac gtgggcccca   4620
caggagggcg tgtgggacca cctacgtcac aatcgtgcat ctttcttttt ttttaatttt   4680
attttctcct tcttctcatt tttaattact agtagtccga tgatgaaatg tatatattgc   4740
atatatcttc aggagtattt ttctgccact cgtgcgaacc aaccagagta aaagattggt   4800
```

-continued

```
gtggagtgga ctagtagtct agtgatggaa ttcatcggtc acgttctacg cacgtgtttt   4860
catatcgagg gccgtcgatc gtttggattg caggatattt tggacgaaaa tcatgcgaaa   4920
tgatgatgcg ttgcaatcaa atgagaggca aaaaaaaaaa ggcttggctg tttgcgtcat   4980
agcctgctca aacaattcct cgcgtaaagt acagttcata cttcttgata ctgtacttga   5040
ttacccgtct attcctctta actaactttc cccatcaacg ctgaggaaca tgcatggcct   5100
aatatagtag gggatgatat atgagctaaa gtaatttaca agttataacc atttaaaatg   5160
atcagaatta taaagagaaa acactcactt ttgtatcaat atataggata ggggagaagg   5220
tgtaaaccta aatagggaag aaaccggatc ggttatggtt ggatcatggc attccgcata   5280
ttcttaccta tatttttctt tgaatccaga acagggtacg gatagtggca gatatataac   5340
atatcactta ggagtatctt gtatcctatc caatattttt ttccctagaa tcagaagcgg   5400
aaaatgatat ttatctgcag ttcataggta ttaaacctag ggagacaatt acagtgttta   5460
aaaagatata tcaaaagaaa aggtgtgcaa tatcactgtt tcatcatggt tcattacaag   5520
cttaattaat aaaaaattcc aatcatgctc ctgacagttt ttcaatgcct tgggtgttct   5580
tgaattttgc tcatccccta tgtacagttt tccctctgac ctcctatatg tctatttcct   5640
tagttgaccg ttagaatttg tcaggactat atcacctctt ttagatattt aagattataa   5700
gaaacagctg gtgtgtacta tgtagtcagc tgataaaaat ctagaaaagt tatatttcct   5760
agcttatgtg ttttattttt ctttctggtt tatataatta tagtttctta agattgaatg   5820
agaatatgca tggattatgc atggattatt tgaagagtta aaagatactt agaagaagtt   5880
gcaactacta tgagctctcc aaacacgata aaaaccactt aactagaaag ctcgtctgaa   5940
tcaaagaaaa aggattagtg ggacaaagaa gcacttgatg tgcttgcatg catctttaac   6000
aactgcgacg gatgcaaata attaaccatt tgagaaaacc aaccaaatac agcataattt   6060
ttttaatata tatgggtcga caatgatgtc gaatatatat ttttcaatat gtctacacgc   6120
gcgcgccagg aaatgaccct atcagtcctc gtcaacacat ataaacttgt ctttgaagtc   6180
tcaatttcct tcactttaaa actctgcaga aaattcaatg taaacaaaac ggatcgttct   6240
aaaattttaa aaagtgtctc agtggggctc actccatatt taggttaatg cagttatata   6300
ctccgggttg tacatgtccc tttctccaaa gtttcccgtt tcattttttta atcaccaaat   6360
ctgatcattc cccctaaccc ctttctcaat cctatcatgc atataattat atttttacat   6420
ggcatcaaat acaatatttg tcattgaact tgagatagct agcatcaccg attcttccta   6480
ccagattcca agtatcaatg cacgcattgc gcacacttgc cactagccag aggaacagaa   6540
ttagtactac taattaacag tggacttgaa ttttgcatga aaaaattggt ttaacccccg   6600
aaataaaata tcctaattga cgtggtgatc cagataagac aaattttagt aggttgctat   6660
tttggaactt cgtagtacta tctgttaatt agtttaaggg caattacatg gttaattaac   6720
tagttgcatt tgcataccca tgcatgagct gcgctgacgt aagctgggaa actgcatgta   6780
gtacatttcc aatgtctatg aaatgtgggt cctggtatat attagtcatc tcagtggggc   6840
ccacaatcgt ttgcttgttc acacacttca tgttgctagt taaggtaagt cactgatctg   6900
tttgacctca cagaaaacca aagctcacga tcgaaaaccg aagatattaa taataacata   6960
agtttggaat gatgaggaaa atcgctattg acttgagaaa cacagtgtaa atgcaaatgt   7020
ttacaacgcg cacacattta tttgtatgaa cacacgtaca ttttacaacg cacatgtaca   7080
attttgatta tatacatgtt tgtgtattac aaaaggcaca attatgaaat tcaagtttca   7140
catcgaattt atgttctctg cgcatttacc tatccctaga gtggttatat tttctatttg   7200
```

-continued gtccatgatc accccacata aagcaatggg tttacttaaa acaacatact acctccgtct 7260
tttaatgtgc gacatcatta acttttaaca tacgtttaat cttattcaaa gttttatgca 7320
cacataaaaa atgagtcatc attctcaaat aacttttaat aataaatcaa gtcaccacaa 7380
aacaaataat aattaattat ataaatattt tttaataaga tgaatgatca aatatctctt 7440
aaaaagtcaa atgcgttata tatttaaaaa gagaagagaa taataaatac tccatccata 7500
ctaaaatata aaggattttg atcggatatg atatattgta gtattatgaa tctggacata 7560
cttctgtcca gattagtagt actagaatgt gtctcatccg aataattttt tttatatttt 7620
aggacggaag gagtagtatg tcatcttgcg cttaaaataa aactgtctcg cttgttgcta 7680
gaatagactg caggcaggga cagggatgga gaagtagcag agtacatttc tgtcatccaa 7740
acagaagttg ttagagatag gtacatatat gtagtaccag gggatattta catcttgcct 7800
ggatctccca cctcaagaga gagagagaga agaattcttt gtgagccttt gatgatccaa 7860
aagagcatct tggaagtttt gtacatgcag atgcatatgt gtgcatcgac ttgtgagact 7920
tgcaagtcag tctggtcttt caagctagcc aagtcacagt actagtcatc ttcacaaatt 7980
gaaaattcgt ccatgtctag aaagggtgtg gttggaatcg gatcacgacg gatactatta 8040
tgtgtaggta gtaaacatga cttggaagtc agagaaaata aacaaacatt tatagatcga 8100
tcagagaaga tgatggatcg atcacacagt gccactacgc tggacccact caccattgac 8160
gggcccatgt catcaccttt gatgaattta gccctcgtca gagattagtg gtcactgatg 8220
actgcacctc acatctgacg ggtgaaaagc cgtcagtggt gattaacacc tttgacgggc 8280
cgcatagaaa tagcccgtca caggtgagaa tcacttgtaa cgggtgactc tttccagccc 8340
gtcaaaggtg acatacacct ctgacaggtc taatttatca cccgtcacag gtgtgaaaaa 8400
tcatcaaaaa aaaattcaaa agtcctcagc ccccagccac cagctcccag ctcacgacat 8460
gaagcaaaag atgcaagatt catctcaaga tgcaagacaa caactttgca tttcattggc 8520
atatctgata acatcagaga aacaatatag atcacacaac ttgagtaaca atatacatca 8580
cagtagtaat gatctgcatc ttaacaaact agacatccac acaaacaaca cagaatatgg 8640
cccaatctaa aatttggcaa tgaacatttg caagataaga aaaatcaagc acaacctaca 8700
agagtcagaa atggcggtgg cgctcgtggg tgaaggagac ggtggaggac gccgatggtc 8760 gggggagag ggcgtggaca ccggcggttg ggggatggag gctgcggtag ccggatccac 8820
gtaccagaac cccgtggagg ccggatccag cggcggctgt tgggtgggcg ttggaaggcg 8880
acgcgggcag atccgaggtt tgtgggcgta gaagctggtg gcgccgtcga tggaggcggt 8940
cgcttgtcgt cttcatcgca gccgccgtca aaatcgtcgt cgtcgttgtc gcagctaccg 9000
ccgccatggc cgctcgctcc tgcccgccta agcccaccgc cgccgcttcc gagggcggag 9060
acgggcagat ctgctgccgc ccgagccgcc gccgcctccc ctcccgccgg atctggcgga 9120
ggggagggcg ccaccgcctc ccttccctca gtcgggcctc cagatctggc ggagggaagg 9180
cgctcccacc atccacgccg ttgcacctcc acgccgtccg ccgccaccac gcctcccttc 9240
ccgcgcctcc cctctcgccc ctgccggatc tgacgagatg gcgccgccgc ccctgccaag 9300
ccggcgccgg tgccgctgct acacgcagag aaatggagaa agggagagag aactcgagag 9360
aaatggagaa agagagagag aaaacaacct tatctcttct gagtgtgggc ccagccagga 9420
gaagaaatat ctcctccggc tcggcttggg aaggtaggtg acagcttcga gtatatatag 9480
tgggacaact cacctcaaac ggtttagggt ttgaacccgt ttgtaaaccg tttgaggtga 9540

-continued

```
gtaaacctca cctctgacgg gccatccggt tgcaactcgt cacaggtaac tagtcacctg   9600
tgacgggccg gaagtagaaa ccgtcagagg tgaggattaa ctcacctttg acgggttccg   9660
ttttcgaccc gtcacaggtg actagttacc tgtgacgggt cgtagctgaa tagctcaccg   9720
atgacggaat cttttagaac ccgtcaaagg tgaccatcat cactgactac cacttatgtc   9780
cgtcacagat atgtcgtcac aagtatgagg atctggtgta gtgtgccata ttaggcgaag   9840
catgccaatc aatcagttga tgttccccat ctcgtttaat tagttaagga taatatcttt   9900
ttcttttctt ttcatttctg attctctgat cagttccaga aaaagaagct ccagagtatt   9960
ggctatctgt tctgcagtat ctgtatatga agttagtgtg cgttccaagt tgccgtgctg  10020
ttcatatata aacatcatcc ccatccaaca aatgatgatc gatgcgcctt aatctcacat  10080
atatatgacc gttgcatgca tgcagatatg atgtagctag acgactacag tactgcacgt  10140
acggatcatc gtcgtcgtcg tctctgcttt gattgatcga tgaattattg cttgctcctt  10200
gctggtaatt aatctgtttg cttccgtcag aagcagagaa agaaatggag aggaattaac  10260
cacggagtag tgtgtctacg tcgatcgatt taccaccgca gatcgagcaa agagacgatc  10320
gaatcgaaga cgattccaca gctcgatcgc tagctagcta agctctgcag ccgtcggcac  10380
caaagactat tccgccatta ctgcctttcc gagattttta gccccatcgc catggggcct  10440
acgaatggaa cagccaggtt gatggagatg gatgcagata gagtcatgca gcagctatag  10500
ctagcactag tcgtcgatca gctataccgg ttttatctag ctagatttgc taaaagaaga  10560
atatatataa tcctcgatcc acagctaaat acattgagac atgagacact tactaaacgc  10620
atcattatcg tcccaagaaa tgacagtaac gcacatataa tttcgattca ttattgctag  10680
ctaggtggag acgtacgtag actctcactc gagtacttga cctgtagctg ctaggtcgct  10740
gctactgctc ctctctccgt gtctcttgga ggaggaagag gaagaagaag gaagctagca  10800
gccggagctg tgcttttcga ccgtgcgatg ccgttcttgt cagtcgcttt tgcgagagtt  10860
actgctgtag tccgccctac gtacatacga caagtcatct catcgttttc tcgttggttt  10920
atcgagtaac caaagttcaa aatttaaaac cttttttat tattttaggt tgatctttgg  10980
gttttaattt ctatcgttgt caatttttgt acatttagct attactcttt tctatataaa  11040
ataaattaaa acctgaacac tacatccacg tagcggatat acacaaccaa caaaatacag  11100
tatttgtata gataatacgc accacaaaaa atatttagat tcaaaaccgc cgcttaaaag  11160
aacgagaatg ctaggggacg ggatactgtc ccccaacagg atactcctct accacaatac  11220
gattcttata catacacgca ctaggcctac tcactcgccg ccgtcgccgt cccccaccgc  11280
cgccgtgccc gttccccgtc gccactgccg cgcccatccc ccaccgccgc cgtcccgtac  11340
ctgtcccctg ccgccgccgt cgccgtcctc gtctacaggg gacagctgca gggggcgacc  11400
gcgcgtgtcg ggatgctcct cccaaacagg atgcccggtt atatctaata ggaatcacct  11460
gatacctggt aggtatcatc cgatacctca caagtatcac gcgatacatg gtagaaatcg  11520
tctgatacct gataagtatc atatgatacc tggcgatatc acgcgatacg tggtagaaat  11580
cgctgataca tgacaggtat tgcatgatac ctcgtgagta tcacgcgata cgtggttgaa  11640
atcatctgat actgtaacgc tccgcttttc gtgagacgtt aaaaactaat tcgccaaaat  11700
cctatatgcg aaaatttcgt tatttgtgtg agagtctaag ttgtgccaag atctcaattc  11760
aaatctccat tgttgttctc tcccgtcgcc atcaaaatcc tccacctcta aaatgtcaat  11820
cccgattcat cttccaaagt caaacatcga aattcaatcc catccttgaa attccttgcc  11880
aatatttctc tcgattccaa gaatatcaaa tcccaacctt gaatccctcc ctgtctatcg  11940
```

-continued

```
atctatctac ctgttcatct atctatctac ctatctatcc atccatctat ctatctacaa  12000
gtttatccat cggttcgtcc gtctatctaa caacctttga attcctgtcc caactccaag  12060
gatgtaaatc caaacatatc ccagccttga gctttaacct ccaagattcc tcctttttcc  12120
tctttctttg gaaacctccc caaataattc ttcgggtctc cagatacaaa accaattcga  12180
aaatattgag ttttcacttt gatctccctt ccttgactcc accatattcc gatgagtcca  12240
aatatcaagt tcaaaattca aatttcaaat ctcaatccct tcataatcaa tctcctcggt  12300
aaaagtctat tttgcctccc tctttgtcgt tgggccgatt cttcctccct cggcccatct  12360
cccctcccag ccttcctctc ccccctctc acgtgcgcca cacgtgcctg ctcagccgag  12420
cgagagagag gcagcgcctc tcttcttcct cgttctcttc tcgtctctct ctttctcacc  12480
gctccctgcc agcgcttcgc cgattcaaac tgccaccgcc ttcgctcgtt cccgcgcgcg  12540
ctcccgtcgt ggtggccgac cgccctcggt cgccgtccgc cctggcccgc ctgcgccgtg  12600
cagccgcccg tgcccactct gtcgtcgccc catctctgcg ccgttgtgcg cgtgcgtcca  12660
agacgtggag gcaaggcctc ggctccccac tctcacattc cctcccacct ccctctgctc  12720
gcccaaaccg gcaagggacc gagctccttt ccctccccct ttttgctttt tcccttccat  12780
cgccaccgtc acctcctctg cgcccgtgac cacccgccag ctcgcccctt gaccgcctcg  12840
tccaaggtcg gttcctcccc caaaccacct tccccgtgct ataaagccca agccgagtcc  12900
ccctccccat cccaatctct ctcgtttctc tcatcgccac aaccgcgcca ttgtcgcctt  12960
tcctctgctc tcgccgtcgc cgtccgctgc caagcaccgg ggaggccggt gcgtgcgagg  13020
acgcgtgacg cgggactccg ggcaccctcc tccttcctct tccctggccc gagaacggag  13080
agctcgctcc cgcgccgtcg gccgctcgac accgcgcccg ttccggctcg gtagtgcctc  13140
cctcccgttc cccttcctca ctcgccctct ccctccctag ctcacgtggt agctcggcta  13200
gccttccggt agttcgtaga agccgcccca agccccgccg ctacctggca tggcctcgcc  13260
gccattgccg cccgctcccg gaggttgccg tcattgccag ccctccacgg tgccgctcca  13320
ccccatccgg cgccggaaac gggttcccca actcccttgg atgctcccac cgccttgaat  13380
cgacctctcg tctaccgccg ccgtttcccc tctttgctcg tcgccggcat gcgccaccgc  13440
gattcgtcgc cgccggcctc cctccggtca atccgggccg gtgattccct ccctcttgtc  13500
cctcccatca ctccggtgtc ctccccctcc cttgaatccc cgtgtgctgc cccggcgaat  13560
gtcgccgccg tccgccgtcc atctcggcct ccccccttctt cctcctcccg ccggcccgcg  13620
tggctgcgac gaaggcacca cgtcggcacc agctcggccg gaccgggtca agctgacccc  13680
ggtcagccgc tccctccgta ccccgctcgc gcgcgcggtc caccgcgagc catgaggctg  13740
cacgtgggtc cgtcgcctcc tagtcctccg tgcaccgcgc cgtgcaccgc tccccctcct  13800
gaaccccagt gccgtccccg cgtgcgcctc cctcaccgtg aaccaggccg ccgccatgcg  13860
ggccccacgt gggaccccgc gaggtgaact tggtccaccg gactgctccc tctctcccgc  13920
gcgcccctaa tgggccgcct cctcgcgccc gcgtcggccc attttgttcg gccgagccgc  13980
aatagccttc aggccgcgcc ctagccgccc gaaggaagtc taaatgacat ccctctttcc  14040
ttttcttttc caagggattt aataaatcct ttttccccta ttccataaat caattcctta  14100
tttcaaaatt ccataagtca tttcccttga tcctgcacgt aagtggtagt caataatatt  14160
cttgagaata ttatttctat aaatttcata aatcaatttc cccttgttcc acaaatatct  14220
tccttcgccc agaaattcca cttaaacttc caaaattcat atatctcgat ccattcgtcc  14280
```

-continued

```
gatcgccccc gttcaatttc cagtaattcc gtaaaattga gatctatggc actattaatt  14340
agtctaaata gggtctttct tttggtcttt tggttaggtt ttcgattgtt tgcgtatagt  14400
cgcagttacc ggattttcgt cgatcgtgga tttctcgaag attcgtgaag cttagtgaag  14460
accttgagca aggaaagtca ccttttgatc atcttgcacc tataatttaa aactaagtat  14520
ttcatttccg caaatattgc atgaatagga tttacacaag taattcggcc gcggcttgcg  14580
agatagcctg ccggccccca attcctagtt gctgcaatta ccctccttga attattgaac  14640
acttaaacct cttttgtcag ctattgtgct tcgatgcatg ggccctcagg cacgcgcatc  14700
ggaacacctt ccctcaaatt taaaatatcc aacgatgggt aaaacttggg gttttataaa  14760
agacttggaa aaactcgaca cctgggtcgg tgtttgcgaa ctaaataaat ttccaaaacc  14820
gcagaccgga ggacgtaccg ggagtacggt ttccccgctc ttgcacttaa ggaccgtttc  14880
cttggaattt tattcgaaca taaggcaagt gcgaccacat gggtggaata ggacacccct  14940
ggctgagtaa ttagctaatc gggggagcca tgatgccaag agatatgtgg attcaacggg  15000
atggtgccgg ggagaacccc cgggcttcct ggcacagtat ggtctgggac ctaatctgat  15060
gtcggtctgg gacccctctc gttggcatat ggtgtttaaa taaaatcaat agcaaaaaca  15120
acagtcttcc cttgaagcat gcattaaaca cttaattccc atggcttgct gagtacgaaa  15180
gtactcaccc ttactctctc tctctctctc tctctatata tatatatata tatatatata  15240
tatatatata tatatatata tatatatata tatagtttct ctgccttgaa gagaagatga  15300
agtgaagcga agattagggt ttcgtcctgg ttcccagccg tcgcctgtgg tgattggtgt  15360
tagttcgtta gttctgctgc tgctgttgct gttggtgttt cctcgtccgc gtcgtcggtt  15420
gtattctcgg gctgtcctga gctgcaacct aagttaaggt aaataagtcc tctatttaat  15480
ttaaggattg caatgattca tatttgtcac cgtgggtacc agcgctatgt cctgggactg  15540
gtactgtgat cgcggtttcg taggaagcga ttcgcgtcgt ttttcctacg acacgctcct  15600
atcaggtgcc gttgtacggc ggtgccagat tggggtgtga cagatacctg acaggtttca  15660
catgatacct cgcgagtatc acgcgatacg tggtagaaat cgcatggtac ctgataagta  15720
tcacatgata ctttcaagta tcacctaaaa cgtgtgtaga acggtctgat acctgatagt  15780
tatcacatct gatacctact tgggatcatc ctgtgtgtat aattgtctga tacctaatag  15840
gtatcacacc tgataactat ttgggatcat tccgttcgaa aacgggattc cgttatatag  15900
cagcccccta aaaaaatcca ataattcaga tattaaagtt tcacgcaata cattttacat  15960
ttttttatta tttttctatg acttatcagc catagctcta ccgatagcga gtgtgtgtga  16020
gagagagaga gcgcgcgcgt gctgccgaag tgacggtcag ttgggacgtg cttgtcgatt  16080
gaagggagag aggcggatgt accaacggtc gacgacgtac cggccggcgc tgccgccttc  16140
ggttgcctcg tcgcgcctcg cgcgcgttgc cgatcgggag agagctcgca agttgcctgt  16200
gcgcgcgtgt ggcgcccaag cgatcctaag cttggcaccg tacgtgcaac gaccgcgcgc  16260
tccatgtcgg agagaatctt tgcctgcgag agagcgagct agcaagcggc tgttctcctg  16320
ttcctatctg gcgtggtcat gtacaagtct gtgtgtgtgc gtatggaccc atcaccacac  16380
accccaacat cggtcgcatg attctcatgg caaaattggg gatcgacttg ggatcgatat  16440
gggtacagct gatgctcatg tgagtggtgg tggatgaagc tatactacta gctggtgacc  16500
tggtgtgtgc gtgttgctcc tttttgtgta tggatcagtg gattgacacg actggcactc  16560
gtggagaaag catggggcgg gcgagacgga cgccgaggtt tgtagtactt ggttgcaccg  16620
tactatacgt ccgtacggtc ggttaattgc tgccatcggt tagttacgca catcggcata  16680
```

-continued

```
ggtcgactat tttaggcctg tatatatgga gaggattaat tatgtcagct gcagttttct  16740
ttttaagaga aaaaaatctt cagctctcta agcatgcaca ttgataagcc gtcaccgtca  16800
ggagcactgg tgcaccggta gtaaactaaa ttaaaaatag gtgcaatact gttgatacag  16860
tagcagtggc taagatgtgg gtctggactc acacgtcaat atctgtatca gcagtattat  16920
agacaattcc caccgattaa aaatagacat ccattttcag gtgatcaacg gagatgcatc  16980
cctgcagttg atctcgcgaa tgaaacggca tgcatacatc tcttgtcaac ttccagtggc  17040
aacagtactt gactttggtt gcatgcatgc gtgcagatgt gcagcagtgc aaagatcccc  17100
tgcagcgagc tcgatctggg gtgccacttg ctaacagtgc agattgcttg ccgacaggct  17160
gatgctgtcc atttcagctc agtcaaaaca ctgttcgttt ttcgatcgtg gagtacatgc  17220
atcatgtcat ctcgtttctt tttcttgttt ggatgaaatg gcaacctcga gtcttctttc  17280
cctttaattt ggtgccaaac tgccactggc cttttgtaca taatcctagc tggtttggtg  17340
agctttggac cgccaggttt gtagcatttt cctcctttta gactgacata gtttatggat  17400
aagactagcc gccgacggtt gtttatatac atctcgcacg ggacagggga tcagctagtg  17460
tgtatatatc agttgttatt gtttattgac aaaaatcaga acagcatatc tagccgtgcg  17520
tatatcacga aaatccttaa aatgcagcaa aatatataat tcctttatat cgagaaaagg  17580
aaaacaaatt tgaaaacata attgatctaa aaggactatt tgtgctaagc tataataaag  17640
ctctagtagt cgtactccat ctaagagaaa accaaccaga ttatagctct gggaccgaag  17700
ctatagtata agacattttg agtttggttt ggctagattt atatataaaa aaatcagtag  17760
catttctaac acacaataag gttgtgtttg ctaggagact ccacaacttt tacctcttgt  17820
ttttcgtgcg cgcacttttt aaactattaa ataatatatt tttaacaaaa atcctatata  17880
aaagttactt taaaatcata taatctattt tttaaatttt ttagctaata cttaactaat  17940
catttgttaa tcatatgctc tattttgcat gcaaggagcg agggctccca accctctaac  18000
gaacgcctat gtgtgaccta aatataaata tataaactgt ttcacaaaat ataacgtagg  18060
gagtaggtaa aactaactta tgaaatattg gtagtgtgca tttatttttt tgaaaaagtt  18120
ctgtatagat aatgcttgtt ctcaaatgtc ggtacatcag aagtttaaat tgacatcaac  18180
tcctaactaa aggaaataaa cgaattgaaa cttagtgggc ctaaatagta ctggacacgc  18240
aaggtccaat cagtaggctt gatatatact actataggct tgggccggtc atcttaattt  18300
aacgggtcga tctccaacat aaacttgagg attgaattaa agacgtatct caacaccgat  18360
ttaaaaatga aattaaaatg catatctatc atttttttca aaagattatt atgtgtttga  18420
gaatttatat tttgtgtcga aaatattgta cagttgggat agacatgcat aacagtgaag  18480
tagatgtata caatatacta acactatatt ttatctaact acaaaatttt gacatgtaac  18540
acaatcaatc gttctaagtt ttagtttcta agaaagtaca tgcatttatt tacaaattcc  18600
gacgggcctt cgtaaacttt gaccattcat tatgggcccg aattggctat attggcccat  18660
gctctgttga tatacacatc aggacgggca ggcagtgtga gagttcagac aacatcacta  18720
gacgtatgca ggtccgtttg gatatgaaac caactactac gctcttcgtt tcaaaatgta  18780
ataatttaag agcctattcg gttcacagga tttttaaatc acaggaatag aaaaaatgta  18840
gtaataatat aggaatgcac gtgcaaaaca atggattgga acacatgaat tttttctaca  18900
ctgagctaaa caaaagaggt tggagtggat attttcattc ctatggaatt agtacatttt  18960
ggaggattgg catagtgttt ctacggaaaa tttttctttg aatcctacaa atcgaatgca  19020
```

-continued

```
tgaacagtgc ttattctaga ggaattgaga ttttctttag gagtccttga aaataaataa  19080
agtcttaaaa agtttagatt tatagtatta aaatgtaccg tagaaatgta gtaaaaggtt  19140
tgttagagaa gcctgtggct gtggctgttc tatacatgca cgtcagcata aagtcagtgg  19200
actataggct ccatccatgg cccacgtgca gtgaaacggg tgcaggattg gtgggtgtgt  19260
acgtgtttgg aatgagctgt tcccaacata tccacagtac acacggaaaa catagcggtc  19320
tattagtgag agattaatta agtattagtt attctttttt aaaaatggat caatatgatt  19380
tttaagcaac ttttgtatag aatttttttt aaaaaaaaac acatcgctta gcagtttgaa  19440
aaatatatgc gcgtggaata agatggagag gagttggaac ccataattcc aaacacagcc  19500
ggcaccgttg cagatttgat ccgacggtca aaatccacct ggagcccatc ggacggacca  19560
gacacgcgat cagcagcagc actcgagaat cgccgtgaag cgtccgagac aagcttcctt  19620
cactctctca caaattaact ccggcctcag cctcctccca ggctctcaac tcagctaccc  19680
actccggcga gcatggcggc ggaggcagcg gcgcgcggag agggccacga cgacggctac  19740
ttccccattc tcgaggtgcg tattctggat gaggcgtggc tgcgaggggg cttgtggtgg  19800
aggaggggga tccgggggga gcaggggtta gccatggcga tggcgcagca gccaggcaat  19860
gtcaatgtgg ctgggttctt gcaggcttcg aggaggctga ggaatcgggt gatcatgatg  19920
ttgtggatgc gtatgcttct caggcagctg gtcgtgagat ggtggctgcg cgtgcatttc  19980
aggcggttca tgtgggtgtg gcatctgcgg gttcttcggg ctcgggttcg tctgtttctt  20040
tggaggattc ggcatgacca ccttgtctac atcttggaca ccatcatggt tttggcatac  20100
gtcgtattca agatcaatgc cagcttcata ggctacatcg aattcgttaa acttaattgc  20160
tcatctggta aaattaattt agattttcat ttttgcttaa agagtactgg tgacattttt  20220
tatccgattt attcatatat ttttttcact atacgtttgc tatagcacaa caccagtttc  20280
tcatggtgtt ccctctcgtc ttcatgctaa ccgtactcgg tgccttcatc tgcacagccg  20340
tcagaacttt tatggacgct gtaattttct cgttaccgtt gcaggttagc cattattttc  20400
ttgttccacc ccaaactttt gaaacctgac aatggtagta tgataatcct attgctacat  20460
tgaattcgtg ttattctatt gcatttaact tttttttct gctgacttca tctgctgctt  20520
gtacagcttc attggttggc gatgagtagt gagatcgctt tcaattttag aagctctaat  20580
gttcagttct gttgtggttg tatgattagc caagcagttt catgtcattt gaacagttgt  20640
tgcttccact tcgattgttc tgccgtaaag agacttagtt tgccaactaa aattgtgcgc  20700
aactcgacta attaatcatg catgtttgtg ccgttatata taggcttata gcctacagct  20760
taatgattcg attcctagat caataccaac tgcagttaca gtgcattcat cttgttatag  20820
ttacttagtt agctatatgg tcgttggtca ctgctatgtc aagttcatat ggcttaatta  20880
attgtttcat ttctagctcc atgcccttta ccatcattgt gcattttgtt gatctcggtt  20940
taccaccagt ttatgtgata taaaccaacc cttgcttaac tgatgtgctt atcttgttgt  21000
tcatttgttc cagtgctggc gtccgtgacg aacacggggc gatgtcaacc ggcttcccta  21060
gtgtttaatc cttcttccga tcaggtttcg gtagtacaat acttgcttca tgatggcagc  21120
cgcatcattt gtgatacctt ggctgttctg atatgctatg tattttgcaa caacccaaat  21180
ggattgttat atgcagaaat tactcttaga aactaacccc caattggagt actagttggc  21240
atggtttcta ttgatgatac tcctagagtc gtagtagtaa tctgaaatat atgtgactgc  21300
tgcagctctt acctgttctg ctgcttgttt tttgaaggaa ggcaaaagct ttgccttgaa  21360
tatattaata gagcaggaaa aaatatagcg agatatatac agggttagat gaaaaaaaac  21420
```

-continued

```
gaaacaaata acccgcaaga ggagaggcaa aaagcaggga ttaagtgata tcttccaaaa  21480
ttccgaactc ttgcaggatt gaagcccctg ctttgaccca tgctctccct tcctccttga  21540
tctttgctag aattgaggat ggcgtagatg cattgttgcg gaagattctt gcgtttcttt  21600
cgcaccagat ttcccacgag attaaaatca ccagggtcct gagaggcttg catggggtgt  21660
ttggagattc cgttacgagt gtccaccatt gctcgactga gtgacagctt tccgagttgt  21720
ccatctgaag gtcagtccca gtccatctct gcatttctgc ccatatcctc tttgtgagtt  21780
tgcatttggc caggagaagc agggccgatt catcaacatt ataacaaagt gggcaaatct  21840
tttggttttg ccatcctctt ttttccagcc tgtctgccgt ccatactcta ttttgcgtga  21900
ccagccaaga gaagaacttg cacttcggcg gcgcccatgc cttccagatt gactgataga  21960
aggtagattt ggcagcccca aggaattgta gtcgataggc cgattttgcc gagtactgcc  22020
catttgctgt gaggttccat cggatgctgt cgtggttttc tcttagaggc ctcatatctc  22080
tgatcattct ccagaggcgg atatactgtt ggaggtgatt cgcctcgaag atgcgagaga  22140
catcaatatc tcgtatccac ttgttttctg ctaaggcatc atgcacagtt ctattctttc  22200
ttctagaggc cacgaaaata tctggggcaa tcaattgcgg tgtttgattg tctagccatt  22260
ttgagcccca aaagcgtgca attttgccat ctcccaccgt tattgttgtt gtggccgcga  22320
agaggtattt gtctagctga ttgcatggta gcacagatcc cacccaaggc ttatccggcg  22380
ccacccattc gttccaaagc catctgagcc tagcttagag ctgatgtgaa atattgcagg  22440
ttcataacac ctaggccacc caaaactttt ggcctgcaga ccctttttcca gttgacttta  22500
cattttccct ccgagatgtt ttcgcccccc gcccaaagga atttcttct tattttgtcc  22560
aactcctcta gggttccgtc tggtagcttt agtgatgtta ggtggtagat gggctacgcc  22620
gtgaggactg atttcgttag gcagattcta gcgacggtcg acatcatttt gccttgccaa  22680
ggagcgagac gcgcttggca cttgtccatt aagggctgaa tgtggacctt cttgagcctt  22740
ccaaccacga ggggtaggcc aaggtatttc attgggaagt ttgttaggcc tgctgggaag  22800
atcccaatga tgctggagag atcaatgcta tcacaccgga taggggcaat ttggcttttg  22860
ttgaggtttg ttcggaggcc cgtcacttgc ccaaaatcgc ttagaaagct agtgagattt  22920
gtcatgtctt ggacacttgg gttcacgaat atggccgcat catctgcata gagggaggtt  22980
cggaatctgg gagctcttcc gcgaagaggg gacatgtgtc ctaattttgt tgctttctct  23040
agaaggtggt ggagtgggtc gatggctaaa ataaatagca gcggcgagag ggggtcaccc  23100
tgccggaggc ctcttccatg ctttataggc gatcctgggc atccattgag gaggaccctt  23160
gttgtcgacg aggctaggat gtttgagacc cagttagtcc accgagatgt gaagcctttt  23220
ctctggagga ggtcgattaa gtaatcccat ctaaccgaat caaaagcttt ggttatgtca  23280
agcttcaaca gaagagtcgg cgttcttgtt tggtggaatt ttcttgtcag attcctcaca  23340
tacataaagt tgtcatgtat gcatcttttc tttatgaaag cactctgggc gtgactaatc  23400
aggatcccca tgtgaggctg caggcgcagt gcaagtacct ttgaaattag cttcccaact  23460
ccgtgtatga gactgatagg cctgtagtct cctacgcatt ctgctccctc cttttttggg  23520
atgagcacca cgtttgctga attgaggatc gggaagttat tacttcgtag ccggtcgaag  23580
gaatgaatga ctgccatgat gacatctttt atcgtttccc aacaggcttt atagaaagca  23640
cttgtgaagc cgtccggacc gggcgctttg tcgctgggag actgtttaag tgtcgcgtga  23700
acctcctctt ccgtgatggg gccgctaatt acggagcatt cgaaagttgg taactgcagg  23760
```

-continued

```
gcgtcctagt cgagatcttt tgagcgtgga gctaggtgtg ccatgaaggt ctgaaagtgt  23820
tataaagtgc tcttttataa cagtagcttt ttcatcgtgt tttactttcc acatgtttcc  23880
cactcgtagc ctctgaatga agttttttct ctttcttgca ttcatcctca aatgaaagaa  23940
cttcgtattt gcatcccccct ctttgagatt ggtgattcat gcagcttgtc ttctacgggc  24000
tctttccacc actgcaagac ccagcactct gtctttgagg ttccttctta gcgtgagttc  24060
ggcttgagtg agttgccttg actcttgggc tatatcaaat tgaagaataa tctcgagcgc  24120
catgtgtaaa tgaagcttcc cctgcgaaat caatttttg ctccacgatc ttagtctttt  24180
ggccatacat cccagtttgt gaaagagtct atggtgaggt tcatgatggg gttggggtgc  24240
tatccaggct tcttgtacca cctcgtggaa gcctgggagg tggatccaaa agttctcgaa  24300
ccgaaaagtt ctcgatcgtg gggcctcccc ttgtccggtt agcattagcg gacagtggtc  24360
tgagagtgag gtggataggg catgtaaaag atgtctctcg aatgctgtgt tccagctagc  24420
gttgcaaaaa aaccggtcca gtttgacgag ggttgggttg tcttgttcat tactccaggt  24480
gtatcgccta ttctgaagtg caacctcctt gagctcgcaa gcgttgaggg tttctttgaa  24540
aattcgcatt tgtctgcgat taatgtttgc attgtttttg tcggaagcct tgtagattat  24600
gttgaagtct ccgagcacca gccattttga attgtcagat ggcttggtgt cccgtagttc  24660
tctcaggaat gtttgcttgg cactctgttg acagaaaaca cgaggcctgg gagatctgct  24720
taactccagt gcaggtccaa agctcgcctt caaatgtatg agcgtgccag ttgatttgat  24780
catgtaatca acaagaaata gagacaaaga attcgtggtt aaatctataa atgatagccg  24840
atcggctagg tgtcgatgac atatcattta tctttgagct gatgtcatat atgaatcgat  24900
cggcggttat aaatagatag taaggaacta gatctattcg atcgactgta gatattaacg  24960
atatatagtt cttatattaa taaatactta aatcaagtga ttgggataga tcggtcacca  25020
tgccgagaca gcataaatca cttagatcga aatatatatt aataacagga ttatatatat  25080
ttatagcata gccgatcaga tagatctagc atgtatcggc taatactccg atactacttt  25140
atataaagat atcaaaacaa atataatata ccaaacaaaa gcttaatata cttaaatgca  25200
ataagatcct gacataaagg gcggatttaa catgtcattg aagcatatag atcgaatatg  25260
gttaaatcag ataagatcgg ctgaaactcc gatactaccc taatcggtaa ccagaggaca  25320
ggctagagat tgatattcta agcacgactt aatagatcaa actcaactga tgcagcatta  25380
agtatgaaaa gaagaacaat atctagacaa tcaagccgct gggtgtttca taaagtggta  25440
gatatcttat ataatttagg acaacgtcgc tatttaacct aatcggttgc cttctattaa  25500
cagatgttag ccgattgtag gttagatgat gatattgcca aagattatgt aagatatatg  25560
ataacttgac gaattatata gacaagatta tagtgtcata aagatggaag cactaatctc  25620
gagaacataa gtcgtcataa caagttttac ctcttgttga agatcgaaac cgatgcagct  25680
caacccgaaa gcaagaactc gtcgaagcaa aactaaagtg aaaaggtggc gatgcgccga  25740
aattgtattg aacgtgtgtg ttaaaaatta catagggctc ggggtctatt tataaccgag  25800
aattacaaga tatgtccata ccggacacga ccactatctc taacaaactc taagatacca  25860
taagtctttg tggcagactt ttgcccaaac atatctctaa ggaagttaca taaaacatcc  25920
taattaatag aaacatccat gtgcggcaat catcttgaag cacctcaatt caacccaatg  25980
tcatacacca aattatactg tcagaatcgg ctgcatcggc tcacctagtc cgactcaaac  26040
ccagccgatc ctaatcgtag ccgatctgga cttcagccaa ttcttgctct gttctcggat  26100
taatctccgc cttcgactcc accttgatct aatctccttt tccaatgctg atattaccaa  26160
```

-continued

```
atttggtcgt taacacactc tctctggtta gcccataaac agctgtaagt aggaaggtgg  26220
tctgacattc ttttaaggag actgtggccg aaagtgagaa tgttccttgc acaaagtctt  26280
tgagctcggc aaaatcctca ttccagagga tcaggatgcc acctcttgtt cctagcggtc  26340
ctgtcgctgg cttgaagtga aaagatttta ggcgtccccc gccaagggaa tgtaccagtc  26400
tggcatcaat gttgctcatt tttgtttctt gaaggcaagc gatatggggt ttggcttctt  26460
gaagagtctc tctcactgtc gctcttctgg ccggtctctt gaagcgatat ggacgttcca  26520
ggagaggatg tcgatgatcg ggtatgtcat gtgtaacctg tattcctcgg ggaagggggg  26580
gggtgggagt tgtgcacgaa gccgaggggt gacagccgtg tcggtgctat caggctgaaa  26640
ggtagtcggc ccaatctagt ggggcgatct ggctcatgga ccgagtccga gtccatttgc  26700
gcgaagttca gtcgggggga gatgagccca ggcaggaaga catgttgggg gcccacatgc  26760
aattgggccg gtttgagaag acgttgggct agaaagactt gggccgggga tgtatgatgc  26820
tgtagggcga aactgatggg gatgacagcc gcgcgcgcca ccgcggcgct gtgcgtcgcc  26880
ccacgttgtg cccgcgacag caccgttttt gtgtcacacc tggcatcgag ggcggtagga  26940
ggggacgtgg gggcgaaaca gcaacccagt cgtcgacaat cgtagagagt gctatcgttg  27000
gggcccttag aattgcgtcg tttgtgctgg ccgtcagtga ggcatgacgg ccgtgggggt  27060
ttgctggcgt cgtcgccgca attggctaac attatcgatg ttgtttgggt gcggagttgc  27120
ggcaccgaga agggataggt tgattcgcga agttgctgcg aatagcggga gtagcaatgt  27180
ctggcggtgt cgccgctcat aacggtagca cgcgtccgag tctcacgcag atacgaagga  27240
agcaaatgaa atcgatacat ggagacagag gactccgttt gccagtgcgc gaagcacagc  27300
ttgctcacgc cgcagcaatc tcctcctggc agccaatgtc agagaggccc aggtaattcg  27360
ccagagccgg gtccaccgtc ttcgcgtctt ccttgtcaaa gccgaacagc tgcgtgaggg  27420
cgtcgattgc gtcttgcggc agcggcgagt tgaacattgc tttgaagtcg gcgagtgcct  27480
tgtcggtgag gactccttcc gctggaaccg tacccaggcg ccggcagaga ttgagctgcg  27540
cccgcaacga catcagtagg ccggccaccg gctgtcgggc tagccttgga ctcctccgcc  27600
gcccttcacc caacatgtca gcagccactg gaattggaac gacctccagt gcatcatcgg  27660
gggggatcag cacctgcgtg tctccggcga tgtcgatcag cacctgcggc gtggagagga  27720
ttgccgaggg aagttctttg aagaggacac gcggcggggt tacctgaacg gagtcgaaat  27780
cggcgatgtc aggcgtcggc gctgtctcgg tgtccttgac cggggacaag tcgttcgctg  27840
caagcgtgtc ttgaagagtt ggtgccgcgg cgcactcagc gttcagggac ggcagcgtct  27900
tttctgcgga cgtgatcggc agtagctccc ttgtagttga actgatcatc gccagcgatg  27960
ccaaggctat caccggcggc gatggtgccg cagcgttcgc ggcaggtttg tcgagcgcca  28020
ctggcgcagc gagcttgtcg agcgccaccg caacaccggc cgcaactagc atctgtcgca  28080
gtgcccettc caccgaggct gccgcaacgg cctagttgat gcaggcgaaa acccgcgccg  28140
ccgggatgga cgcagcggac cgggcttcat accccgctcc atcgtgtgga cgacgtgacg  28200
ggagcagagg ccccttgtcg aacgggggcg atgtcaggtg agcattccgt gccaaggacg  28260
atgccgcaac ggtcggagtg agagagtcgc cgtttccgcg atcattgtca ccgtcttcct  28320
tatcaccgca gccagccaga tgaagccgtc cgtcgcgccg ccccatgtcg ccacggtcat  28380
gggcgcgcgg tgagcgcgtg cgttcgcgcc ggaagttaat gtccaggccg cggatgccac  28440
ctcgcccacg tgcgacgtcg cgtcccctgt tgtcgcgatc gtcgtcgtag tcgtcgtcgc  28500
```

-continued

```
gtcgcccgcc acggcggaga tcattgtccg ggtgatcgtt gttgtatctc ctgttacggc  28560
ctctgcgcct gtcttggccg ccacgatcat cgcggccgtc gcggcgcctg tcgcggcgtt  28620
cctcgccatg gcgtcgttca ccatcacgat caatggcatc ccggactgtt ctgcttcctt  28680
ggtcgcgggc ctcccgttgg agagtaacgt cattgtcctc cacgccttcc gcgtggccgt  28740
ggcggaaggt gtaggtccgc ggcggcggcg gatggtgagg gaaatcttca aagaggcgcg  28800
gcagaggcgc tcaccgtcca gaacgcccaa gtgccatggc ggcagagtgc gtgtcgccgg  28860
cctgcaggac ttcgtattgc ggaggtcgac ggccgccgcg gtgtaatcgt ggatctcctt  28920
gatatggaag aggactagat gcttgacccc cttttgccag tgctccggcg gcgtctccga  28980
aatcgtgatc gatgtgctga gatgcaccat tgcacaatat atggtgcaag ttaaacagta  29040
atgtgggatg caattagctt cttattatgc atgcatgtgt ttaccaaagc tgaaatttgc  29100
atgttctctc agttgtccac acttcttgcg aagggaggaa gtatctatta agattcggca  29160
agatacattt gataatgaag tggcaatagg tacatggttt caacccaagg tcccatggtt  29220
aattctcaac acactcactg tttcttctta attattcgac aagcaagtta gatccgacag  29280
aaaaaattaa aacatatcca gacaaaaaaa acttcggtct ttgacaactc cctccgtttc  29340
atactcctgt ttatggtttc gcttgctatg tatttttata aacttgagga acttaaataa  29400
gtttgactaa gaaaaaaaat aaagtatgaa ataagagtat tatgttacat aaaaatatat  29460
tcgatctaac tatgaaacta ataggagaga cataacatac ttaaaatgca tatttgatcc  29520
gacgcgctgg cgaccggggg gcgaaaaccc tagcgccgcc cgcctttccc ctccccctcc  29580
cccacctcgc cgccgccgga gctcaccgcc ggaaagtcgg cgggcgagct atgatggcgg  29640
cggcggggct attctctgtg gcggcgccct ctctcaggcg cgggagaggc agcgaacggt  29700
ggcgtctggg gagtggcggc ggcgagccat ctcggcgagg aggcggcgga tccggcgctg  29760
ccttcgccgg atctggccat cccctagctg gatccagcca gagcgcgggc gggccggcga  29820
cgaggtggca tcggtgcgga gcggcgaggt gtgaggatgg cgcggcggcg cgacaagggt  29880
gacggcgacg gcagaggacg gtgcgacgag gcgtgctgcc ttcgctggat ctggccatcc  29940
ctagctggat ctggccggtg acggctcctt gtggtgcgga ggcgtcacgg cgtgagaagg  30000
cggcggtgct ggcggtggag gccgccgcgg cgcggcaagg tgcgcgacgc cggcgcagtg  30060
aggtggccga ggtccgggaa ctgccaatgg cggtggggag cccctggtgc ccgacagcga  30120
tggacaggag gcgcgctgcc tggcagcggg gtgcatcggt ggatggctca gccttggccg  30180
gtgactaagg ttgacccggc cgatgggctc agtggcggcg aggctattgc aggtggagga  30240
tggatgcgac gatgatgcga ctagcggctt gttgacacgg gtagccggtc gaggcggcga  30300
cgatggtcac gtcatgaagg ggtgttgaag cctacggcga tcttccctcc aggtgtttgc  30360
ccttttgcgg tggcggcttg ccgccacaag atggccacgc tggacgggcc agtgcggggg  30420
cgcagggggg aggggatcca ttcttctctc tccccctctc cacctccaac ccaaccacgt  30480
ggatggagtt gaagcgcgcc gaaggacgaa actccacttt gatggtcggc cggcagcgag  30540
gcggcgcagt ggttgcgcgt cgaaggggat tagctggtgg taccgttgaa cctgacatgt  30600
acgctttagt gcaggagagt aggaattagg gcgaaagcct agattccggg ccagcaatgg  30660
tgacatctgt gggtgccgct ttccccttgg ggccttgcta cgtttccttc cctttcccaa  30720
tgggttcttt aggtgaaaac cacttcctgg agatccagga cgggcgacgg cgacgcactt  30780
ggcgtcgttc cttccttgga ggcgtcgttc ataagaccca ttccttacgg gtgttttgtg  30840
cttgttttgt tctaacagta ggatcagacg tagacgcgtg gtgtggctgt attttatttt  30900
```

-continued

```
ttttggctat agtcttccag ggctatagac ttgtattttt ttttctgctc tatcaataga  30960
aacgtcgcac tgtcgggttg tttaaaaaaa atgcatattt gatcagacca tatgatctga  31020
tacgtaaaac aaactaatga ttataggttt ttatttcgac gatacagtac ctgaaaaaac  31080
aaaacaagaa gatggcttgc cacaggagca aacacagact gaaactcatc aagctagcta  31140
aatcccgaat cagaaaatta ggcctgtggc gccacgccag catcagaaag ccagcggaca  31200
ccgtcatcgc cgggaacgac accagcagcg ccaatgtcat gcgcgcccgc cggcgacgcg  31260
ccgccgccgc cgccgcgatc gtgtctcgcc tgatccgccg tcggcagcag cttcgtcatg  31320
cgtgttgcgt cgatgcctga aacagattac gaataataaa ttatcgaatt atgaagtgta  31380
tcgaagtaat taaccggcga atcacaaatt aatttcgcgt gtacatgctc tgctctggtc  31440
cgaagtttcg cttgccatgc tgcccaagcc gctctgcaag atcgaagtat tgatcacgtt  31500
attagatgat gaaatctgtt cattggtcat attagacgag tacatatata tgcatgtatg  31560
cgcaattgta tacggtattc tcaaaaaaaa aaaaacgtct acgatctggc gcatccaaga  31620
aatatactcc ttgcctttaa cagatgtgta ccgataaggc gataagtgca tcttgctctc  31680
ctcaagcagt caagctaaat acctgccaaa ctctttttct ttttgccaaa ctcttaatta  31740
cagtccaaag tactcaagag ttaaggctgc attacgaatt gattctcgga ttggctactc  31800
cctcacctat cggaagcaca taatccgaac tgctaaagga tataattttt aaatagtttt  31860
tatataaaag ttacttaaaa attaaataaa tctattttta agtttgtact aattaagttt  31920
cgggtgtcac tgaaaatatg gttttcgaat acgctccctt tggtctaagt ggttttgaag  31980
tttattctct cggaggatca tatgtggtct ttagctgggg ttgccgcttt tggggatttc  32040
tagagagtgt aacgtggctc tgtcccttct cacttcccac tgttagaagt tgcgtttagc  32100
cgccgtagta gttttttttcc ctaagcttca gtttctgttt tgctttttct ctattccctt  32160
ggaataagcc ggtctggagg attgtattgt gtaacaaaaa ctcttttcct tttcttttaa  32220
tatattggcg tgcaatcctt ttgtgcattt aaaaaaaaaa gatccgacaa gcagatttaa  32280
acgaagcctt attatatggt aattcaccaa acaccgagta aagtgtgcag actagaaatg  32340
aaatttaaat atcaaaacat tatttttaaa gattttgttt tttgggggga gggggtgtgt  32400
gggtttcatc ctagcctatt tttcaacatt gctttttttaa atatgatata acacagatat  32460
aaaattttac tcgtaatttt tctttagtta cttcgttgct tttttcatgg cttatcaacc  32520
atagctcaaa tgatgggaga gaaagcatac tccatttcca aaccattata acaaaactta  32580
gtaatgagag gaaaaatatt gaatgaagga agtgtcccat taattaaaaa aaaagtattg  32640
acaggtggca ctccataggg agtacccccca tagaagtatt gaatgaagga gaagttacac  32700
tacaagcatt gcaggataaa atttgttgat ttttgaaccg agggtggtat tcataattaa  32760
taaggtatat agtcaaggaa actttttcct tgatttgcta aggtaggcta ggcccaacta  32820
gctcacttgg gcccagttaa ccaggcaggt tgttattgtc cacaagtcca ccaaactgat  32880
cgtgtatcct ctcagattgc tgctgctgcc tccagcaatc aacaactcca gatcaaatcc  32940
ttcagaaatt acaggcagga gagaagtgtt ctgtatcaaa ttctggctca acttcttcac  33000
attctaaaaa tctcaaaaaa aaaaaaaaca gagagcatcc cactcaagca gagagagacg  33060
tgcttgccaa acgaatgtca cttcccactt ctcctgctag ttcgcaggta gcacgtccta  33120
cctcagggct atccacccat aaaaatcacc tttcatccaa cggttgcacg atcacaaatc  33180
cgcaatagac cttgagaatt aaggcaagtc aacaacccta ccagaggttc ttggaaagtg  33240
```

-continued

```
catgataccg tctcttgaag cttttacaca gaaaattttg gtactactga aaccgtcctt  33300
tttttgaaaa aagtataatt gaaggctgaa aggttcatga agtatgaact gacggtttca  33360
tagttattac ctctgatttt ggtctgaaac tgtagcttgt ctcggaactg tattagtcaa  33420
aactcaccaa agacaaacct gagctagtat gaaagaagtt cagacttcta gaagcagcat  33480
gttgctgctt tgagaaagac agatatctgt ctaattcagt ttagtaccat tcgctcggtt  33540
ggtcagaaac gttagtagca gtcagtggaa aaaacattgg tgttatggtt tttccactga  33600
ccagattagt tggagcgtgt tgttctgaac tttctgcaaa tggacacgaa attgcctgca  33660
attggtaggc acggcaagga aatttctctg cacaaggtct ctgtagggtt agttctgaag  33720
aaacaacgga cttgaatagc tgatatcttg gaagaattgg gtaccatatc aaattatcaa  33780
tcacaacttc tatattgcaa atagtaggac aggaaagaag actgaacaag gagttcatca  33840
acacggctcg tcctgcaaat gcattttcag gaggccgaac tacgaagaga ctgtttcata  33900
tttacaatgt acgtatgatt cacttgttac agcatgccat gcgttggagt gtacatcaca  33960
aagcagaact aagaccaaaa attttcctag aagaaaatca ctaaaaaaaa atctgtgtat  34020
ctgtatacgt gtatcttctc acaatgtcag actcagacac tacactgctt tgtttgatgg  34080
ccccctttta acctgacctg cataatggat taagcaaagt attattttca gtaaataaat  34140
tgatcgacta atccatcttt atgatgctga ttaggataag caaacttttt aaggctgtga  34200
attattcctt tttgcctaaa atattcggtg cattgcagct tagtaattga ttcctcatcg  34260
ttctcaccga aagcagaagg caacatgtcg atgtgatata cccagagaga aatgcctgga  34320
ttattctcga gaatcgcgct ttcggcttgc acgaatctca aggcactcag attatacatg  34380
atcatggctg attggctgtc actatgccca atttgattgt tgcaatttca gttttttttt  34440
tttcaaatta ggcgtgtatc gtgatcgaaa agatttcact tttgaagcga agagagaggg  34500
gaagggtgct caccgcctcg acgtcgatcc ggtagacgag caggcggcgg cgctcgcggc  34560
agctggtgcg gtacgcgacg gcgaggtgcg cggcggcgag cgcaaccgac agcaggagca  34620
tgggctccgg gcccttcccc tccggtgccg gcgcgacgcc gcggcgcggg agcacggcgg  34680
cggcggcctt ggccagcacg taggacaccg accccgccgc gctcgtcgcc accacccaca  34740
ggtacgccgc gcctccgccg ccgcacgcca tgtacgcgcc tgcgaaagag aagaaaccgt  34800
cgaggtcaga gagacagaga acgaacacga ggtcgatcga acagaggtgg cgggcgtcga  34860
ttgctcaccg agtatgagca gcgcgcgcgc ggcggagacg gcgaggaggt cgacgagcga  34920
cgagcggaag tcgaacgccc gcgcctgcgc gacgacggcc gccacgaacg acgcgtcgtc  34980
cccgcccccg ccgccgcgga ggcgcgcgga gaggagcgcg ggcgggaggg cgaggtcgag  35040
tatcacgacg agcaccggcg gcgcgcagac gagcagcagc gacgcgatca tggcgacgac  35100
gaagaacgcc gtcttggccc acctccacgg ccgcgcccac accctctccc ctcctccccc  35160
atgcttctgc gccatcgcca gcgccaccgg cagcagcagc agcctcttct ccgccatatc  35220
cctcccgccg ccagctgtgg tggtggtcgc cgtcgccgga gcgagctagc tatagagtcg  35280
tgggctatgg attgcttcgc cgcgtcgagg ccgacggttg agggggacgt ggcgcgacgc  35340
gaggttgacc ttgccctgcg cccgcagctg caactccctt taatactact ccgatcgtgc  35400
cgaagcttcg gcgactcgtt taattacggc ggtaactgct aggggaaaaa cgactcgttt  35460
agtttatttt tttaggtaaa aaaggttgta atagtgtgtt ttaagtttta accgtgtggg  35520
cttgcgcatg gggaacgtgg tcgaaaattc cgacgtagtt ggacccgagc cggactcgag  35580
ggagaccggc aggtgagaaa ggtgaaagaa aaggggaaag gtgagatctg cttcgttcgt  35640
```

-continued

```
gtaggtgaag aaattcgaaa ttcttcaggt ttttcacctg ccagaattac caaatcccaa  35700
ctgtacaaga gtacaggagt agcagcagta aactttctaa aaaaaaaaag agtagcagca  35760
gcagcgggag tggattttaa tcgatgtcca ctcgttgttt acatgccact caaatagttt  35820
tgaaaaaaat taaaaaagtt ttgggaagat gtattaacat gtgatatatc acttcacaaa  35880
catgcaaatt caaattcaac tttcaaatat cgtaaaaaaa caaatttaac tctagatata  35940
tgttaactag ctgtaattta atttgttttt tcgttgtgag atacataagt tgaatttgaa  36000
tttgcatatt tgtgaagcga tatatcatat gttaatacat cttcttaatt taattttttt  36060
tataaccatt tatgtaacgt atagataacg agggtatatc ccctcgaggg atataaatag  36120
tttccccaac agcagctact agaggagagt agagtccaaa cttgggtggc cggtggtaac  36180
acatggcagg catgtgtatc tgcatctgca tggccaagat ggaccacatg aatgacggcg  36240
tggtacgtcg gcgagacacg cgggaaggtg ggcgccaatc acatggcggc gccggcgccg  36300
gcgcggccgg ggtaggaacg ggtggctcgg cgccggccag gtccggtcac cgtcttccgt  36360
ggctgatgtg tcatgtgtgt gggcttctgg atatcggagc gagcagccgt catcggccat  36420
gtgtacggca accgctaacc gccaatgata attaagtatc aaaattattt aaggtgtgtt  36480
ctattcccac tatccacaaa tataagatgt ttgtaacaca tcctagtaca acgaatctag  36540
acagcgaatc cgtccaaatt tgttgtacta tgatatatca ctttcaacga aaaaaccata  36600
tatctgtgga cggagagagt atattgcacg ttactaactt ctactctctc ttttttttaa  36660
cttgcacatt tcctgaacgg ctgaattgtg tgttttctat aaaacaattc tacagaaaag  36720
tttgcttgaa aaaatcatat taacacatct ttcaattttt ttactaatac ttaattaatc  36780
atttgttgat gcaccgcttc attttagatg tatgagggaa gggtttacta gagtatctcc  36840
ttcaggttct caaatataag atctattttg cttcattagg acaacacttt acaccagaat  36900
tgttcttcta taatattaaa gcataattgc aaatactttt aaatataagt ataataaaat  36960
taattttgtg tcaagaatta ttttttccta agagtaaatg ttagttaaac cttccatact  37020
aatattttag agcagaggga gtgtataatt tgattgatca agtagttgta gtgttcaata  37080
tatttcgttc ttaaaagtag ttgtagactt gtagtgttca agtaggctgt tggtggggac  37140
cacctccaaa gctgacgaat tgatggaaga aaagaaaaat gaaatactaa tatgcatgtt  37200
gtctttgttc cgcatctgat tgaggttttt aattgatgaa ctcttctagt agatgacgat  37260
ttgcagttag cagttgcact tggatttgga ttcggatatg tgcattgtca aaatatataa  37320
ctaaatgctg ctagtagtgt tcttaggcca gcagttttgg ttggcttcac aaggaagatg  37380
agcatattga tagagctgtc gcatggacaa tacagacgac gttttcatgc gcataaatta  37440
tcattgtcca tcttgttaag tacacagacc actgtggatt gtatatggtc agtacatgta  37500
ctttcacgcc atatggccat ctcggatatg cttcaattcg atgttaatta cacaagcaaa  37560
tctagattag ccaacaaagt gtggcttaat taacttgcct gtacacaccc tgctcagttt  37620
ttgtaatgtg aaccaggacc ccatcagtga ggaatattat tccttcaatt atccctatac  37680
tacagtctac agctataata actagctatc actattaccc gactttgttg tacttacgtg  37740
ttcgcattca gacgcatttt ttttctttta atcagccagc ataataatat atcaatttta  37800
ttaattagag ccgaaaaacg ttttaaaaaa gacacaaata ttagggaatg acctaatatc  37860
aaataattag aaggggtgag acttcgattc caagccgtct agcccactac cttgtggagc  37920
tagccggaaa actcctgggc atttctcgcc caaaaacgtt tataacccca atggtgaaaa  37980
```

-continued

```
aggagctata tattccattc agacgctact gaaaatgaag tgtgcagttg tgatggacaa  38040
gattattttt gcaaacgaca gcatgtttcg acacatctga ggcgttcaat ttcttgtctg  38100
gtgccggtca gcagttgcag gttaggttga gattttcagg aagcagacaa ggcgctggcc  38160
cacgttgtgt tcatctatga gctcacaagt tagccgccat ttggaacgag ggtgcatgca  38220
tttttttaa ttttattttt gttagttttg aaagaacagg tgcacgaata atataattca  38280
ttggccgatc ctaatcatgt gacaacttgg ggaaaaacaa ataattgcac tcaattgaaa  38340
cttggtgtgt aagactttct agtactagtt catttttttc ctttgaggtt aagcattata  38400
tcccattcat atctttctta ttttttctg caagctgctc tatgatcgat catatggact  38460
gggtacatgt ttgcatctag cccaactggg ttggagttat atactacctt catatcaaaa  38520
tatagcaatt tttagttatg aagtgtccag attcatagct aaaaattgct atattttggg  38580
atggaggtag tactttgcat tttcgtccat cgattttaga gtacacatac atacgcattt  38640
agtacgtgta tgcgttttag gatgagccga tgaggccttt gcatagtaga tctctgtcaa  38700
ttttcaaaca ttgtgttgat ttgtaaatga tgaatcgtgt tctcgtagtt ggaagtattt  38760
agcatgtttg gttacattag ttctgttgat tttatgaatt atggatgaat atacatgtta  38820
atttttcatg acaatgcttt aaaactcctt ttcaactcca caatatttaa ttcattttcc  38880
caactcacct ccctcgtttt ccgcgcgcac acttttcaaa ctactaaacg gtgcgttttt  38940
tgcaaaaata ttctatgtaa aagttgcttt aaaaaatcat attaatccat ttttcaaatt  39000
tattttagct aatacttgat taattatgag ataaacgctg ctttgttttg cgtgggagtg  39060
tcctcactcc cgaacacacc ctaaaccagg cctaggttgg atttcaacgg ggaaaagggc  39120
gagcaaaaac agatggtgat cgaggctact actcaaacta ttccacgacg cgcattgcac  39180
ggacgtactc ttcccagcaa agacttggtg atggtgatcg atgccgccat tcctctgccg  39240
tacttcgatc gcttgcttaa cgcgaattaa gctaccaata atcgaagctt ccacccaacc  39300
tttttttttc caacgacgac cttgatcttg gaacttttgg ctgatgacca gtccgtcaaa  39360
catcccggcc agcttaatta gctgccgatg ttgacgggca ccgtggcgag agagacttaa  39420
gcagcaacgg ccattgtttg tacgcgcttg cgttcgatcg gcagtgcaag agccaccaag  39480
atcgatagct ccatcgccgg cgagcgacgg agatggcggc gtcgcaggcg tacctcgaca  39540
aggcgcagct ccggcagagc taccgcaacg tctggcacac cgacctcacc aacgccatca  39600
cggccgactt cacatgtgag cattcgtcat ccctgtgcaa aatgatagtg ctagttttct  39660
gatgattttt gggagtcgat ctaattttct ctatcttttt tttccctgca ggctgctgct  39720
tgtctctgtg gtggtgagtt tgttcatcta ggtttctgaa tctcttcatg gctgcatcga  39780
tcttcagctt aggaatattg ctaagtctga catgtttctt atctgatcca tttctcctta  39840
tccagcggac catgtgtgtc ttacatgctg cgcaaacgtg cgctctacaa tgacatgtcg  39900
aggtaaattt gctcttttc caccatatgt ttgttcatgc gaaagggcat gtagcttagt  39960
ggttgcggta atctgaatag taccccaagg ttctaagttt aaatctctat atgagcgaat  40020
ttcaaattgg gtttgagggg ctaagttttc aatttgaaag gctacatata ttcgattgga  40080
catagagacc gggtaaaaat tacccttctc tagaaaaaat aaatatgttt gttcatcgtg  40140
catagttaac tagcagtgca gttctctgtt cttaagtccc tttcacgcgc gtgtgtgtgt  40200
ttcagatatg tgtgctgtgc tgggtacatg ccatgcagcg ggagatgcgg cgagagcaac  40260
tgccccgaag tgtgccttgc aaccgaggta gccatctgcg tactgtagcc acccgagctg  40320
aatcagttcg atgatctaca tgatcttgac atgtaatgta ttcaagctga accgattcag  40380
```

-continued

```
ctgatgaaac tgtatttgtt tcaggtgttc tgctgctttg gtaactcggt ggcttcaacc  40440
aggttcctgc tgcaagatga gttcaacatt cagacaaccc agtgcgacaa ctgcatcatt  40500
gtactatcac tcccctcttg ttcatccgac tcttccaggg gcgtagccag ctaggtggca  40560
ccgtggtcca cggaccacct aaaaatttga aattatagta tatgtgctag ttaatatagt  40620
aaaaattgta tagtggatca cccttttaat tgatatatta catatagatg gaccactttt  40680
actttaaatc ctagctaaga cactggactc ttctcgaccc gatttgtttc agactgcgat  40740
taaacacagc tgtcttgtta ctttagggct tcatgttttg tctccaacaa ttcgcctgca  40800
tctgttcgct ggtcgcttgc atcgttggca gcgaagaact ttccgaggcc tcgcagttga  40860
tttcctgcat atctaacatg gtctactgga cgtaaggctc tcaactcaag tattcatcct  40920
tctgaaatct gatttctttc tttccaatta ccagtatttc tgatgttatc tgttgcaatg  40980
tgcagggttt gctcttgtat gcaggtaatg gcacattttt ttttttactt tcctcctgaa  41040
taatctcact gctttaaatt cctgatatct tatgatgaaa ctgcaaaatg taaattcaga  41100
cacagcacaa ggtcgagatg gacaagaggg acggcaagtt tggacctatg acagtgcctc  41160
caatgcagca gatgtctcgc atcgatcaac cggttccgcc ttatgttggg tatgcgccac  41220
aggcacagcc agcatactac aggtagcctg atggtggcta tccaagagtt caacatacag  41280
atcatgcatg ctcaagattt tctgtagcaa agtgaaggat ggtgatcaag tagatacata  41340
gtgtttgtga gaatgtgaag tgtctctagt ttctttaggt gatttagatg tttcagattg  41400
gtattgaact tgcgattttt atgtgggaat ggtgtgggtt cttacctctc tgttcctgaa  41460
acattcttgt gtgaataaaa ttgggggcat tggatggttt tgtattcctc caaaagaaaa  41520
tcgatggact ttattactat ctaccttact ttttcaagtc tgatatgttg caaaaaaataa  41580
agaaggcgtc catcttgacc tgtagtttgc agcaaatgct gaagtattgg gatgtaatgc  41640
aacctgtcat agtcacctca atgttgtggc cttacagaag tctcatgaga ggggttagtg  41700
gttgcagtga tctgagtagc accctaaagt tctgagttta aatcttcata gaattgaatt  41760
tcaaattggg ttatttgaag gctaagttct atattcgata ggctaagttc ctaatttaaa  41820
aaggctacat atatccggtt gtatatatag acaggtaaaa atacccttct aaaaaaacag  41880
aagtctcatg aagaaaacaa aataaaccca aacctttttct gagttcagat gatctagacc  41940
gtccatctat agatatcggt ccggtgaacg ggtgatgaac atgttgaact tcagttatat  42000
tttttaaaaa tatattttta tattactgaa acattttata tttctgcaat gaggtagtag  42060
agattaacac cagtggacca tttatcagca ctgaatattt taacaaaccc aaatctgttt  42120
acctttttcc aaaaacaata aaataagttt ggggggggacc ttatcggctg gcatgttcat  42180
tgtattgaaa tgctgaatta taccacattc tccacaatct gaattgaaca aggacactac  42240
tagtaacaaa ttgggatcac aagacaaaga cacattctta cacccaatct gccgtaccgg  42300
caaaatggat agaaaaacag agtacagctc ggttccttgc ccgcacgtat gtagcgtccg  42360
gtacatgatt gtgataagcc ctcgtactaa caatctccac gattcgcagt gtgtgcaggc  42420
acgtcgtccg gcgaagttgt gcgccgtgtt attctaatat tctccaacta atcatcactc  42480
tgattgattg attggtcaat ccgatgctca ctataaattc cagtggttgc atgctttttc  42540
ttcatcagag ctcggcaatt cagcctagtg tggtggtgca gaagaccacg agcaggacaa  42600
gatcggtgca atggcggcgg cttcatcgac gacggcgacg acggccatcc tggcggcagt  42660
gatcatctct ctcgccggcg ctgccaccac cgtggacgcc aagttcaggg cgatgcagtg  42720
```

-continued

```
gactcccgcc cacgccacgt tctacggcga cgagacggcg tcggagacga tgggtacgta  42780
cactcgtcgg attatttgcc ccacgcctta aaatacattt tttgtaaaaa aaaaatcttg  42840
ctttaagcta ctctcttcgt tataaattat aaatcgtttt gactttgatc aaattaaatt  42900
gcttcaaatt taaccaagtt tataaaaaaa ataacatatt caacactaga taaatctatc  42960
ataaaaatat attcaattat aaattcaatg taactaattt gatgttgcag atgttataaa  43020
tttacaatag tttaactttg accaaaatca aaacgatttg taatacagaa tgaatgtaat  43080
atttgttaaa ttttcatagg gatgagtcca tgcgtgttct agaaacaata atttatataa  43140
ataatcatgt aataagtaca ttagtgtaat aatctgtacc aaattgggtt gtggcaggtg  43200
gggcgtgcgg gtacggcaac ctgtacgcga gcgggtacgg gacggacacg gcggcgctga  43260
gcacgacgct gttcaaggac ggctacgggt gcgggacgtg ctaccagatg cggtgcgtgg  43320
ggacggcgtc ctgctacagg ggctcgccgg cgatcaccgt gacggcgacc aacctgtgcc  43380
cgcccaactg ggcggaggac cccgaccgcg gcggcggcgg ctggtgcaac ccgccgcggg  43440
cgcactttga cctctccaag ccggcgttca tgcggatggc cgactggcgc gccggcatcg  43500
tccccgtcat gtaccgccgc gtgccgtgcg cccgcgccgg cggcctgcgg ttcgcgctgc  43560
aggggaaccc gtactggctg ctggcctacg tcatgaacgt cgccggcgcc ggcgacgtcg  43620
gggacatgtg ggtgaaggcc ggcggcggcg ggggttgggt gcggatgagc cacaactggg  43680
gcgcgtcgta ccaggcgttc gcgcagctcg gcggccaggc gctcagcttc aaggtcacct  43740
cctacaccac cggccagacc atcctggccg ccggcgtcac gccggcgagc tggtgcttcg  43800
ggctcacgta ccaggcccgc gtgaacttct cctagatcgt ttttttagta gcagcaagca  43860
gcgaggagaa ctcactcttg ataagtgaga atgctcggct ctgctgctct cttctatcgt  43920
ctgctctgtc gctgtatcgt agttactccc gttgccccca tccacaacat caacatggtc  43980
atgtggaaca gcggggtttg acgacaacat tgatgatgta ctccaatatt gccatattgg  44040
aatgtaaact acattgtgat gatgcaagca aggcaaaaaa atttgccgag ttatttgttg  44100
tgataggcca cctaatcacc aattgtagca aagctaccat atacaacaaa aaaaaaagac  44160
atgtgctgca acttccagca tcctcggtat aaccaagaaa acttcaccac atttcatgca  44220
aaaacaacgc aattatggtt tggattagat acactaacgc tttataaatg gaattatgga  44280
aacacgaaga aaggactcac aagcaagttg aattgcaaaa cagtacaagg caattttctc  44340
ttcaagagag ttggtacgac cagggattta gttcatttgt tatccaaatt agcatccatc  44400
actcaagcgg tttcaacagt tgacaaagct atttctgttc ttcacacagc acaaatggta  44460
atgacagcac aaaaagtcca caatgatatt ggacagttct tcaaacattc cattttaggt  44520
tatatcccat aaaatccgat attttctggt gcaataatct gagattttgc aaactactat  44580
gcggatgtgc atgatgaatc gggtagtaac tttattaggc caatgtcctc aaagcaaagc  44640
agggtactgc ttggcctgaa cacgaacacg cctcttatat tctggtttgt cctgcaaagt  44700
agacaaaata atgtcaatga atgacatgta atgtaagaac aaggaatgcc agaatctcat  44760
tttttttca ttccgacctg tataaaaatg tgataaccgt cagtctgtgc aggatcagca  44820
ggatttggct gatcaagcaa gtcctgtatt ccaacaagga tctgctttac agtgatagca  44880
ggtctccagc cctgagaaga tgcaactgta aataaattcg gtagactgga aataaataag  44940
actgaagaaa cagcttgaag acttacacta tcctcattaa gaattgagag gcacactgtt  45000
cctgaaggat agacatttgg gtggaaaaag ccctgtggga acttgcactt gggtggtttg  45060
ctaggatagt cctcactgaa gtgaagggta agagggtagt acccaccttc ccaatcggtc  45120
```

-continued

```
tgtacaaatg tagcaataca cacaaataac ataagcaatt atgaactctg gatggaaaga  45180
aacaggaaaa gcttaaaagc aacccctaat tggcgttcca tgggcagagt gaaaaataca  45240
ctgtaatata catatatcaa cataaagaag caataagtat atgacaataa tacatttatt  45300
gaaggaaaat tagtatttgt tagcctacta ggctggtttg tcaagagagt gattgttaca  45360
taacaataga agttgagcag cagcatgctg aactaataca caagatcacc aggggcgcac  45420
ccaggcccgg gcaccttagg ccacaacctg gggcctggcc caactagcaa tggatccccc  45480
cattggttac agcttagaaa ttttggctca caaaggtttg gcccgaggcc cgtcaggcta  45540
gcatctattg cccaatacta tttattgtct aaccctaact tccccctgct accactacaa  45600
cgctatgcgc tcgtgggaga tgcgccgacg ccgatgcgtc cgtcccctcg cctccctccc  45660
tgctcgctcc ctccaaggcc agccgccacc atacgtgagt ctccccgctt ccagccaccc  45720
accaccctgc ccagccacct cacttccctc cctccgtcca tgtccactgc ctcctcagct  45780
cctctcgctg gctcggcggc ccggcaacaa ggctctttct gcacaacccc cctgcacggt  45840
gcgcctgcgg caagcggcag gtgctcagag tctcagacct ccactctgtc gggcaaggag  45900
cggacgagga ccttgacagg tgagtttttc ataatctatt tctggtattc ccatttctca  45960
aatgcctaaa tggcctagat cacctataga tcttctgatt ccattcaatt tgttttaaac  46020
ttaatagaga tagaaggtga agaggcttag cgatgaaatc tatagatgat tgatggggta  46080
taaagagaag aataaagatg accagaaaca tttcaaaatt ctcccgggaa tcatctaatg  46140
accagaaaca tttcaaaatt ctcccgggaa tcatctattc acttcactaa aaatacaaaa  46200
tctacagtgt aaatcttgtg caattgagac gggtaaaacc attctaaatg ctttcggtgg  46260
aaaaaaaatc cgccattttt gttgatgagt atgatggaga tgcatctttc aaagagcaaa  46320
tagctgtcat tttgaggtta gatgctgttt cttgcgttgt tgttttttttc ctttcgaaac  46380
tataataatt tgtattgtac ttcttattat gtattagtgt gggtctcatt tatggtatgg  46440
gatagtagca attagatttg gcctagggca tgaagaaatc ctgggtccgc cactgaagat  46500
tactatatat ccccccatat gcaagataaa gtgttttgga agtgatgttg attatgaaga  46560
cagtagtgat ggtgactata atccatcttt cagcaactaa atcttacaac attcagatcc  46620
ttgtaccctg ttaattcaat aactgtgccc gtgactccgt gcaattgcat cgggattcat  46680
gagtccgtgt gctccatgcc tggtttacag gtggtaaagc aaagcacgca ggcaactgtg  46740
caaacctcta gtgatggaaa agaactattt gatacgctga acctagaacg tttgaaggca  46800
actcatgcta caaaatcacg taattaacac tcaaacaaca gagaaaactc ctcccagctg  46860
tccagaaata aaaggtacta ctagatcaat tgatgataac actaaaattc taaaaaaaaa  46920
aatcatacta agatctgtaa gaccctagca aatccccact gcaaatcaac acgatccatc  46980
aataaaaact tcattcaaac cctccaacca acataactac tcataattct cccacaggtt  47040
atagagattc cagtgcagat accaatccaa tctacaaatc taccccccccc cccctcccaa  47100
acctaccaac agaacagcgc ggcaaaaacc taaattctcc cccacacaga ggaagcatcc  47160
gattgcgtgg tcgcatcaca atccgagcac acaccagcat ccgcagcagc ataatcgaaa  47220
cagatcgaaa caggaagagg ggtgggatgg ttcgccgtcg gcgcctcggc tagagcagtt  47280
tggttactta ccccctgctt gccggggatg gtgcagtgcc agatcatgag gttcgccgac  47340
ccgtcggcca tcgtctccgg cttcgccacg aacccctgat ccagagcaag caagcaaagc  47400
accaggtcag aagaaacaca atcggcggcc atagaagatg cgaaaaaaat agaaaaaaaa  47460
```

-continued

```
tcaccgacgt gagggtggtt cttccgccag gccttgcgct cctccgcgag gcggccgcgt  47520
gcgatccctc ccgacatggc ggcggcggcg ggtggttgct ggtttgggct tggtagtctc  47580
tggaaaagaa gaagaagcac cgccttctct aatctctagt cgttcggtct cttgtattat  47640
tatttccacg aaattcgtta atggtagcgt ggaaatcccc gtgcgcgtgg ggcccgcgtg  47700
tcagaggggt aggtagataa gggtatttta aggctatccg gattattcta tccaaaataa  47760
atcttaccaa gttttagcaa gccattgtgc taaaattttg ataggatttc ataagcatca  47820
aagtgaacca gccttagtat ctggttgcgg agcttttaac agttgaagct cctccataat  47880
taaaagtttt ggtaagcagt atagctttct tacccagatt ataatatttt ttacacctgc  47940
attatagtaa tttatatttt tacaatttag aatataaatt tgaagtcaaa aactgaaaag  48000
ccaaagaatc tcataactat caaaataggt gttttaaaat cttaatccca agtaggccct  48060
tgaaatcttg tagaggcgga tattttataa gaaaggcgat attttcgtaa taaacaaatg  48120
gagaatgtga ggcggggatc ttctcgctga gattgcgttt ggttttgtca tcttgcaaac  48180
ggcccagtgt gggaccgaaa caaaagtagc ggaggccggt ggattccaac gttttattat  48240
tattatttta ttattttatt attaataatt tatttttctg tgttgaggag catcaggttc  48300
gcgtgccgaa ttacctccgc ctttttctat ctgttttgct caagttcttt ctttcggttg  48360
caatctcatc tcgcatctgt tctgttctgc ccaaagggac gagagcctca cgaggagagg  48420
aaaaaaaaat gaagcaggga aattggtcac tcgtgagtca aatttggctg ctcggcgtgt  48480
gcatcaagcc tcactttata gagttccttt ttctgactat tgattcatta aatgaataaa  48540
gagaattgat gttggtctag aacattcagt ttcaatcctt gcacgaaaaa aagaggaaaa  48600
gaaaataaag aagaatctac agttccaaag aaaaagaacg agtacactgc agggtgtaga  48660
ctatgacgtg ggccataatt gtcaacgata ttgggccgag tttggcccac tagacccatc  48720
cgtttttctc ttgaggagat aaggcccgca acggttctct ctcctcacct cttgctcgag  48780
ctcgacattg aaccctagag ctccgcattg gatcctcgtc tcgtctccgc ctctccgtcc  48840
tagggttttc ttccacatca ccacgagcca ctgatgagtc ggatctgcgg cgcctgtgcc  48900
ctacaccacc ttcgtattat gcacttgtga tgtgtccgca ggtggaggag gaaacatcct  48960
ccataacccg cagtcgcgat acgtttttat ggtgatcgtc ggaggtggtg caggacacgg  49020
ggagggagga ggaggaggat ttggtgatga ggatgacagg gagctaggtt ggagatttct  49080
gagtgcttcg tcggtttgtc ggtccactgt agctggcgcg ccgaacgaac cataccacta  49140
ggtacgtctc ttcggctata taggcttctt ccttatagtt gcttgcttat tcaataaatt  49200
tttggtcgaa gaaaatattt gatatttttt ttcaaaagca tattcgttaa ttttggtcga  49260
agcctatgac tcacataact aaagggtgga gaggttaatg tacgtacctt ttgagagtaa  49320
ggttaatact cacgaatttt aagtccaaga ggtaagatac ctacaatttt agccaaaggt  49380
tttatataac tcaccaccgc gaggtcttag aatgtgatga ccacaccaat aacctatagc  49440
ccaagcgcgg ctgacaatat cattgccaat atggccgata tccccgccgg ccaccgcgcg  49500
ctaacgagct atacatcatg cacagcggat tccgcaacga gctccatggc ctgctgagcc  49560
tctttgtagg atgtctttgt caaaatgcca agtgcagggc cttcacccgc gctgtcagtc  49620
ccatcgagcc ttttcgtgga ataggagctc gtgggcaaga gcgaagtgct gaagcatctg  49680
ctcgaggcca gggagctggt ggtgaggttg gtggggcgcg ggagtgcagt gcctggtgtg  49740
gctgccagca cgtgcgagtg aagagaggag agagagagag agaggggggg agaagatgac  49800
atgatgtgga agtcgctgac atgtgaatcc cactctcacc cattgaccca atgcgtcaat  49860
```

-continued

```
catggtcaac ctgccacacg agtaaaaacc gcttcccaaa ctattaaagg aggtggtttg  49920
cattggcttt tgaagatcgg ggagacgtta cacccggttt aacagttgag ggaagcaatt  49980
aagggcctgt tcagatcgat gccattttta atcatatcat tttttttggc aaagttgcca  50040
aaaaaatgcc tacgtttagt ttggtgtcaa actttggtaa ggtttatttt ggctacaatc  50100
tgaaagtcct aataagaaca taaagataag ggatggaaag tagacttagg gctcgctcac  50160
ttcattgcca aaatacactt tatcatttgt tggtaaagct gaggagattg gtaatgccaa  50220
atttgaaaa agttaaaata aatttacaac gaaaaatatc tgtctagttt attaacttac  50280
taaaaattag caataccagg aaactggtaa gatttatttt ggcaatgaag tgaacgaagc  50340
ccttaattcg ctaatagcgc ctgtagtggc ccattcgtat gctaattgga ccactgatgg  50400
gctgtcatcg agtaagtggg ccttcagaag gtcgcaatag ttccaaagct tgggccttaa  50460
tgaactatgc cgatgtggga aggagatgac aaacgggctc ggggggtcg tgggcctcct  50520
gctagtgccg cgtgcaagtc agcaaccatc aagccgaatg agagtgtact gggcccgtag  50580
ttgggccgtt cgtagcgatc gtacggccca catcttgtga ttctacggcc atatttttcg  50640
gccttagtct atgctgggtc ccgttgttct ctctctcttt tccaaagaat cattgcagta  50700
cggtggatca aaattcctcc gaacgaattc aaccctttcc aaattccaac gccaacattt  50760
atttaccaaa agaacagaag tagtaaatgt ttttgaagct acccacgttc gtctcacgat  50820
ctttcgacga ggaaggacga ggacgattgt gacatgacgc tacagtaaca acctaagtcg  50880
aggaggggcc ctgcacgtca gcctgaagtg aaagaaagca cacgcctcat ccagatcgat  50940
cattccaact atattaccac cccttccaac ttttctcaag ttgcagctgt gggcatcatg  51000
catcagtgtg catcacggtc tctttgtttg gatggtcgtg tcatatcagc tgctatatat  51060
acgtacgtac gtactcctac tatactgtac ctctgcaact gcaactgcga cctgcataga  51120
cagccaagct gagatatcga tccacggtct gtgaaactta ggaaagccgt tagcttctgc  51180
atccatgcca tcgacgtgat caatctctcg catggcttcc ataaatatcc cctccttcct  51240
tccaaaagga tacttactac tccctcctta attccataaa tattacgaat ttttcagttt  51300
tgaaatttat ctgcggatat aagagatttt agaatagtac tactataagg cggaaataat  51360
ttacttgtag ttatatcatt aaacatgaac ttttcggggt caagagaatc ggtgtaattt  51420
cacctcataa acaacctaaa actcttcata tttgtatata gaaggagtat tactagaact  51480
gattataagc cgtaaattaa agcttattag caataaaatt aggtaaaact taattttata  51540
tatgtgtaat tagcgattta aatgaaaata ctacaaaata aaccattata aaagaaacat  51600
cgacaccaac tctaaaatta aatagttcaa ttttaagttt aaatttggtt gtgtttatat  51660
gctgaaaagc aaacgatgaa ggtaggttgg cccaacctta gacccttgca taaaaaaataa  51720
atctaaaatt ggatgtgact taatctagta taatgaatat ggatagaagg ccaagcagat  51780
acattataaa gtatatttaa cacatctagt tctagatttg ttcgtttagg cggatggagt  51840
agttgccggt tgaaaagttt ctgatgccct aactaggtgt gtgtttattt ggcaattcga  51900
ttatatcgat caccgagtaa tggggatgta ttttgtttta ttaggattaa gattttgatc  51960
aacaattatt ctattataat ataattttg tgaagtaaaa ttaatgttat tagacccgtc  52020
ttcaaaagta cttttatatt attatatttt ttgtcacata gatgatatat tagataataa  52080
attttgtcct aacaaaataa aatacgtcat acatcttaaa atggtgggag tatttgtttg  52140
gattaaccgg ccgttttagg aaaccgtcct taattggcca gttggtttgc cactcaaagg  52200
```

-continued

```
aaacaaaaaa aaaaggcgag gtgaattagt aaagcctcag tggctcccgc tctaatcaga  52260
cacgctagct gctttattcg gcggccaaca tgggaaggtg gatgagattc tgccggatca  52320
ctgaagattg tatagttcct acaggagcta tgttgcctct gatcaccttg cttttctttc  52380
agatatgtgc ttaagtttac ttttcttggt ttcctttcat cttttaagca agggtcaagg  52440
gacatgatat acactttctc tgaggatagt ggagagagat atatatatct cggcatcttt  52500
caaagaaaag gtgtactggt gagagcttat gtggatctta aactcttaat tatagcaaag  52560
ttattagcta ttaatagcca aaatgcggct ttgctaaagc aaaaggagct gatgaaaaac  52620
gtactagatc agctagatag ctagctaggg atatggcgca aagctgggaa caaccttatc  52680
acaacgtcta ctagcttgtt gtcttgtata aagagaacaa attgctatgc attgctaggt  52740
caccgcttgt tgagttgagt tgagtacaat atctttatac tagcttgcgc tgttgcttat  52800
tccattttct ttccacgtag aggatctata ctggacggct tagaatccct cgtatagtct  52860
cgtaccaaca gttatttctg tgtcaaaatg tcaaaagtac gagcgaaaca aaagccggca  52920
tgattcagtt ttctagaacg gtaacggcgt acaatcctac ggtggcgccg tgtcatgaac  52980
atacgagcat gacagtaaat attggccctg ttaatttggt gaggttggag aatctaagat  53040
acagctagct ggttaagtag taaaaggtaa gaatatgagg gcttgtttag attccctgtc  53100
aaaattttac accatgtcac atcgaatgtt tggatacatg cataaagtat taaatataaa  53160
aaaactaatt acacagatta tgtgtaaatt acgagatgaa tcttttaagc ctaattgcgc  53220
catgatttga caatgtggta ctatagtaaa catttattaa tgacagatta attaggctta  53280
ataaattcgt ctcgcggttt acaggcagat tctgtaattt attttattat tagactacat  53340
ttaatacttc aaatgtgtgt cattatatct gatgtgacac gccaaaactt tacactcctg  53400
aatctaaaca cagccagaaa aggtgagttt ttgatcattt tctgtactac tacttctgtc  53460
cagaaacaca tcggagctta ggtgacgatg gatctcttta gtgacatgac tttgaccatg  53520
atacaaaggt ttgaggagga caacaactac atgcatatat attatacaaa ttttcgctaa  53580
tcacggatga aggtttggca ataggttgtt actcgctgtc tttaggctgg tgttatagtt  53640
ggtctcttgt tttccatcaa accgtgattt gtaatttaca gttgttttga ctttaagctt  53700
ttgtaataat ttggtgtagt ttctttgaaa caaatgatat aatgatcttt ttaacttttt  53760
cactttaatg ccattctcaa ccttctaaat ttaatttggc aatgctaaaa tttagtaaca  53820
taactggctg tgtttagttc cacaccaaaa ttgaaagttt gaagaaattg gaatgatgtg  53880
acggaaaagt tggaagtttg tgtgtataga aaagttcgat atgatggaaa tgttggaagt  53940
ttgaagaaaa aaattggaat ctaaacaggg ccaaactaaa catactatta ccaacacgaa  54000
cttactaaat tttggtaatt ctgaaccttt tcattcttaa attttttacc tggtaagata  54060
acaaaataaa cacttttgtc cacaccttac cttaaaaaaa atggtaatgc caaaatttga  54120
taagttcttt ttcttttttt tttgcaatga agtgaacaag cactttatta tctcaaaaaa  54180
atataaggat gtcaagagct tggaatttgt tcaagaagat aagtatttct gtattatttt  54240
ctcacctaaa tcaatcacaa ccatatcttt tttttaccta ctttcttatc ttaatcaatc  54300
acaagtatca ctcaccttct tttaaaaaca tggccattgt tttgtagagt acataatatc  54360
tcttgtttgg ggacttactc ttttttatca gtattcacca caatcttgtc atcttcgtct  54420
taaaatatag ttatttctag catagtaact tttcccaaaa taaagctata ttttcaccca  54480
ccctctcatc tcaaccaatc acaaccattc ttttcaccta ttttctcttt ttccgctaat  54540
cacaactctc ctccactcat cgctacatac tttcttaata ctcgtgtcta tctaaaagaa  54600
```

-continued

```
attacattat gtgatggaag aagtatagaa gtggtagcat ggttaactcc ttttgtacat  54660
cctactgtgt cagtttaaca ttacaattta caaggattct ctccagtagg aagggctctt  54720
tacctctgta ccatgctagt caatctcaat cacctcaaag tatactcatt ccaactctga  54780
aacccaagtg cgaggtcact actcactggt acaacaactg tgcaaaggac aatcacgcaa  54840
tagtaaaatt ttacaagaaa ccgaacaaaa gcttcaaaag gtacgagctg cacctgtcag  54900
gtactaggaa aaacctttaa ttagtacata agagaaaaag acacttacta taattgcatg  54960
gaccacaaat ccactatctt ctaatttaag ctgcccagta caaatctcaa aagaagttat  55020
tccccattgg tttttacatg ctcccatgca caagctcaac aatgcaacct agctacccaa  55080
aactcagcat tcaatatctt ctttcacctt gtttatttgc atggaggagt agtagctagc  55140
agtacactgc tgcttcaatg caacttattg tgttactacc aaatacagat ataaaaggac  55200
atttcagatt gtgtagcgta gttcgaagcc atcagtgaaa ggcacatgca gatggaatcc  55260
ggggagatca ttgcacccct tgtactagga gaggttcgct agatgtgttc atcacttaac  55320
aactataatt catttgtaat taaccaagta tactcgatcg agtatactcc ttctatcaca  55380
aaatataagg agttttgatt atatgggaca tcctaatact acgaatttag ataattaagc  55440
agtttgttca gattcgaagt gataagatgt gtcccataca actttatatt ttgaaacgga  55500
gtaagtaaca aacatatata taggacgtgt catattttac atccaaaaca ataaagggat  55560
gttcagagaa acatctagag gtattctggc tagctacaca acgacttggg tttaaagcct  55620
caccacatct aattatttga tattaggttt tttcctaata ttcacgtctt tataaaggga  55680
tgttcgactg gcttggctat ggcttttcca cgcagctact accgctacta ctagtggctg  55740
caaacctcaa cagtaacagc ggacgcggct aagaaccaca aaacttacaa gtgacgcata  55800
tctacacttt taatgcacgc agatctccag atgatcatgt cactgttact gtactattgg  55860
atccaggacc tactaaccta gctaacagat gattatgcag ggtagcataa ataacagcac  55920
actaatagta tttgacgcta ctccaaagtt gtcaatccac taattccaat aggagtagga  55980
caaggaaaaa ttgtcacaca atgatgacat attattgact tatactaata taagatatta  56040
ggagaaaaag actggaaata tcagccgacg tcggttgtta tccttgttag gcttcttttt  56100
gggcaaggag tgtggttatc cttttaagta attagactgt actagctact aataaccacc  56160
caatatgttg aactctaatc ccttgtttta tcgcaaatta aatggctatt caagagttta  56220
aaacataata catcttcata ttaaccttat ggctagagac cacagaaaga gagaaatttc  56280
aaagacaatg tatgaaaagt tgtgaagtga cactttccac taatagctta ccaccgtttt  56340
ggggctgtaa aactaaaaag gagcacatcc agatacgtgc acacatgatt tcacgtgaaa  56400
aacatattac cctgcgcctt ccaaagtgaa aaaggttaat tattttggtg ccatgttgtt  56460
gtacggcatg cataccgcgc ttaagcatga ataggtgagt aggaagatat gtctcatgct  56520
ctgcactgac taaatttctt tttacaaata ttcatttgcg tctgtacata caagttcttt  56580
atatttgaca aaatttatac actgttaagt agttaaaaac tagtttaaga taaatattgt  56640
taagtttata ccgaacctat ataaaacaat ttcttaaagt gcggtaagac gatagacctt  56700
acaaaaaggt gatactacgg gtgggtttag tttcacgcca aaattaaaag ttcgattgaa  56760
attggaacga tgtgacggaa aagttagaag tttgcgtgag tagaaaagtt cgatgtgact  56820
tttttgggtt caaactttga atctaaaccg gacctacttc caaaaagcct agataatatg  56880
catattgtag atttttaata tacagcttac gccctattat attagtttgc gtatcactta  56940
```

-continued

```
cgcaacccac gtgggtgccc ccacaaccaa ttaaccatgt aaaatagtac aatatattgc  57000
tgtctaccat tgatgcatcg ctgttcatcg atatagacga ccatctaatc tcatagtggt  57060
actaaaatta ttactagaat ataatcaaat gagattagaa cgccgctaaa tcgatattga  57120
aaatgccacg aaccgcacca attatagcag gcccatttat tccggcgagg ttgtctcccc  57180
ggtctttgca acctgtgtgg gtcacgtgaa aactgaaagg gagtcctacg tgcgggatcc  57240
ccacagggga tggcccggat gacgaggcag gcccctgacc gcggctacgt gtcgccatcg  57300
cagcggtccg tccgtacacc cgctcgtgag gccccccgac cggctcccaa ccctcgtaca  57360
cgcccgtggg ccccaccaaa cccccgggat tggcagaaat cgtcggacca tcgttctgac  57420
cccacagtgg gacccaccga gctagggccc acctgtcaca gctgctcgtt cccatgctcc  57480
aagttggggt ttgggttttt ttctttttgc gaacacttcc cgtttggaga ttggaggagt  57540
ggggctgtcg taggcgacgg agacgggatt atggagtact acagtacacg cacagtacat  57600
ttttcactgt tgctagatgc ggtacaggct acaaaggtga ataatctgct cctctctgcc  57660
tttggatcca acggtctata tacgttacgt gctatactag ggatggatgg cactgtagca  57720
atgctggatt aggtcttgcc actcaccact caccagggta ggtgccgttt tgtttctcga  57780
ttaggctaca agttaacatc agatttatgg gttcaaatat agtactagtt tacatcgcat  57840
ttaacagtag aattatttct caaaacaaaa ttgtagtatc tgatttttgg taatgagttt  57900
gtagcatgga atgatgctgt gttctgattt gcacaagaat ggcatgcgta ctatgcatgt  57960
caagggctca attgtgatga tttgtacccc ttttttttgt gaaattcaga tagattgcta  58020
catgctttcc tcttttggtt tctgcatata atcctggttt cttctagagg agttctaatt  58080
tggttgtccc atgttgtaaa taaaattatg attgtaagta caaatggcta taaaattgat  58140
acggcattca caatattata ttgagatatt tctttttata taagattagc acacaacttt  58200
tcattcgagt actgctctca ttgagatggc cagatactat tttctgattg aaaagtccac  58260
gcccatgcat atggttttaa ttaaaaggca catgtgtttt cgtgagaatg tgaaatcaaa  58320
gcatgtcgct attgccatga ttatcctaag atttcacgct cttgcccgca aaaactttaa  58380
cgggctactc acagggaaaa tagttggcag atagccacgc tttaacgtac gattgccata  58440
tatatgaaaa acaaaacaag ccatacgcct agccacttgc ttttgacata tcccactctg  58500
gtgtctggac aaggatagaa acaaacccca ccaccattca tgggccgttt gatttattta  58560
tttctagcaa tggtagattc ttttattggg tcggaaaacg gatgtgagcc actcttgtgg  58620
tacatgttaa cacaacttta actagttcat tttagtgatg agattaggga tttttcgctg  58680
gtctccgtct cttcgagtat gtgttagggg cacatccacg gttaaatcga gaggttcact  58740
ccatagaatc aataatatgt acattaggac atactccctc cgtcctgcaa taaatgaatc  58800
tagctaggac tgaatgtgga tgtgacacgt tctacatcca agactagctg gattggtttt  58860
taatgggcga aggaagtaat aagaaccaaa atggttaaag cttgaccatc aatctaagca  58920
taagagcaag tataatagta ggctataagc cggctaaatg ctgaggtgga tgagagaagc  58980
gggctgtaga cttacagccg gcttgagcat aagaaccaag aaactctgtg agagagacaa  59040
atgggtccta tattaattgt aaagagctaa ctattatata ggtaggctga gagaaagcta  59100
caaagaacct tatagccaat aggtcggctg tattattagc cttgctctaa tgcagttgcc  59160
agaaatgtcc taggcgggaa tacctggggt gcaaatgggt gaattctttc ccaccaattg  59220
gcgcggtccc tctgatctct ctttccccat aggcggaggc cagctaagcg gaaaggggcc  59280
acctggtggt agtgttgggg cggggcctcg cccacttgtt cctacgcccc tttccgcgcg  59340
```

-continued

```
aggaggtggg acgagagacg acggcgatcc acggccaatg gcgattgccg gtctcggtcg  59400
gtcgcactcg cgctcgcgcg cgggcgcctc gtgggtcgcg ggtttcccag gacgggaagt  59460
cgctcgcgcg gtcgccttct ttatttggct acctcctcct cctctcccct ccccacccat  59520
ctcgccctcg tctcgtctcg tctctccact cccccacctc ccatccgcta ctgctagtac  59580
tactactacc cggcctctcg ccttctcgcg cggccgcgat ttccgttcgc aaatccgcac  59640
ccacggcggc gcgaggtcgc cgtcgtcgtc gagccatttc gggtgagagg gggggtctcc  59700
ggtttttctc agatctgtcc acttttgtcc agttttgatc tggtgattta atatactatt  59760
tttcacttct ggtggtttgc ggcgacgcgt gtgcaggggg gtagtttata agggcttgcg  59820
cgaggagggg gaggagtagc gggtagcggc ggctcgagtc gagtcgtcgt cgtcgtcggc  59880
ggcggcggtc gagagagatc gggatcgatg gtgcggggga ggacggagct gaagcggatt  59940
gagaacccga cgagccggca ggtgaccttc tccaagcgcc ggaatggcct cctcaagaag  60000
gcgttcgagc tctccgtcct ctgcgacgcc gaggtcgccc tcatcgtctt ctccccccgc  60060
ggccgcctct acgagttcgc cagcgccccc aggtatacct tcttctcgtt ctcggcaagt  60120
tctcgccgga aattattctc tcgctcgttt cgccctcgtc gtgctgctgc atcaaatgca  60180
aatgcgattt cattctctct ctctctctct gtggtaatcg ggtgattttt gtggtttggg  60240
gggtttgagg attcggctgt tgggattgct tgttcgtcag agtttgaatt cctgccctta  60300
attccgtcga acaaaaatgg gttctctgtt cggatttggc acctgcggat ttggccaccg  60360
ctgctgcgac gacgaagacg acggcgacgg cgaccgccgg ccacacacac tactagtagc  60420
ctactagttc gtcttgcttc tcacttgcta ttattgttat tattggaagc tgtgaactcc  60480
tgtagaagtt gaccccttct ctccccctaa atatctgtac ggccctggag accggatgga  60540
tatgcccaca cctcagcact ctctcacagt caccaccagt tgcctgtagt atctcttctt  60600
cattcatctt cttcttcctc tcacatgtta acaactgttc catggagcat gtccacgagc  60660
tctggattga ttctctggcg cgtctctgtg catcttcctt ccccattcgt cgattcttgt  60720
tctcgatccg cgggaaaatt gacgattaaa ggaggctcct gacctctgaa taaaatcaag  60780
gacaaaaacg tacaagaagg cagaggtaat aaacccaaga tagccaatat acaaagaaaa  60840
accaaagtaa atggcagcca atgggaggaa ggaggccggc cggcgtgcgt ggccagtaat  60900
tgcggggtag gaagaaggct gcgagcctgc gagcgtgcga gactacaaat ggagaaacaa  60960
gctaatgtga catccggtca gtgagatgag agatcattgg gcgcctacct gcaccctctc  61020
tctctctctc tcgatccaca ccactgcact gctcccctct cgatcgtaca ctggctgatg  61080
agctagccaa gttgatttct ctcgcaaaac gtaccacgga ttggtcgcat cagctccgtt  61140
cgtcgagggt atggtgtggg ggtatctttc catcatacac agtatgacgt tggccacagt  61200
acatagcatg cgatatggct gtttctgaat attttttcag ttttcagcag gtccgaattt  61260
gttaggtgga accgtgattt atatatttct cccctcttcc ttgtggatat agtactcgta  61320
ttgtgtatct tactcctagt tctcttgcac ccactccagc tggagagtgg agagagtgga  61380
gagtacgtac cttatctggc gcacactgta ctataatcct tatattttgg tgatcaggtg  61440
caccgtttat tatagattaa tcatcatctc ttagacatgg cttgttgcac cttaatatcc  61500
atctctttat caggcttata tgtctacggc agtgaaaaag cgttgccagt taattcattg  61560
tcgtgcatgt agtttccaaa ccatagtcta gggaacactc aatgttgttc catgatatta  61620
agtgatgtta agtactccat aacttaatta gtactccatg ccaatactcg acaacataat  61680
```

-continued

```
atttccatca cacttcatat atatgtatgc tctccctctt tctcaattag gaagatctat  61740
ctagaaaatt cttgagtttg caagctatga tatgcaacga actttcttct aatgtaagtg  61800
caaaactatg gattgtcatt cattacttac gttacttctt aataaacatt atcaagaagc  61860
tagattgtag agcatgtaaa gctgagtgga aaaggagttt tggtaagcat gtgattgaca  61920
tgtcttatag gtcgtcgatt gatctgccca aacaacagta caaatgaagt taattctact  61980
gtgaatagca tgtgataact cgcaatccgt agaatgcttt ggctttaaaa caataatttt  62040
aagagtgtga gcaatgctta tgttacttca tcagattatc gtgtgcctta attcttatct  62100
gttgatcata tttagtactc ctcctaccca taaatatatg aacacttgaa gcatttaaaa  62160
tttatccaca aatatgatga ttattcctag agtactactg atccctcttc ccaaaataag  62220
tgaccaattt ggatgtaaaa tttgtttcaa gataagtgat cacattacag tgctacttgt  62280
ctattaatca cctcttgttc aaacttctta tcttacctca actaccctcc cacttctaaa  62340
catccctcat ttaggtcatt tgcctttcct cattatttgg ctcatatata agtgataaag  62400
tagcttattc atttatttta gaacagatcg atggagtact tattacaaca atcacccgtc  62460
attcaaattt ctttctaact tacactcaac caccgtccca cctccatctc tctatcttct  62520
cctccaactc tctctctttt aatgaggggc accaaaatat tttcttctca actttaatct  62580
ctactaaaca atttggcatg tgtatatttg ttaatggagg gagtattttc taagttctaa  62640
gtacttgata tatatcgttt aaccagaaat ctatacctat gtgaaaaaaa tacattgtcc  62700
atagatcgat ctttcatgag tatattactg aatcatgcca aatttggcca atgttacata  62760
ttaattatga tcttaaagtt tgttctgaaa ttactttgcc ttgaatcttc caagcaagta  62820
tatatatacg tgtaggcacc acacttctca tggtcaaatt tagatattta tcaacctaat  62880
tagtcagtcc atatatagag agttaatgca actagctagt tgctttgtct aatgtgagat  62940
cttttgtacg tgaactgtaa acattatata tacaacctcc atcctatatt acttgtcgct  63000
ttgagttttt atttgtaatg tttgatcatt cgtcttattc aaaaattttt tacaattgtt  63060
atttatttta tttgtgattt gctttattat caaaagtatt ttaaatatga cttatctttt  63120
ttatatttgc actaattttt caaataaaac aaagggtcaa acgttgtaac gaaaaagtca  63180
aagcgacatc tattatgaga cggaggtagt atgatcggtg tgctgtcttt agtcctgttt  63240
aagatactta atttctctga aatacaattg ctcataatta cagtgttgtt gtcagttttg  63300
tcttctttc caaatacttt atttgaaata tggataaatc aaacttacct tttaccctaa  63360
taaactacac tatacatact aatcttaata acatttatgc ataacattta tggtttttgt  63420
tcattctttt caaatccgtt ccattctggg cagaatgggg caatgcaagt actgtcacaa  63480
agaacaaaga acagatggtg cagccggata tgcatatata tataccagct gaatttttgg  63540
ccgtttcagg aaaacttcaa tttaaaatca atgttggtac tatcaaatta atagctgcaa  63600
agtctccact aggtctagca agaaagtagc agctcaatgg tagtaataac ttcatatgtt  63660
tatcgaacag atattagctt tctttaaaag tccattacca aacaaggctt atctaggggc  63720
atagtacccc catagaccca tatgtaggag taacaaagag aaaatgatta attacaaata  63780
ttttaatggg cttgtttggc agggctccaa ctctaagtac tagctaaatt ctgttctacc  63840
tctctagttc attttataaa agcactctag cattctcctc tctctttgta ggtggagctg  63900
aaaccgtttg gttgggctct agctcaagga gaggtggagt tggagctttg ccgtatgggc  63960
ccaatgtata taaaaaatat ctataatttg gttatagagt atttgtattt caatgggaaa  64020
aaggtatatg tgttaatagt attatactct tctcataaaa atgagtgtga aactaacttt  64080
```

-continued

```
tgtaataatc cttactatta gttagctgag ctcgaactat tctttagtgt acaggcaaca  64140
cgccccaatt ctacaagtgc tgcaaccaaa gctttcaata ctggttttgc cggaaatacc  64200
cgtaccgctt gctggttgtt acttcttccg tttcataatg taagtcattc taacattgcc  64260
cacattcata caaatgttaa tgaatctaga cataaacata tgactagatt cattaacatc  64320
tatatgaatg tgggcaatgc tagaatgact tacgttatga aatggaggga gtattagaca  64380
aatgttcaaa tctaaaattt tgaactcact gtggttcagt aacctgcagg cagagaaaaa  64440
cagcatgatt gaaagcacag ttttgcataa acaatacatc gcaagtagat gaaaactatt  64500
aaaacataat catcaataat gatctgacca gtctaaaaaa atcaataatg atacgcatca  64560
atagatataa gtccatcatg aacaatcata atgcaataat ccatcacaaa acccctacat  64620
agggcatacc acaatattat tccttctcaa attgtaattc aaggtataac acaatttcac  64680
agcacacata aatatcttat tgatcttttc tctctttcca ttagagatgt acctacagat  64740
aacccttcaa agtgaagata aattcatata taaattttca aatatgtttt tctagatttt  64800
caaattataa aataaactgt cccaggcagt tactagacgt tgagatttct aacatggttg  64860
tgccatcaat ggctgtttaa tttctgtaca tattacataa catatagtag ggttgtcaat  64920
gagctgaact tgagcacatg gcacatcaat ttcgttttca agttgaatga atgatctaaa  64980
ttgaccttga gtgaacctga gttggtgcca acaaccgatg ttgaaggtat gctcttgcta  65040
aaatttaatt gaaaacttga gctttagccc gataaggtca cacgaactct atttatgcat  65100
gtctgaatgt gtttcatgca aaaaagaaaa ggcatggcca ataatttcga atccataagg  65160
cttgttagct tacatgtgtt atccttcaat gaaaattata ttctatattg gacaaggttt  65220
cgattcttgt tggtttatat ggttgaaact tttatgcttg gaacaattcc tacctgatga  65280
atcttgttat tattcccaaa gaatagccaa atacaatata tttgtttcta ctatataaca  65340
actacatttt ggcaagtcaa taattttttt ttgcgaggag gctagtcaat aattaagtag  65400
gcacactcct atgcacgcca atcagattat gttgattcag aaacatgcat gcgcactgca  65460
cataagattg ctcattgagg tagttgcatt atttatttag ctaagatatt gccagcatgg  65520
caatgaagca gatatgatga aaatggagga tccagaatat atatcctcag cttttttttc  65580
caattatcaa aaagtttaaa ccatcactag gaagagtgaa gctcttgcat tgttcattta  65640
attaggtgga caacagaagg aacagttcag tttcataata tatagcggtc aagaaaaagt  65700
ttcatattat atataataca tgtgattttg cgacttgata catttatcgt agtatccatt  65760
attcttgtta aactgagcct gccctgccta tggaatgatt acctgaaata ttattttagt  65820
ggaactcagt tatgcctttt atattttatt aaaaagatag aatttgagtt tgtgtcccaa  65880
ttttttgtta ccaggaaaga ttctaaaaaa actcaaaaga tgttgactat ctaatctttt  65940
tgaacaagat agatacttag aaccaaattt acacaaagaa taaagcattt taaaatgtaa  66000
tacaagtaga tgtatttcct agtctggttt gaactgcata caaaaacaaa attgctccaa  66060
aggatgtctg tcatactggc aaatgtagac atgcttcttg aaaaagttgg ctcaaagatg  66120
gtcaattatg caatgttttt ttttcaaata aatatatatt ttttaacata tgtactgaaa  66180
ttgaacgttt tgtgatatac acagaacatg caccagttta acttgcagtc ctgaatttta  66240
ttgatgttta agtgcttgcg ttcacttatt ggtaactata gaacgtccat gcatgtgcta  66300
tcgtgtgtac agcttgggat gtaacatctg aattatgata taataaatat ctaggaaggt  66360
aacaaaatgt tcctcgctag tgctggtgtt gatatatttt cagagaaagc tggaagcgca  66420
```

-continued

```
actgtcaaat caacagccgc ctattggcat tgaaacatac atatctacct ctcgttgttt 66480
ctactttttt ttggcaagaa tttggttgga tatagttggc cataggcctg tagccaccac 66540
tgtttgtagc atcgcaatat gcacagacaa acatttgagc tgctgagcta gcagagctag 66600
ctagtttatt gtagcaggtt ggaacaagca cagctagctc aagtcatgca tgcactaata 66660
aattagagta tgtatgtttt ttgccccaga acgattatat catcgatctt ctgattttta 66720
gtttgctcct tgtgtctgtt ctgcagccta cagaaaacca tcgaccgcta taaagcatac 66780
acaaaggatc atgtcaacaa taagacaatt caacaagata tccaggtgaa tatcttgcct 66840
ccacacacaa tccgcatata tcatgcaaca tatgaaaact atttccttct ttttatgttg 66900
acgagttctt gcgtgatgca gaaggtactg caatttagca attaatggca caattttata 66960
ttgctgactt ttaactttct ggcatgcatt ttaacgtagc aatggcgtgt ttgttaatat 67020
agctctagac tctaggatta caagaaaaca gaatgtccct agctctctag acttggcggt 67080
tgggcaacag aataattagc cttggtggtt ttcagtctat acttggcggt tttcgaccgc 67140
caagaacatt ctgttttctt gtagtgtggt gtggtacatt ttgcggcatc ttcagttttt 67200
tttttgaaa gttgcatctt cagttattag tgctagctta gctaagagaa catactgcag 67260
ttaatttagc aataaaagta caaagtacca aacacattgt aaagtagcgc tacatgtaac 67320
atgttcatca gctgatcggt tgttgggagt cctattaatt tgccattggt atgtctatta 67380
attaaactag atgaataccc cgccgcgttg ctgcgggaaa ttaagttaca taatatgtac 67440
atatatgatg caatataatt attaaaacta aacaaattgg tacttatgaa ttttgagcct 67500
ataaataatt gagattgcat ggtgttatga gagaagaaag aagagacaat ttgaaccata 67560
gatctatcat ccaaaggcta gaaataattg ggatgatgtg gcttaatgag agaagagaga 67620
aatagtaata actacactta gtgtggatga actatataag tagggatgaa aacggtcgga 67680
aacgatcgga aaacaacctc aaccatttcc ataatcatat ttttctcgga aatgaaatca 67740
aaaacggtaa agtcggaaac gaaaatgata tcggaaatat cggaaaaccg gaaacggaat 67800
aatacggacg gaaacatgtc ggtacagatc ggaaaccggt aacaaatacg aaaacgttaa 67860
actatagaaa acatatataa gtatgttata tgtacaaata aattcaagct atactatata 67920
aattataaat taactccatt ttagccatgc actcaagtta gggatttgat tgaagaatca 67980
atcaatctct aaactgtggg tcaagtagag acgtgccctt tagatatcaa catatttaga 68040
aatacggtaa ttaccacatt ataagaaacg gtaattttca taagaatacg gtaaatatgg 68100
aaacgatcgg tacaacagca aaatcatttc cgtttccatt ttcatatttt ttaccatttc 68160
catatggctc ggccggtaga aagtcggaaa cgaacgctag tcggccggga atttccgtta 68220
ccgttttcac ccctatatat aagtaaatag gatgcctgca tcctagtatc ctacacttta 68280
gcaccttcaa ttaattaatt gttgcaggta acttcttatt aagatgaaaa ataattatta 68340
tctgcatgag acttagctga atcaatattt tcctagttaa ctcatatgtg ccaaattcca 68400
tttgtaattt caccaaaaaa catgtgcggt ataaaaatgt atagaagtat tgaagtactt 68460
caatattttt tggggcatat tcttgagtat agtactatag catgtgaaca tgcacgttct 68520
aatttctaag gttgaatcat atatactgca gcaagtcaaa gatgatactt taggcttggc 68580
caagaaactt gaagctcttg atgagtccag acggtaagca atcgtgtctc tttctgagga 68640
gtatgattac atgataatcc tgagagccaa aaaaaaaaat cagtagttca ctctgaatta 68700
catgtgatgc aggaaaatat tgggagaaaa tttagaagga ttctctattg aagaactgcg 68760
tggtctagaa atgaaacttg agaagagcct ccacaagata agactaaaga aggtttatat 68820
```

-continued

```
tagctatttt cagtactcct aatggccatg agaaaattga aggcaaactt tttagaaact  68880
atgaataatc ttctgtttac agaaattatt aacacgcatt cttctatatt atctattcgt  68940
taacactaga ccgagcttct ggagcagcag atagccaagc tgaaagagaa ggtatacagc  69000
cgcaatcaat gcatattcct attccctata gcaatacatc aaactccata tattttttc  69060
cctaactctg gatgttattt ttttccttgc atctctctga tattaggagc ggactttgct  69120
taaagacaac gaaaatttac gcggaaaggt aatcaatgat tatgaacaac cgcctgttat  69180
caggcaaaac aacatatact gcaaactacc tttttcttct tttatccagt aaagctgcac  69240
gtacagagta tatctgatat ctcatgcatg tgctgatgtg cagcctaatt atattatcca  69300
aataaccaga ttgatatatg acccatcaac cacaccatta tttacatgtg caattgattc  69360
atttttacaa caaacttagg ctgtgtgact tatggcagaa tctgagatat aaacaatttc  69420
cattaattat cttgagaaaa tgtgcaattg atctctgcag catcgcaacc ttgaggctgc  69480
ggcgctggtg gctaaccaca tgacgacgac gacggcgccg gcggcgtggc cgcgggacgt  69540
gcctatgacg agcagcacag ccggcgccgc cgacgccatg gacgtggaga ctgatctgta  69600
cattggattg cccggcactg agcgctcctc caaccggtcg gagacaggtt gaagaaggcc  69660
agccacagca acagctgcta tatagcatgc agtagcagca acgacgccag tgacatcctg  69720
ttcatctcac aagaataacc agagctctac gcatgcgcac atgaaaccca ggcatgcagt  69780
tctcggtggg taaattatta tctcgcatta ttagctatat gcgtgtcctt gtctttttct  69840
ttaggcaatg gaataaaatt tccggtaagt acaaacacaa acggaaacaa agaattaaca  69900
aagctgtagc agaccagatc ggcaaattga aatgccaggt aatccagtat atatttcgct  69960
tccagctgcc tctaccctca tatctcacct gcctgtgtgt ttgtgtaaat tgagcttgcg  70020
aaagaggaag gtagatgctg ttaatttatg ggagtggaag ctaaatgttg tactactgga  70080
gtactgattt gtagctgatc caactgccac gagttttggg cgtcgaaatt cctagacttc  70140
ttgacaccga tggatggaaa ttatgccgac ctggcgacat gatccttaag tggtgtttga  70200
atctcgatta agataaagat taagtgtttc acgcaaaacg acaaaacgag gtggtaataa  70260
catgtgatta tttgagtttt aattattaca aacttgaaaa atgaattaat ctgatatttt  70320
agagcaattt tcatatagaa aatttttgca cgaaacacat cgtttagcaa tttgaaaagc  70380
gtgccacgag tatccaaaat ttcattcaac tcttgtcaga gaaacgaacc caacctaatt  70440
tcggccatcg agatttgaat attcgataag gtggtatggt tgtactccct ccgtcccata  70500
aaaaactaac ctagtactag atgtgacata tcctagaata ataaatctag acagattcgt  70560
tgtagtagaa tatgtcacaa ccagtcctag atttactttt tttttggatg gaaggagtag  70620
gtgtttgccg ccgaacagaa ttgcagcttt gttacttctg agttcagacg tctgatcctg  70680
tctgcattgc agcgaatggg ttaatctggg ccttcgaaca aagcttggcc caatgttaat  70740
aaagcccctt ttctcgatgg aatactggga ccaagtaaat cctactaacg gatgatgcta  70800
gtttaagaaa aagtctattt tcgttcctca actatagccc aggccattct ttctttctct  70860
tttttcattt ttaaaaaaca gccccattct aatttttatc ctagctccaa ctgcaaaacc  70920
atttatatga agacttcctc aatcataggt ggttttgtct tacctaacat gttgacatga  70980
tctttgttct acgtggtagt tagatggtgg gttatgtggc gtttaattgt cattattgtt  71040
agtaaaaaaa aaggtggacg cacagtcgca catgtaattc tcttataaat aataaaaaaa  71100
tacaatggta ttctctcccc ccctctttca tcctctctcc tgctctccat ggtggcaagg  71160
```

-continued

```
agcttgagct cttgagtctt gacggtgccc tcaatctagc acggcgtcgg aaaaaggaca  71220
tcccccttgtc actcttggcc cctccctccc ccacccctcg ccttgcccta tagtacaaat  71280
acttaccttc caatgctgat ggtgacacaa ccgccctcca cccctaccca acccgggaga  71340
gagaggataa ctaatagata ccattgtatt tttttatta tttataagag aattacatgt  71400
gcgaccatct atatttctcc accgcaaatt ccaattcacc gctcttttct aacccatgaa  71460
gccgcagctg gtgatgttat caccaccgtt ggttggcact tacccaacca tctttctaaa  71520
ctcaacacat agtaagagaa atttacctct tgaaggccgg tgtctcatgc cgattctggg  71580
gtcatccatg tcggataggt atagtgtgcg gactgaaatt tttgcaaaaa aagtccttca  71640
gtttatttgt aattcgatac aggcccctaa caaacaaacc tctaagctga tgttttacat  71700
ataggccctt acgaaagttg gatatttcat gcaaagaaga gaaaattcac gaatatggcc  71760
gcgcttgaaa atatggaagc tgaggggctt tttcgtaaaa ggctcccacc aagggatgag  71820
aagttaggga tctctgtctg ccgctctgtc caaagaacca acccatatta ggttttcatt  71880
tttcgctaaa aaaaggtatc ttgaagcttg tacacgcaag catatgactg catggtgcat  71940
gatgtaatgg ggggtgccgg tagtgacgac atgcaatcat tcaaattgat tgactttgat  72000
tgccccccaag ggtctgtcaa tccaaattag cccccaaggt tctagtgccc tgtttggaag  72060
attagttcat ggctaatttt aagagttaat gtttagttat aaattggtag gctaaacatt  72120
agtttagggt ggtatgtttg gatccatggg ctaattcaag gctaaaacgt agagagagag  72180
tagaaagaga ggagagagaa ggagagagag agctgctttt ttatggtccc tacacaaaat  72240
tagccccatt agcacccctt gtagggacta atgttttaag gggattaat tcacattagc  72300
tcaaaattag cccacctgtt tggatccttg agggttaatt tgagcctaaa aggtaagggc  72360
taaacattag cccatggaac caaacagaac cctaatatca atctgttaac aaaatagtta  72420
ttagatgagt gcatcgatga ttgagatcct cggtgtcagt gtatatagtt tttgaattag  72480
ctaggaaaca agagtatatt cacgctgccc atgtggtgat taagaaattg acaggatcag  72540
agtgtttgca tagttttaac caaaacatga gttaagctac agcgtacagt ccgatggact  72600
ggctacctac cgcacgtgat tctctactat tataaaaatt aaaaatattt ttaccgatac  72660
tttgaaaagt catttatatt taaatcgatt taaattttat gtttttattt taatttatat  72720
ctcttaacta tcactatctc tataaaaaag aacaaaaaaa tttccgcagt ctgtataata  72780
gaaaaaaaaa tcccactcag aaaggtaaaa aaggaaaaga aaaagtccga cccaaaaatt  72840
gataaataaa acatctgttg tcagttaaaa acatctcgta aaataatcgt ccgacttccc  72900
aaaaaaaaaa gaaaaaaaat actctcgcta gtaaaaaaaa gtccgttttt tttggcaccg  72960
gtatttatcc tgactttttt ttcacgcgaa agagtttttt tcgcacgcgc taaagttttg  73020
gtttttttc gtccgctttt ttttattccg atctgttcac tgcacgcctt cgggcacttt  73080
tggtccctat tttttcgccc gttataatgc attttctcct ccaatttgtc tgcaaaaatc  73140
tccatgattt ccctttcgat tcggctttaa tttgtcagat ttaatttccg tttaacagtt  73200
gccgatgatg acggcgatct tccccggtcg tttttatccc aagttttatg ctctgatttt  73260
agaaagaaaa agggaaatag tagatcgagt ggatcaaaaa tccttaacta attttggatg  73320
atcgagaaaa attcagccgg atttgatgag gagatttgct ccggcaacca tatgggcacg  73380
ggactatctt cggaaggttg aagatggtag tggatgatgc gagctgggtt tacggggcat  73440
gggactatct tcggaaggtt gaagatgata gtggacggtg cgagctgggg ttataggga  73500
agcaggtcaa acggagggag gcagtggcca aatggaggga ggtagtggat tggtctaggg  73560
```

-continued

```
ctgaaaagga aggcaggttt tcatcccaaa accaagaaaa gatttttatt aacttttttt  73620
taattataat ctatatatag caatcccgat attaggattt tcattaacct tttcaattat  73680
aatgtatagt gatcccaata tttcaattta ttacttagct cttattctct taatatatca  73740
ctaaaaaaac atctttaccc gttgcaacgc acgggtattt tttctagcag agaaaaaaaa  73800
aagaaaacct aacagaactt tatgcttaca taacagccaa agacaaatga ttcgtgcaaa  73860
cgagagacta gctatattta tataattata ttccttataa aagaaaaata ctagggaacg  73920
aaactactcg aaaaagcatt ttttgtaggc ggccaaaaat agtttttttca gacggaggaa  73980
ggaccgcctg tagacaaatg actgaaaaaa tagatgattt tcgtaggcgg gcatcctttt  74040
ttacaggcgg tatctattat tttcgtaaga ggtagatcca cttgcttgcg aaaatatttt  74100
taactaacaa aaaaaatcca gcgccaccac ccaacccatc ggcggcgccg ccggactccc  74160
cctccgatgg atccaggcga actagatcca ggcgacgaca gtgtcgttgt cgcaatcggt  74220
ggtgggtccc aagcatcggt gtcgtcgtcg tcacggccgg tggcagaggg agactaagct  74280
gagggggagg agagagaggg gagcaaatcc aggcggcggc gtcatcgtcg ttgcagtcgg  74340
tgtgggaccc aagcggcggc gtcatcatca tcgtggccag cggcagaggg agagtagagc  74400
tgagggagag gagagggagg ggagccgacc tcccctctgc ccaagtcgcc gcctcacctc  74460
ctcgtcgcca ccgcttcccc ttcggccgca cctccactgc cgcggcccct cctctccacc  74520
ggcggcccac gccgccgtcg ccgggggagg gagcctttgt gcctgccgct cgagccggag  74580
ggaaatgata gagagagaga gaggagggta aagaacgagt agtggggagg ataagatggt  74640
ggaggagaag ataaggatag gacttagaat ttttttaggt aggcatgact tttacaggtg  74700
gatcacataa ggttccgcct gcaaaaatca aattttttca ggtggactac ttaagaagtc  74760
cgcctgtgaa aataaaggta tttttgcagg cggaccgctt aagagctccg tctggaaaaa  74820
ttgatttttc gtagatggac ggtgagcttc acctcaattt atattttcgt aggcagccat  74880
ttgactccaa aagtcatacc cgcctggaaa aaaaagccct cactatgcaa aaatgttttt  74940
tcagtagtgc gggatcctat ggaacgtcca ttgcatgata cccacttggg ccgcacatcc  75000
tctccgtgtt gttgcctcca tatcgtcact aacttcggtg ctacgacacc ctgccctcgc  75060
cacttgcctc aacggccata ggcactcacc cctcgcccca ccgttcaata tcgtcgggag  75120
attgtggcta tcaaatctga tattcacaag cttaacattg tcggatctaa tgcctagagg  75180
cttgtagccg tccaacctgg ttggtctggt ggcaaaagaa gatagggagt caacagtgac  75240
gtggaatatc tatactaatt gaaggaagag gaagacaatg gcggtgatag taattagccc  75300
ctttccatgt caaacacgcc gtcccttcat tttcggatt cgacatcctc cgtcaagctt  75360
cttcctcctt gaactccctt tctctcgggc tgacaagacc tcttctgtcc ttagtcaatg  75420
atctcgtcac ccatcttcgg gtacaaggaa agggaagagg aagagggcga tggtatatat  75480
gtttattggt gtgtgtggca gctatctcat cttccttcta gtaccaacgg gtatcggtaa  75540
tttggcatag cgataagtat caacctgata cactagtatt gatgagtacc ggcttgtgga  75600
atcaaccggg tatagcagcc tctcaaaatc agttaaatac tttttacgct gcaaattact  75660
acatttacat tagcagtaaa aaaaatacgg cgtcaaattt tagaagaact tttccgaaaa  75720
tgcttctctt cgaacgtcct atcagatgaa aaacatcaga cgcctacgat cagctcagtc  75780
cttgcttgct aatttcttct ttctctctgt tgacgtcaag gaaataccgt agatcagcaa  75840
cctggtactg tcgtactgta ccatgcatgc atatacctct agctgtttct tttcattctt  75900
```

-continued

```
ttctcatctc tttaaatatt ttttcttcta aattacttat ccgatctacg aaccgatcac  75960
accgttatat tcgttgcaat taaatcttta caacaagata tcatatgatt atatcatgtc  76020
aaaagaaaaa cgtatgtttc aaaccgttaa aacaaaatat ttcatacgtg atagtgatat  76080
gtttcaatat gtgtattaag tgtgtttcac aaaattccta aaactaccta ctactattct  76140
ctctccacct catgcataca tacatgcatg tattttagca agcttcaaaa tatttttctc  76200
ttaatttacc tattcaatct aagatccgat cacaccaata tattcgttgt aattaaatct  76260
ttacaacaag atattgcttg attatatttt gataaaagaa aaacatgtgt ttcaatcagt  76320
taatacttgt tgtttcatgt gtgacagcaa catgtttcaa cgtgtttctt caccatgttt  76380
cataaaatat ttaaatgttc tagttgctga tttttttgt ttcaccatat atataacatg  76440
atgttttact tgttggtcaa ctgcaacatt tgaccatccg tttttttca atttaaaaat  76500
attttaccta atgtactcat gatgttttac tatatatgaa tcaaatgttg tagagagttg  76560
aaacatcctt tcgctattcg ctgaaacatt attttcatat aaggcgaaac agcgtccaat  76620
aaaatatttt cgatctactt agtgaaacaa ttccgatata cttagtgcaa caacgtgcaa  76680
catttaaaaa taattcaata ataagctaaa ttttttttc atcggattat attcatgtgt  76740
ggtcttgttt taaagattta attgcaacga atttaatggt gcaatcagat catgatttgg  76800
ataaatattt tgagagaaaa aatagtttaa aattcgtttg atacatgcat gatggatggc  76860
tagtgcacct gtgcatgaat cggacggttg cgggggcgcc tgatttttct tctcgcgccg  76920
tatgtccgcg cgtagcgctc tccgaacttt tcccaaaatt ggatgctccg ggctggaccg  76980
cgggccgggc agaacgttcc atgcacgcaa ggtacagtgt ttggcaacga cgcggcctcg  77040
cacgtcaact gccgagattt acgtacgcag ttaacaccct aacaacgacg aatcgctgaa  77100
ttcccgtctc aatagacaat agtgatcgtc attgccacac caccataagt accatgtgag  77160
caaaaagaaa ttggtgcaag actgcaagta caaccataga tttcatattc atcctcctca  77220
gatgcgggga aaaaagcagt ctctgttcat ttggaaacag ggacgaggat gagaaatcga  77280
aagagatcac agagaaacag aaaccgacga cggcgattac gcacaacatg gcaacgacct  77340
cactcctgtc aatggaccga tcgatgctta ccattctact actggattgg aaatttggaa  77400
tggcggtgac gaagacgaag atccggtcgc ctggttgacg cgttcaatct gtccacttct  77460
tctcgcgaga tgatccggcc gcgatcgggg gcgacgggag acggcttgaa cgggtaaaaa  77520
gccgcgcagc taagcgacag agattgtcct gctccgccgc ccgcacgacg gcgacagggt  77580
tcagacgacg tgcctacgtc gtgcgatgct cgcggtgagc tagcgttcgt ggaacgtcga  77640
tcgccagtcg gcgcacgcgg ttgctcccag ctcccaaatg tcactctcac tcaccgcccc  77700
ggccgcccta gggaccttcc tgttcctgga tcttcaccgg cgacgacgaa attttgacca  77760
gcaacaggct gtactcggag agttgtacag ttcttgaaag atggcaacgg ggctccgtaa  77820
cgcgagaccc gatagatttt actccattgg gatttaggag tcagtacgta catgtgtatg  77880
gtctaatttt tatacccatg aatttaatgt actagtgggc aaattttttt aattctagta  77940
tggttcgtta cttgtcatat atagtctaat tctaactatc tgtttatttg cttttgattg  78000
ttaatgttaa aattaaggtt actaatatga tattgatggt tgtcgtcgta atcgtatgat  78060
tattgtgtaa aatttaatgt tcacgttggt gtagtgggta tcgatatcta acgggtaccc  78120
attacgcgca cgggtgtagc taccgtgaga atctcgcacg gatgcgggaa cttttaatca  78180
tcacgggtat gggtatagtg taacaaaact cgataggtgt gcaaccgttg ccatctcctg  78240
agctattatt ttgtactact ggctgaatag catgtcgatt tatagtaatt atttaaaagt  78300
```

-continued

```
ataaacaaag tgataaaata ttataaagtt gcattccatt tttttcttaa aaacacagca  78360
caacgcacaa cgtagataac acaagtgctc gtataaacgt gagacactca atcttaaaac  78420
aattagaaaa aattacatgt agatttcttt tcaaaagcac accgttttaa aactcgggaa  78480
gtgcgcattc tcctctcaga agaggacatg gttgaagttt gccgttgcca cttgtcatga  78540
actccaaaaa atgcatggtt gaagtacgat gtggcatggc agtacgaaac gacaactagc  78600
tgacggcccg atagctgctg ccagcgccgt gtatctaatc taaccaccgc ccatcaaaat  78660
atacaatgcc agattgccag gttctataga aaatccgcag cttcagttcc aagactgatc  78720
aatcagagac atcgtctgaa ccaccgatcg atcgagccgc cgtgcgaatc tcgtccgcag  78780
ctagcgcagt gcgaatcgcg tcacggctca cgggcgcgcg cgtaccagcc acgccaagcc  78840
aatctgctgc atgaaactac cgaatcagcc gtgaaaattt tctggttaat taggccccat  78900
tgttgagaag tggaaggttt cagtcaatat atgtacttgt cgaggactgc ggtagggagg  78960
acacatcttt gtcgcttgac catcgctttt tttctggagt ttttctcggt gagctagatc  79020
ttccactact tcgttgtttc cagttccact taattaataa attagccgcc gtgcgcctat  79080
acctatagcg tttgaatgtt tcgtcgcgga cgtggttctt agccgcccac ttcgttttct  79140
ttcatggcta attaggcaag tgaacgtctt gttgataatg attgaatgta tctgagcatc  79200
ttcttttgga atatggtgtt tttcactata aacgaactat atgtctcttt atttagacta  79260
aggctgcgct ctaactaaag gttggctgga gctttttcct cacatgtaca gtgagatgag  79320
ttattagttc atggttaatt aagtattaac tattacaaac ttgtgaagta agtgtagctt  79380
aactggttag gttccatgcg gtggaaccaa ctcacccaga tttaagttat agacttaaca  79440
catatgctcg tatttacggc taattattct ttcagtggta ggtgacgtac ttattgacag  79500
cgaggcgtca gtggtgactt cgtcaatctc aagatatacc ggtccaattt tctgaacata  79560
ctcctagaga taggtagggt gagtgtgcat gtgtgtgagc atctacattt gtactgggtt  79620
tctttaaaat aaaactatta caaacttaat aaatgggttt attgatttcc tttttaaaaa  79680
aacttctgca cagtaagttt tttagtatat acacttcagc tggtgaacat atatactcgc  79740
taaaaacgag gaagtagcta aaccgttaag ctgattataa ctcggtctaa gttttttttta  79800
attagttggc acatgcactt gataatataa tggttgagta tctttagggt ggtctctgtt  79860
ggtactattc tactaccatt tatttttagc aaatcttaac tgttgattta tgagttctac  79920
taacagtgaa aatattctag tgctattggt tgaggtggta atataagaag atatgcatga  79980
tcaatatgta aaaaagggtg aacaaatcaa gattactttt accaccaata gaaaccattg  80040
taaaggtgtc ttcatgtgag aaagaggatg aactggctct atcagaagcc gaagataatc  80100
ccacatgagg aaaatgtgag acagaggaaa cttctaaaaa ggaaatgggg gaagttagtg  80160
aggtctagtt ggtcttggag catcaattca attaagcttt aagacaaata tattttctgc  80220
ccccttagtt ttcacatttt tctttccatg tcattaagtt ttgctccatc catatgcccc  80280
taggctttaa ttaattgcat acacattttt cgttttcaat ctatgtggac catgagtaga  80340
ttggtagttt cttcttgaaa ttactatatt atatactccc tctatcccct agtataaagg  80400
tttgatattt ctcttatact gtttgaccat tcgtcttatt caaaaatttt tggaattatt  80460
atttatttta tttatgactt actttattat ccaaagtact ttaagcacaa atttttactt  80520
tttatatttg cacaaatttt ttgaataaga cgagtgatca aacagtataa gcaaaatgtc  80580
aaaatccctt atattagaag acagagggag tatgtatgta tatatatctc acaattacac  80640
```

-continued

```
ttacaggctg aacataatta tgcatataca gatacattca cgggaggaac tatacgaaaa  80700
ttacatattt tgatatttac tcttagcctc tgcatgtaga gcctattttt tttaaaaaaa  80760
tagttattac atcgatgcca ttataaattt gccaattggg aaagaaatac cattattatt  80820
tgtggtatcg attgggtgtc actgagcttt tgtgaaatta gaaccatgtt atctctgtca  80880
cgttttcttt cttctttctt cttctctggt acgagtacca tagaacaacc caacagagaa  80940
catgtacatg tgttatgtgt tttgaacaaa atacgtagag aggtgaggga cgttggcgtt  81000
cagactgtac gagtccattt tggagagcct tgggctggat ggaggctaca tgagggagtc  81060
cctaagcgtg tgtccctaag tgggatgggt tagacctatc ctagtttttt ttggatggga  81120
tggtttcaat tgtctgtttg gtttatagta tgtaatggtt atatattttt gtttggtaga  81180
agggattgag gtaggatggg ataaacagct ttgcactacc gttagtgcca tctagctccc  81240
aatagctagg gcacagcgag cggcgagcgt gggggcggag gagctcatcg gcgcgagcgg  81300
acgagtgacg gcggtcactt gcggaggaga gacgggtcgt ggacgagtga cggtggtcgc  81360
ggaggcgagg tggctcccgg atctgagagg agtggcggtc gctcgcggag atggcagcgg  81420
gcgtggacga gcgctggcgg atgcggaggt ggtggcgggt gcggacgagc tcacaccgtg  81480
tgctcgtcct aagtgggatg agctcgtctg gccctttttc ccggatggat tggtcctaga  81540
tcagagagga atatttctct ccaaggacca acccatccca cttacccccta aactaaacac  81600
ccctaaaagt gggttcatcc catcccatcc ttccaatcaa acactaccta aggagccagg  81660
agtagcacat ggcagtaaac attatccgcg gtgctcaaag ccagagctca ctatggtctc  81720
cccatgcaca ccgaccccaa caccctcacc atcctcctca tggatgacca ggtcgcccat  81780
ctgtagaccc tcaataacgg caaatggatt gccgttaatc tctgcagccc aacactctcg  81840
tcatcaacat cggcgaccag ctccaggtga ctattcctct cagatgaact tttagaccat  81900
ttttggaatg taagattgaa aaaaacccat gaacagaaat aacgcaaaga tagcaaagtg  81960
aacgtaactc acatggttac attcttgcag tggaacccgt ctatctaaat ttaaatccta  82020
gattactggg tttctttttt taaaaaaata aggtagagat aaaatgacga tgaggcaacg  82080
acacggcatg cgcacctgtg tccttgtggt tgtctctgga ttcgctgtcc agggctgcgc  82140
ttgtacacct acagtagatc tgaaaccttc tcctcgcccc acttttagct gctcgatcga  82200
tcttcgatcc tgcgaagaga tcacggtcca gtacactgta gcccctgtac acccatcaga  82260
tctggctttt tacaaaaaca aaccacaaac cccaaacccc aaccgcagcg tcaccacaca  82320
cggcgcacac acacgcgtac gctaccacca aaacactctg tcgtcctgca gagcttcgga  82380
ttctgcctgc gcgcgcgcgc ggtcgaacac acatggccgc agatcgcgtt gtgcagccag  82440
gaacagagca ccaccaccag caccgacaca tgcccaagga acgaacagaa cagagtattc  82500
ttctcgcctt tcttgcgtgc actagctgat cgatgagttt aatttgggtg tttgacgaga  82560
gcgaagagtc gagacaatga tgtcacgggc ggacgcggct gtgacgcacg caagcagcca  82620
acgactcgaa ggccttcaca gtagtcaact actcctcacc ctctcgccac gtctgcttcg  82680
atcccttctc ctcctccttc cgctataaga ccagctcggg gatcgcctcc cggtgagcca  82740
tgtcgccgga cggtcgccgc acacgccaca gtcgtcgttg cacacacgcg ccgccgttgt  82800
tgtcgtcctc ttctcctccg acgtcgtcgt cgccgtcgcc gtcgtgaaca tggcggcgga  82860
ggcggagcag cagcaccagc tgctgtcgac ggccgtgcac gacacgatgc cggggaagta  82920
cgtccgcccg gagtcgcagc gcccgcgcct cgacctcgtc gtctccgacg cccgcatccc  82980
cgtcgtcgac ctcgcctccc ccgaccgcgc cgccgtcgtc tccgccgtcg gcgacgcctg  83040
```

-continued

```
ccgcacccac ggcttcttcc aggtatcatc atcatcaaca cgaattcctc tcaacaatct  83100
gcagaaattg cagctaagct gacgacgagc tgatcaaaat ccccgcgtgt gattccaggt  83160
ggtgaaccat ggcatcgatg cggcgctgat cgcgtcggtc atggaggtgg gccgcgagtt  83220
cttccggctg ccggcggagg agaaggcgaa gctctactcc gacgatccgg ccaagaagat  83280
acggctgtcg acgagcttca acgtgcgcaa ggagacggtg cacaactggc gcgattacct  83340
ccgcctccac tgctatcctc tccaccagtt cgtccccgac tggccctcca atccgccctc  83400
cttcaagtac aaatttctat tttgtctcag ctctcctaca catttagtta ctgcattcat  83460
gcttgccatt cgccattcag tatcggttac tgctaaaaca cgtttgaaat tgactgcgat  83520
taatttattt ttggaccatt tctactccct tagttctaaa atataggagt agcatatagg  83580
agcaactttt agcgttaaaa atctatatcg gaatataata aattatctgc ctatttaatt  83640
tcactcatct caatcaatca caactatcac atatttaatt ttactcgtat atttaaaagt  83700
gtaaaaaaat ttaaaagtat ttaaaacaga gcgtccatta gcacgtgatt aattaattat  83760
ttgctaattt ttttaaaaaa tagatcaata tgatttttta aagcagcttt cttacagaaa  83820
atttttaaaa aagacacacc gtttaaccgt ttgaaaaaca tgcgcacgga aaatgaagca  83880
agggagttgg gagcttggag ttccgaacac actctacacc atttcctttt gtagttgcac  83940
gttagcaaac attttcaaaa ggtaaatggt ttgctatcat ttaaaacatg acgcattaga  84000
gaggatgaag cataaataaa ggtttggccg gtctattaca cagacataag atcaatcctc  84060
aagtcagtca gtctattcac atatcacaag ttcacaaata acaagatatg cgacaaagga  84120
tatcatcaat cttgtcaaat tctacttggg aggtcatgac agaatgtagg aatgcaagcg  84180
ggcaacccac tgcctgtata aaaaactgtc ttatagttta tttactactt gctactataa  84240
agtttgaaag aaaaaatcaa ctacaattgt aataaccgga agaaaataaa acaccgcttg  84300
ctcgggcccc ttacatccct acaatattgt taattggaaa aagattctga tgggattgaa  84360
actattgtac tgttccagag cttaataaaa gtaacataga tttataattt cactgaattt  84420
tactttgtaa ccatatatag caataggatc gaataccaca tatatcaaat tggcaggata  84480
atttgaagta gggaccacta atagttggaa aagtaaaaga acaacctagg ctcaacctgg  84540
accgcaactg ctggaattgg ctggtattag aactggaatt ggtaggtgcc ataattccaa  84600
attccagcca tttcggccgg taccgaaatg aaattgataa catttggaaa ttgcaatgct  84660
tatcacgcta gcttctaagc ttcatgctcc gtgtcacctt ccactatgta tttttttttt  84720
taagtaaagt ccatcaccgg tctctaaact tgtaccgttg tgtcatcccg gttactaaac  84780
tcgcaaatcg accgttcagg tcctcaaact tgttcgactg tgtcattctg gtccctaaac  84840
ttgcagatca ctcgtttagg tcctccaact tgttcagttg tgtcacaccg gtccctaaac  84900
aggacggtct agagacttta tatcaaaaaa ataatttata actttttcat gtgaactcta  84960
atgaagacaa actttatatc aaaattgtag ctctcgatgc gacctacaac tttttagttg  85020
gaaagttttt gaattaaaac tgtttagggt cccaaaatat tgttgcatgt ttatagattt  85080
tgaaatttta attttaaaat tgcattttgg gacaaaaaat gacttaaaat aaaaaaaaat  85140
tcaactacaa agttgtagac cgtgtcaagg gctacaaatt tgatataatg tttatcttca  85200
ttagagttca cattaaaaag ttatgaatta tttttaaata taaagtcttt agaccgtcct  85260
atttgaccca gatgatattc aaatccaagt ttagggaccg gggtgacaca actaaacaag  85320
ttagaggacc taaacgagtg atctgcaagt ttagggaccg ggatgaccca gtcaaacaag  85380
```

-continued

```
tttgagaact tgaacggttg atttgcgagt ttaggtaccg gaataataca gcggtacaag  85440
tttagggacc ggtaatgaac tttactcttt tttttttcac aagtcagagt gagcaatttg  85500
ctctcgaata catctacttt gataaggact gagattggca tgcataacaa caaaacgatc  85560
cttgatgtta cacgtacggt ggagcttttc aagaatgtgc agtcactgaa tcacctagct  85620
aaaacctaag agatatgctc ccctttgctt ctctgaacat ttagcgcgca caaacgcaga  85680
tagatacctg aagccaagaa agaaacaaga gaaacgagcc atcaaaggtg gcaaacaaaa  85740
ccacgtgatt caggaacgtc gtctcatagt ctatatcaat ttgatttttt tcccgtaaac  85800
acgtaaaagc ttaagagata tacttgatag tgcagtgtca aagagtgtgt ggttttaatc  85860
ttgtggtctc gtgttcaatc tttaacacgc tcacaatttc ttcttagaaa atgtttggaa  85920
ggacgtccct ctccaaatct tgttttcttt aacacgtact ccctctgtcc tataaaaaac  85980
caacctaata ccggatatga cacatcctag tactacaaat ttggacatac atatgtctag  86040
attcatagta ctataatata tcatatctgg ttctagattc attttttatg ggaccgaggg  86100
agtaaaagct ctccacgtta atatattaga ataagagttc agcatctagc taatgaccat  86160
atattctgca ctgtgcgtgg ccatggttcc accatgtgcg caggtagttg ttagttgcgt  86220
gcaccgtgca agaaaaacaa ggtagttagt tgcttgatgc tctcacaaat gtttaatgta  86280
atcgcctaaa gaaatcagag catgcgacac tgacatcgaa gacaatgccc cgttgcaatc  86340
tctggaattg gaatcagaat ccaaaggtta caggggttgt aacagcggcc acatcttttg  86400
attaagaaac caagaagcac atgcatggcc acatgtgaac aagtgagaat atacaaggat  86460
aaccacaacg tgatcaacca cgtgcagaaa tattttttca agataacgta ctacttgtcc  86520
aaaatctatc catgtctgtc tgtactctgc aggcccattc agttttcagt gatgacaggt  86580
gctgttcttg gcttcttaac ttgtccaaac atacctcact tcaatacaga gaattttcaa  86640
tataattatt acttattcct tcgtcccata aaaaaataac ctggtaccgg atatagattt  86700
gtctagattt atagtattag aatgtatcac atccgatact tggttgattt ttttatgaga  86760
cgagagagta tccctcaact ccaaaatata gtagtatgac aaagtagtac ttgtggtatc  86820
taatcatagt attaggtttt tatattttag gacggatgaa gtacttaatt gatcaagcga  86880
ctgatcgaat tcgtgatgac attgcaggga gatcatcggc acgtactgca cagaggtaag  86940
agagctaggg ttcaggctat acgaggcgat atcggagagc cttggactgg agggaggata  87000
catgagggag acgttggggg agcaggagca gcacatggcg gtgaactact acccacagtg  87060
cccggagccg gagctcacct atggcctccc cgcgcacacc gaccccaacg ccctcaccat  87120
cctcctcatg gacgaccagg tcgccggcct gcaggtcctc aacgacggca agtggattgc  87180
cgtcaacccg caacccggtg ctctcgtcat caacattggc gaccaacttc aggtgaccat  87240
tcctctcaga tcatcttagg cctcttttca tatctaagat tgcaaaaaca cttagacaga  87300
aaaaacgtag caataaagtg acgattaata acacaaaaaa gttttagaac taacatttcg  87360
atgacacata ggaagaacac aagaaatttt caagtcttag gaaacatgag gtagaacctc  87420
atgatttatt tcttccaaat ttttcatgga ttgctccatt ttataagggc tgtgtttagt  87480
tcacaccaaa attagaagtt tggttgaaat tggaacgatg tgacggaaaa gttggaagtt  87540
tgtgtgtagg aaagttttga tgtgatggaa aagttggaag tttgaagaaa aagtttagaa  87600
ctaaacacgg cgaaggttga accctttgat ctagaggtct ctgtaagaaa aatcctaata  87660
tgatgcaaat tcttcaaatt cctccacttc tcaatttgtt tcataagagg gctgagaatc  87720
tttcagtaaa gctgcatgta gaacgtgttg atgtctgaaa ctctgaactc tgaacattaa  87780
```

-continued

```
attgctgctg gttctgtcag gcgctgagca acgggaagta caggagcgtg tggcaccggg  87840
cggtggtgaa ctccgacagg gagaggatgt cggtggcgtc gttcctgtgc ccgtgcaaca  87900
gcgtggagct cggcccggcc aagaagctca tcaccgacga ctcgccggcg gtgtaccgga  87960
actacaccta cgacgagtac tacaagaagt tctggagcag gaaccttgac caggagcact  88020
gcctcgagct gttcaggact tagctcatcg caagctcact ctacgagtcg acattaaaac  88080
cgtgaggcga acactacaca ctgtgaccct gaccacctcc gaattaagtt tgagttctct  88140
cttggatgcc tatttgctct ctgttaattg gacactaaat tcctcagcgg cctccattcc  88200
tagcttcact tataaggaaa aagagagcac aaagagattt cgttaatagc catcataggg  88260
aagtgtggat tgtgttgaag gtcctaatca gttggttttt tgtccctggt tttggatatt  88320
aggagggtct cttagtatct ttctttttgt ggaacaactt tcagtgtctg taactctgta  88380
ttcctttttt tacttgcaaa gggaatggca tcctttgtgg ttgtagaact ccttttcaat  88440
atcagtcttt atcatactct atcgtttcgc ttattcccgg aataagcgaa acgacatatt  88500
tacaaatgga aaataattta tgaataaaaa ctttatttat gtgttcttag cgatctaaaa  88560
gtaaaagcta aaaaataaat ttcgatgaaa aaagcctcaa aattaactct aaatttgagg  88620
ttgaaaattg aaattttggc tgataaatat aagcataagt gaaaagataa ggccgtctgt  88680
tcctactacg gatctgcggg actcggcaaa tatcacgccc ccgtctaaca tacctgttgc  88740
ccacttccga tcctttttcc tgctatgctt ttggggtttg tggaatcaca tatatgatat  88800
ggtcttcaga catctacaac cctgtctcca tcgattactg cgacgttgta ttgacgatgc  88860
gaccctatgg gctgaaagaa ttaagcgctc cgataggatt gtggttctag cgtggaaaaa  88920
tgttctacaa cgcccctaac tactcatctg tagtggctcg ctgctggcaa tgcccacgct  88980
catgtaacct tgtaacccca agcttactac tcctttcaat ggaagattca ggtggggaac  89040
ctctccccta cggtgatttc taaaaaaaaa aaactctttt ttcatgattc ttggaaatgg  89100
gaaagcagtc acgaagattt gttcagttgt gtaggtgggt taattgtggg gcaggcccaa  89160
aacggtacat ctcgggtgat agagcccatg catgtcatgg gccgaactgg ttctcctcca  89220
gaacgggggg cccacctcgt ttccccagcc cactcaaacc tgcaggccta gtgagcttat  89280
ggtgggcttt tcaggaggcg aagcagccga gcccatgaag ccgaagcaga gggtgaattg  89340
ggcctgagat gtcagccgcg gttcatgggc ctaccgctgg gagtggccgc atcagcttga  89400
ggtccagttt tgggagtctg tgaccagctt ccagagacca ataatcttat aaactcccga  89460
gtatattgaa aattctatcg ttgtggcaac gtcaaattga cccatataag acacacaacc  89520
ctttatttta gagaaaaaga aactttctgt gcatacatat cctcgattag gtttgctaat  89580
tctacctcag gacacatcta tccatatcca tcaagcaaat gcaagtacgt gtgcccacac  89640
tgaacgttct tgtgtggcgt ttggccgttt gcaatgatgt atgtaatgga ttagagagag  89700
gtcattatcc aaaaaagaaa aagggattat aggtgaggtg acacgtactc tccatggatc  89760
aaccatctcg gaaacagttt ggatgatctg caataaaacg ggagtatagc atgatccaag  89820
gccatacaaa tgcccaaacc tcatcttatc agtttcccgc ccgcaacgtg tggtacccat  89880
cccacccatc cccactttta tccaagccgc cggcctccga tccctccacc cccatcgtcc  89940
gcccgtacgc cgtccgtccc actcccatct cgcggccgct attactacca gcagattgac  90000
gacaccgatc gaccgatcga tcgtactacg tgcagagagc ttagctagct gcgacgcacg  90060
cacggtttgt acaaggtaca gtatagtatg acaccgaccg tcgcgaccac caccccggcc  90120
```

-continued

```
gccgcggcgg cgacgacggc ggcggcggcc gaggtgaagc cggcgaagcg ctccgtcggc  90180
ctcggcctcc ccgcgcttcc gccattattg cccggcctcg cctcccacgg ccagccccgt  90240
gtcgcgtcct tctgtgagtc accaccgacg accagtagta cagctgcttg ctcactgctg  90300
atagtaggca cagcgtcgtt gtgctgatac gtccgaagtg gcgttttaat ttgcaggcaa  90360
gaggctggcg aggaacgtgg tggccatggc ggcgggggag gcgccggcgg cgccgctcgc  90420
cgccaacgcg gagatcaccg agttcatcaa cgccctcaaa caagaggtag atatacacaa  90480
acacactctc agctgaaatt acgtgtcacc aatcgctttg tatataccat tgttgcgtgc  90540
agtgggacag gattgaggac aagtacgcgg tgacgacgct ggcggtcgct gcgtcgctcg  90600
ggatgtggag cgccggcgga gttgtatcgg tcggcactca aaaacatgct cacacttgca  90660
tttctttctt tctttcttaa ttgtgaattg tgtaggtata cagtgattaa cttgggtttt  90720
tgcttgattg ccttgcaggc aattgacagg cttcctatcg ttcctggtct catggaagct  90780
gttggcattg gctacagcgg ggtaagaact actccctcca tcccctaata caagagattt  90840
tgatattttg tttgtattgt ttgaccactc gttttattca aaaaatttgt acaaatataa  90900
aaaaaaaaca aaaggttata tttaaagtac tttggataat aaatctaaat ttttttttaat  90960
aagatgaatg gtcaaacagt aaaagcaaaa tgtaaaaatc ggacggaggg agtaagatac  91020
acgtcagagc aaaaaacttt gtttctagaa gtatgattac tgctgcatta taccaactgc  91080
tttgggaact gttcaagtct gaattttctt acttagttca ttgctgtcat ttttccgtcg  91140
agttccatct cttgataata tgttgcttct gatgcagtgg tttgcatacc ggaacctgct  91200
gttcaagcct gacaggtacg tcatcaagca caactatttt atccaacctg caaagtgcaa  91260
aggcttgaca gatgtgagtc ctaactcaaa ctattgtgtt gaattgcagg gaagctttct  91320
ttgcaaaggt tagggaggtc tacgaggata taatcagcgg ttaacagaga tactacttat  91380
atacaacttc agttcaaggg aggctgctac tggattaatt atctgtactg tatcacagca  91440
tagcatctaa tttaattgct cttactcaat gtatgtctat ataagttgga cattactgct  91500
aaataacatt tttcagaatg tttactcaga gttgaaattc tttgtcaatt gtcctttttt  91560
tttttctgtc aagctagtag catatctctt tctctttttt tttagagaga gggagaggga  91620
cagagccata gccatgggca tgttactctg ttccatcatg attggaccaa agaaatgcag  91680
attcaaacac tcaacaattt acacggaagc acgtccaaac cgacagagag ttagcgtcac  91740
taatcaattt tattatcatt cgcggccagt tcacagttac acaatctcac gtcggattca  91800
aggacaaagt tgccactatt tcctcttgac ttaatcgacc tcgctcccat taacttacac  91860
atgattagtc aaatcacgca tatatacgtg ctcgcctcaa atgcaaacat gatcgatcac  91920
ctcgcatata tatatatacc gctcgagctg ttcgtcgttg caccagccag cggcgagaaa  91980
atcacatttg cattcgcatc aatcaatcac aagctaccta gccgagcgcg gtgatggcga  92040
tgaagagggg agccacggcc gcgctgtggc tggtcgccgc cgtcgccggc atgctcctgc  92100
acgccgacgc gcagacgctc gtgtacaagt actacgccca gaagtgcccc gccgccgagt  92160
ccatcgtgtt cgacgaggtc cagaaggcgt ggaacgccga ccggagcatg ccggccagcc  92220
tcctccgcct ccacttccac gactgcttcg tcaacgtaag ctaagctagc aatggcgtcc  92280
ccggtcgtcg ccgagttgat gtaacgccgg tttgattttc agggttgcga cgggtcggtg  92340
ttgctggagg cgagcgacgg gcaggcggag aagaacgcgc agccgaacct gagcctgcga  92400
ggctacgacg tcgtcgacag ggtgaaggcg aggttggagg cgacgtgcaa gcagacggtg  92460
tcgtgcgccg acatcctcgc ctacgccgcc cgcgacagcg tcagggtcat ggtgagagag  92520
```

-continued

```
cacgtcgtcc acacgccgac atcctcgcct actcacgcag ctcagttgta atcacattct  92580
ttctcatcgc cggctggcat ttgatggcgt gcagaccggc ggctacaagt acgaggtgcc  92640
cggcgggagg ccggacggga cggtgtcgcg ggcgagcatg accggcgacc tcccgccgcc  92700
gaagcagcgg aacgtggacc agctggcgcg gtacttcacc agcaagggcc tgaccgtgga  92760
cgacatggtg gtgctctccg gcgcgcacac gctcggcgtc gccaggtgcg gcacgttcgg  92820
gtacaggctg acgagcgacg gcgacaaggg catggacgcc gcgttccgga acgcgctgag  92880
gaagcagtgc aactacaagt ccaacaacgt cgccgccctc gacgccggca gcgagtacgg  92940
cttcgacacc agctactacg ccaacgtgct cgccaaccgc accgtgctcg agtccgacgc  93000
cgcgctcaac tcgcccagga ccttggcgag ggtcacccag ctcaggggca accaggcgct  93060
gttcacgagc agcttcgccg ccgccatggt caagatgggc ggcctccgcg gcggctacgc  93120
cggcaaggtc cgcgacaact gccggcgggt caggacatga tcgcgatgag cgaatttgca  93180
cgcaagatcg agcgcggcac gatcgacgga ttgaattcat tgcttcatcc atgactttct  93240
cctcgattaa tcttcttctc tcggtttcag cttgtatttg tttgttcacc ttttactggc  93300
tcaccgccac cattttgttc agattcaaca atatttttg tacacataac ttcttgattg  93360
actgttcttt tctttattct ggatttttgt tttcactttt cccaagtact taaatagcgt  93420
gattcgtgca aaaattttct tgaaatattt tttaaaataa catagtagtt agtttattcg  93480
tttataccct taaacatatc acataaatta aattgtccat caatttcaac tatctcaaac  93540
agggatataa acattggccc atattattcc atttacagga tatattcgat tcactcctaa  93600
agttcagatt atgttgactc tagtcaaact gcttcaaaca ggatgcagtt tgcacaaacg  93660
ggcacggccc atcagataag agcaggccat aactcacgag ggcccatcag atagatacag  93720
cccaacaggg tatgggccgt ggtcagccca gccgccccgg cagttcacac gccggatcag  93780
agtccctcgg cggccgggcc aacggcgaag cgcgcccagt tcgcggcggc ggaaagccgg  93840
caagttcatg acctcgccgc cgccggcgtg gcccccattc tgacccaaat gtgaacaaac  93900
atgcatctcg tggtcgcaac cccggatacg cctttgcaca agccggcaaa accaacgcgc  93960
atttggcgct tttgtcatgt gctaagagcc taataatctc gtaaaagcgt ttcttgatag  94020
cttgatgatc atgttctctg aaccagaaag ttcaggcaag ctgctgctct gctctaaagg  94080
aaaatggctg gcctggctag ctagctcaca gtttttatca aaggcatcga tcgctagctg  94140
tactgcagaa gaagattacg gggacccatg gaacagcaag gctgcaacct gcaggagagg  94200
cagttttgca gaagccgttc atactgtctt tggattcagc attcttgaca acctgaacac  94260
tgttacatgt tcagtgtaca tgtaacagtg agctgccttc ttcggtttgt tctttactcc  94320
ttgtcttatc agccacacct aaaatttaaa ttttaaatct taattttaaa attaattttg  94380
attttttatc gtagtttata ttttacgttg gctttaaagt tactaataag acatatataa  94440
aagtatttct ataaaatatt tttagtcggt tatgatcagc tctatgcgaa acgatgtgag  94500
ggttagacaa cgaaaatacg tgtgactact gctttctgta tattcagtag atattaaatt  94560
agtacatgat aaccaaccat aggacatcag gacatttctt ctgtaggcat tcagttgtta  94620
aacggatgta cagtatattt tatcggattg gctcccgatc caaactgtat tataaagatt  94680
gattccttac cctgaggtca aaattctgac cggcaagagt cgtttaacat cgaagaatct  94740
tgtcaggaca tgagctctac caaacacgat cgcagcatgt gcatcgcagt cgctactctc  94800
attcagtcac ttactcacag tctcacacca gtggcctgaa tcagtagcag attagccgtt  94860
```

-continued

```
gcaaggtggc tctgtacatg ttcttgctga aaatataact ccacttgact gaatcatagc  94920
cttatcttcc ggacctgcat gtgtagatct cactagtttt ttcacacatc aaatctgaag  94980
tatgaactcg tgagtcatga gtctaatgac cctcttagca tacggagaaa ctaatactac  95040
tgctgttctg taataacgaa ttagtgaaga gtctcctctg tctccaacca accaaactgg  95100
atgctttgat gctacgttgt taattccaat caacattttg atatggaaac acagattaga  95160
aaggaggtgc tttctaatta actagcaagc aaacgtcgat gaaaccgagc atgcagtgag  95220
ccaatcattt gatccttgct ggattctttc tagctgggaa gcatttgcca ctactctaca  95280
gtatacatta ctgcctggaa cttaattggc tgtcaggaat caagttttct attccattgg  95340
gtacgtatct gattctccca attgcctctc cttgcagatt acagacatat actgccattg  95400
aaatgggact aaaggcacag attggaccat cctatactgc aattgtatag aggatttgtt  95460
aatttggacc cccaaatgca acataacgac accccagcgt tagccccagg aaataattta  95520
tcatttcatc agaagaacaa gattatccag cagctcacaa aaaaggctca ccaaactgta  95580
aaggagacca taaacattta ttcagaattc agtcctagca gaaagccaaa cattcactac  95640
tgatgcttca gctgtaacta cacgatgtca tagccaacat ccaatgctgt caatgtagca  95700
acacaggaaa cacaatattc ctcacatgaa caaggggaaa gtctatttgt tcctttgagg  95760
ggacgtgcga gatgattcta attaatctcc aggatggacg tccacccatt tcttgcatgt  95820
aaactaaatg gttataaaaa aattcaaaaa aaatggcaag atagattaat atataatata  95880
tcactctaca catatgtaat tttaaattct acttctacaa gttgtaataa aaataacaaa  95940
ttaaactcta tctaatatat gcaattatta gtcaaattta ttatttttgt tataatttat  96000
agaagttgaa tttgaacttg tatgtttgtg gaatgatata ttacatatta agtcggagtg  96060
cttgccccct ctctctctgt tttttttttt ggtcatgtga catagagtgt caccggaaca  96120
ccacaaatgg cagcttcgat ccgtcgttgt gtgctcaaga tgtactactg catgctgcgg  96180
ataaaaacag gggagtactc cttctaccta cacagatcga tcgatgaatc gatctcgctc  96240
gctttccatg gcccccaatc atgttacaaa aagaaaggcc cccaattggc agcagaacca  96300
caacttttca ctaccaacct atcccctctg cacatggacg gcatctgtca cacactgatc  96360
atcatcactc tctcccccca gctcaatcaa tattccacta attaaaccct ccattgatga  96420
ttttctatat aactcactcg cggccactct tccattgtcg ccttacttaa ccaagaagca  96480
tagccatagc tagtgatcga tgtgtccgtc cattcctgta taaaaaagat aggcgttgta  96540
gcgagcacta tcactaagcc gtatataaag agagcagttt agtactaaag tgagtgtgct  96600
agtgtgagct tagtggcaat ggcgatgaga ggcggtggtg cgacgatgct gtcgtggtac  96660
ttgcaggtgg cggcggtgag cttgctggcg atggcgacgg ggctggaggc gcagctgcgg  96720
gtggggttct acgacaactc gtgcccggcg gcggagatca tcgtgcagca ggaggtgagc  96780
aaggcggtgt cggccaaccc gggcctcgcc gccggcctcg tccgcctcca cttccacgac  96840
tgcttcgtca gggtcagtag tgccaatcca ccattcttgc tcgatatatc gatcagctgc  96900
atgcgagagt ggctggatgt gatgtggttg tggatgattt ttggatgtgc aggggtgcga  96960
tgcgtcggtg ctgatcgact cgacgaaggg gaaccaggcg gagaaggacg ccgggccgaa  97020
caccagcctg cgtgggttcg aggtggtcga ccgcatcaag gcccgcgtcg agcaggcttg  97080
cttcggcgtc gtctcctgtg ccgacatcct cgccttcgcc gcccgcgaca gcgtcgccct  97140
ggtacgtaat tagagaaatt ttacagtaca taagagatat ttaaattttt aatgcaaatt  97200
ctcttaactc ttagtaccga aggtatcaat ttttttaata gaaaatacga tatctattgg  97260
```

-continued tattttctca agcactataa aatctcttag atgtaactac acactctcac acactatcgc 97320
acttgtcaat tactcgtacc cattgccgtt gcttcagtct tacatctgcc agcttttgca 97380
actagacatg atcatatatt catatgggtt ttgcaacgta aagcttaatc tagatatagc 97440
gcacgtacga tttgggaggg aaaaaaaaag ctaatcttga gtgattctga tctatatatg 97500
catgtcatgt ccccaacttt tctgcacacg ttggcacgtt gccttcacca catgatgctg 97560
gcatgctgca cggggcggag ctagtatagc taggggggtgc ccaggaactc ggtttaaaat 97620
ttttttact tatagtttat ctattttcac catatatata ccccgtcagt ttaaacttag 97680
gtatcagtat taagctaaat ttgattcaaa ccagagtaaa gcaagcgagt ggaacccccct 97740
cattttgttc tagctgcacc tgcattatta cagaaaaaaa gggagattga tgctgaagtt 97800
tgtttgtgtg gcgcgcagac cggcgggaac gcgtaccagg tgccggcggg gcggcgggac 97860
gggagcgtgt cgcggtcgtc ggacaccggc ggcaacctgc cgccgccgac ggcgagcgtg 97920
agccagctga cgcagatgtt cgcggcgaag gggctgagcc agcgggagat ggtggcgctg 97980
tccggggcgc acaccatcgg cgcgtcgcac tgcagctcgt tcagcagccg cctgtaccgg 98040
gcgggcacga cggccggcgg cgccggcggc gggcaggacc cgaccatgga cccggcgtac 98100
gtggcgcagc tggcacagca gtgcccgcag agcggcggcg ccgccggcgg cggcgcgctc 98160
gtgcccatgg acgccgtcac ccccaacgcc ttcgacgagg gcttcttcaa gggcgtcatg 98220
aacaaccgcg gcctgctctc ctccgaccag gcgctgctcg gcgacaagaa caccgccgtc 98280
caggtggtcg cctacgccaa cgacgcctcc accttccaga gcgacttcgc cgccgccatg 98340
gtcaagatgg gcgccgtcgg cgtgctcacc ggcagcagcg gcaaggtcag ggcaaactgc 98400
agggtcgcct gatgcaaatc ggtaagccat agcttagctc gccgtgacaa cgtgacgtat 98460
catgtatgta acgtgcattt tgtgtgtgcg tgtgtgtgta tggttggttg gttgtgcatc 98520
aagagctaga gctctctatt ctttggctga tgatctgtat taattctttg tgactgtgtg 98580
tgtcttttga gagaactgta agttgtaact agccatgtgt gccaaatggt gcttaataat 98640
taaaaaaaag agaagctaat taattgttga ttctgcaata aaattaaggt tggatgtggc 98700
tgcagcgctt tgggcatcct tattgagatg gcttgaaaag ccccagtcaa gcagaccgtt 98760
tctaacatgt tcgaggcatc caccttcttc gtgccagggg actgagagtc aatgctcttc 98820
tggactgacc aatggattga tggccgctca gtggcttcct tggctcctga tctcctcttc 98880
gccatgcccc agcgcctccg aggttcacgc acggtcgctt ctggcctggc gaacaattcc 98940
taggtttcca acatccgcga cgcactaact gtttcggcca tctcccagtt tcttcttatt 99000
tgggacgcag tgtttcacgt ccagctctcg ccgggtgtcg aggatcgtct tgtttggcgt 99060
tggaagatga ccagcgctac tcagcgcgtt cggcgtacca gatgtgcttt tatggccagc 99120
acttctttgc ttgtgctgat cttttctggc atgtgaagag tcctgctaaa tgcaagttct 99180
tcctctggtt tgcatttcaa cgacgctgct ggatggccaa tctcctctag aagcgcggca 99240
ttgatagtca cttggtctgc cccttttgca ctcaagagct tgagacgggg cgaaccacat 99300
cctcttcgat tgcgtgttcg cttggtaggt ctggctccgt gtgttgttgt ctcttggttg 99360
ggttgccctc tctccctccc ttggtagctg cctctaggat tgatggcatt cgtctagggc 99420
atgcttgcct gagcatctcc gtcctagctt cgattctcta atcctcctgg tctcctggca 99480
actgtggaag gaacggaact ccagggtttt tgactctgtg ttatctttgg tctcagaggt 99540
cctacagtcc atcctttcag agggccatct ttggtcgtta gttggcattg ctaattttgg 99600

-continued

```
ggttttcgga gagtagtgga ctatgtcccc ttcacactgt ttggagtcgt agtatcgagt  99660
ttttttttccc ttggtctttt gtttccctcc tctcttggta taagtcggtc tagcttaatg  99720
cgttgtgtaa caaatatttt tttcttctaa tatattaaca tgcaattctt ttgcgcattc  99780
gagaaaaaaa taataatcaa ccttgacatg gctgctactc gacttccagg ttaggcaagt  99840
tggaggataa tggtccaatg gccttaagta gaaacctcaa ttcctcaagg cctaattcgt  99900
tgggcctaat acacagatat aaatctttgg gccttgttaa tttgattcgg cctcaacaac  99960
ggcccatcca agtgtacgag cggcccatca cgaagcttaa tcggttaaga ttcatactgg 100020
gccatacttg actttgccca ctgctttaat tggcccactt ctcattttga atggttcttt 100080
gttttggata tatagattac tagacactac aagtgcacca ttgcataact cgatctttca 100140
ctgggaagct ccatgattaa cttgccgaac agtgaccgaa atattttatg cttatttagt 100200
tatctgcaaa attcgactac atttctagca ttgtagagca tgccatggat ggatggacct 100260
tgtttttgtt cttttgtagt tgtcatgtac ttagtaccag ttagtgtacc acacataagg 100320
agaaggggtg tacagatgca tatacagtag tattgatctg atgggaacgt gtaccatggt 100380
ccaggtgacg cattgcgcat gcagaacata taatatatat ccgatacatc gcgcgtgtgt 100440
gtgtgtctct ctctatatat atatatgtat gtaccctcta tttctgcatg tggccaatat 100500
atatttcttg aatttccttc attcttaaat aaatcaattt gtatatacga ataaatgtca 100560
tatcctaatt catatataga agttgataga cttatttaac tagtaccatc aaaaaagagt 100620
tatagagtta aaaaatatca ccatatgttt cattaacatc attctcacgt acgatagtat 100680
tttacaattg ggtgatgtta ttccgtgaca gagagaggag tagaggacat ggctgatggc 100740
ctggaaggct ggaagctgcc tgctaaaggt acttgtatac tgtagtacgt acatgtatac 100800
tgtagacaac agtgagtacg tacttgtagc tacccataac taacctatat acgtaccatg 100860
tgcttaggca aaataaggcc actcaggctg tgtttagctc acactaaagt ttaaaagttt 100920
ggttgaaatt agtacgatgt gatagaaaag ttgcgtgtgt atgaaaggtt tgatatgatg 100980
gaaagtccga agtttagaaa aaagctttaa aactagggtc tggggataag taaaataatg 101040
gaagatacaa ggacggcact gtacgttttg aaaatttcta ggttatatgg ttgcagagat 101100
gattgctcca tcgatgagtg ctccacacca agatacatgt actaaagtat agcactcttc 101160
gacttctcat tctacacaaa attaaaagta aaagtgcact catataagcg tgattgtgca 101220
tgcctatcag gatttgaatc cgcttcatta gttatttaca cccttttttac ttctcatgtg 101280
attttttcca ttcttgtaat tgtaaatatc ttgtaattgt aggaaaactg cagtactaag 101340
tatcaagaag aaaatggtaa attcgtaaca tattaactat tatatgaagg aaaaatacaa 101400
gtctagagag ttaagtttga tggcatgaat cccagaaaat catatagcta gctagaacaa 101460
gagacacaca tatatagagt tgcaagttaa ttgtttcttt catggatttt agttaaataa 101520
gtattccttc cgtttgaaaa tataagtatt aatttctaag ttgtttagaa aatacgaagg 101580
ttaaggggaa aatatttcct ttccattatc gaatggataa atttgagtat taaattgttt 101640
ggattaccct cccaagcacc gatgaaaatg tgtatagatt tctgtacatt agaatctttt 101700
tttcgcgaac gcacaaatcg attgcatgtc aatatattaa aagaaaaata atttttgtta 101760
cgtaacacaa tcagttgtaa ctaggtaaaa gaaggggaaa ttactgcggg aaaaagctac 101820
tccaaataac gagagggtgg tagtagagcc acactacatt cccaaccccc cctcccacac 101880
aaaaaaaaag cggcgatgcc cgcggaagac cacagacaac cttccgagtg aatgaactct 101940
aaaaccacgg agactaagga gagcgccgag tcgaataccc tagagtaccg gtccttccac 102000
```

-continued agctgccaag agaccaggag gaccagggag ttgaagccgg cgcgagatgc tcaggtaagc 102060
aggtcctaga agacggccac cagacttgaa acgagctgtc acgtgcctta gaaatacata 102120
gtatactgta atacaaaatt tgaatcctat aaatgctgga cggagggagt acttgacatc 102180
atttctttca tcttaattgt gacaaaagat tcatatgact ctctttaata gtgcaatcac 102240
ttgtcctggt aatgtcttgt gtggggaagt catgatgaga atattcaatt atccgtggtc 102300
cagtggcctc ccttttgtca gaacacatag cacatttgat cgacataagc tagatagaaa 102360
gagagatatt tttttcttgc ggttagtttg tatgtatgct ttgctgtgtg atctatatct 102420
aaattggtgt ggatcaataa gtataggttt tcgaaataac attcaattgg cacatgctga 102480
tatattacca ttaattggtc ataagtttga gctttttatt agctgatttt tagtttgggc 102540
atgtttttac aaactcgaat gatctatata atttaaataa aaaattttag ttagattaac 102600
aaccacttta ctttgcagtt tagttaactt cctcgaggta tacattgagc agaccaagtg 102660
catgatggat gccaaaaggt tgtttcctta aaagggtttt ctgaagtaac atggtaccac 102720
ctaaattttc atgaaccata tatcacgcat ttgaggtaat tatttcttga agttcatgga 102780
tgggaagtaa accttgaaat tgtgttttta gtcatgaaaa ctccaagtag tagcctaatt 102840
caaaattcaa acctacaacg cctacaaatt ggaccatcct atcatccgat tcaagatgct 102900
cccaaccaat agaggggggcg ctacataccc tgccctccac gcaaaaatag ctatcacctg 102960
tctctctcgg tcacgccaag acagacgact cgtgacccgc tttaattcag tcggctcacg 103020
cgggatacgc cccggaccag tacaacccac acacccaatg caaaccgcgc acgcacaggg 103080
caccgacgga cgaacaaata gagcacgaaa gtagtcgacc ggtattgatc gcggaacagt 103140
actcggtacc cccacttgct gcaaccccac acctccttca cctccttcct acctagacca 103200
gtaatgagag aataagccaa tggtgggtac atagacagat gaaggtatct acccacttat 103260
gtctagacct ttgaaagggg gggacaactg ttcatagccg gccatgatgc tcccatgcat 103320
aaattgcaca tatatatgca ttatgtaagc atcccttttg cctgcatttc agcagcgaga 103380
gtgtggagag gaggaaacac gcgagcatgc atacatgcat gcagagtttt ggcagcgatg 103440
tactgtacgt agagattttt attaattttt tttcactcct cggtagctgt gtctctgaca 103500
tggtggtccc ggaggacaca tcgagcccac gtcgacgtgt gcagtaaaat tggcaactcg 103560
accacagtaa gatctctgca gtgtggctaa cggtgagcag ttttgtctgc agtgaagact 103620
acgccagctg tgtgactgac atgtgaggcc ggatggatgg cgggcccaca tggcagtggg 103680
gagatgagtg gcatatgaga tttaggctcg gtttgggaag cttaatattc tgagaatctg 103740
ctagttgtta gccagcttct gagaatctag agaagctggt tttatcagct taggttgtag 103800
tttattttct ggattctaca actataaatt tttaaaatct aggtaacaat ttagattgtt 103860
tggggagtta gaaattatag gagaagctac aggagctaga agccccttaa acgtaccctt 103920
aaatggcgtc acaggtgaca ggtgggtata aaaaaggaat gagagcctgc gctgcgaccg 103980
gcagtggcga ggcatgcctg ctactgttgc ctttgcctgc tgctgtcgct gccgggtggg 104040
accacggact cgtggacctt agaacattgc cttgaggccc cacctcctta cacatttctc 104100
gggtacccgt accaggacga gacctgcagt ttgttttctc aaatgataca gtgcattact 104160
ggagtactat taattatttt tttcctttgg ttttgctcct gtataatgtt attgtttaca 104220
tgcactaatc ttaccagatt ctttgcttga attagtttgt aggaatagat tcatagtgat 104280
aagtgaaatc tttcacattt tcaataggaa cttaaatggc gatgtattat atcggcaata 104340

-continued

```
cacatacttt agtacttcat ttgttgaaaa aaaatattcc ctatatttca aaatataaat 104400
atttctaata ttcaaaattt gtatcacaat ttaaaccttt ttaagacact aacatctatg 104460
cacaaaaatc aaagcattct taatcaacaa gcttgattaa agggaatcta aacaatcaaa 104520
attcaaattt caaccaataa cgtgtttgaa aaggaatcat ctccctcaaa gttaatcgta 104580
aattatagac ctagaaatat ttatatttca aaacagagac taagatggac tttgactata 104640
aatatatatt ttttacattt ttaatgtacg attacaaaat catagtcaag ataatacttt 104700
caagcatatc tccaacgatg ttaattttat agcaaatctc atcctaaaag taacattatt 104760
agattaatag ttggtcaaag ctcaaaattg tacggtcaaa actcacgaac gatggtattg 104820
cattactcct aggtacacgt acgcgttcca gtttattgtg cttctgcggt ttcttagagt 104880
tatcaaagga cctttattaa ttacgagcta gacaaattaa atttcaaagt tacaactttg 104940
ctgcatgcca aaacaaaact ttatttacag cttccttttt ctcttttgtt tcgaggagaa 105000
tggaccatat gcatgatgta cagtactggc aacctagcta gccatgcgac tgctttcttt 105060
gatattcttt tttgattttt tagaaaaaag cttgtgggat cactttgata tagctagatc 105120
agtgcccatc tcagctagct attccgtcta atcaattact agtgctttga ccttgctagt 105180
ttgatttggc gagcatgcgc acaaattaat ggagcacagt attagcaagg aagaaccacc 105240
atgtatctat atataatatg tttaatttga tggtcttaat ctgggaaact attgggatga 105300
cactttttcc tctactcttt cccttcttgt atttgtcaag cgaatattac actgctggta 105360
aataaggagt atattcggtg aaagccatga aatatgtgaa aacccataaa aaccggacct 105420
aaaagttttc aaaatttttct ctatttttta ttccaaatga aattgagttt ttacttattt 105480
aatggttttt tatgaatatt tcctagaaaa ataaatagtg taccttttacc aatgtcgtgc 105540
aatagaaggc aacaaagtta tttatactat tttcttaatt ctcatgcata ggtcactatt 105600
tttttttca taagatcacc tggcgaagag attacttacc tgaattttca ctgcaagggg 105660
aacaacttat atttaaaatc agatagagtt attttgctat tgcttttatt tgatggagtt 105720
gatcggagaa acttttgtag tacaaaagaa ttacttatct ttccttatca acttaacttt 105780
tgtgttgaat tggggtcggt aaatgcaact caatatatta tcagagatat atctcgaatt 105840
```